US010953393B2

(12) United States Patent
Lin et al.

(10) Patent No.: US 10,953,393 B2
(45) Date of Patent: Mar. 23, 2021

(54) STABILIZATION OF ACTIVE METAL CATALYSTS AT METAL-ORGANIC FRAMEWORK NODES FOR HIGHLY EFFICIENT ORGANIC TRANSFORMATIONS

(71) Applicant: The University of Chicago, Chicago, IL (US)

(72) Inventors: Wenbin Lin, Chicago, IL (US); Kuntal Manna, Chicago, IL (US); Pengfei Ji, Chicago, IL (US)

(73) Assignee: The University of Chicago, Chicago, IL (US)

(*) Notice: Subject to any disclaimer, the term of this patent is extended or adjusted under 35 U.S.C. 154(b) by 40 days.

(21) Appl. No.: 15/767,862

(22) PCT Filed: Oct. 12, 2016

(86) PCT No.: PCT/US2016/056649
§ 371 (c)(1),
(2) Date: Apr. 12, 2018

(87) PCT Pub. No.: WO2017/066328
PCT Pub. Date: Apr. 20, 2017

(65) Prior Publication Data
US 2018/0361370 A1 Dec. 20, 2018

Related U.S. Application Data

(60) Provisional application No. 62/380,784, filed on Aug. 29, 2016, provisional application No. 62/240,178, filed on Oct. 12, 2015.

(51) Int. Cl.
*B01J 31/16* (2006.01)
*B01J 31/22* (2006.01)
*B01J 35/00* (2006.01)
*B01J 23/75* (2006.01)
*C07C 5/03* (2006.01)
*C07C 41/20* (2006.01)
*C07C 67/303* (2006.01)
(Continued)

(52) U.S. Cl.
CPC .......... *B01J 31/1691* (2013.01); *B01J 23/75* (2013.01); *B01J 31/2208* (2013.01); *B01J 31/2239* (2013.01); *B01J 35/002* (2013.01); *C07C 5/03* (2013.01); *C07C 41/20* (2013.01); *C07C 67/303* (2013.01); *C07C 209/24* (2013.01); *C07C 209/62* (2013.01); *C07D 207/06* (2013.01); *C07D 209/08* (2013.01); *C07D 213/127* (2013.01); *C07D 215/04* (2013.01); *C07D 307/79* (2013.01); *C07D 333/54* (2013.01); *C07F 5/02* (2013.01); *C07F 7/083* (2013.01); *C07F 7/0805* (2013.01); *C07F 7/0896* (2013.01); *C07F 7/188* (2013.01); *C07F 9/5059* (2013.01); *B01J 31/121* (2013.01); *B01J 2231/323* (2013.01); *B01J 2231/344* (2013.01); *B01J 2231/64* (2013.01); *B01J 2231/645* (2013.01); *B01J 2231/646* (2013.01); *B01J 2531/0216* (2013.01); *B01J 2531/16* (2013.01); *B01J 2531/22* (2013.01); *B01J 2531/38* (2013.01); *B01J 2531/48* (2013.01); *B01J 2531/49* (2013.01); *B01J 2531/56* (2013.01); *B01J 2531/62* (2013.01); *B01J 2531/72* (2013.01); *B01J 2531/842* (2013.01); *B01J 2531/845* (2013.01); *B01J 2531/847* (2013.01)

(58) Field of Classification Search
CPC ... B01J 23/75; B01J 31/12; B01J 31/16; B01J 31/1691; B01J 31/22; B01J 35/002; C07C 209/24; C07C 209/62; C07C 41/20; C07C 5/03; C07C 67/303; C07D 207/06; C07D 209/08; C07D 213/127; C07D 215/04; C07D 307/79; C07D 333/54; C07F 5/02; C07F 7/0805; C07F 7/083; C07F 7/0896; C07F 7/188; C07F 9/5059
See application file for complete search history.

(56) References Cited

U.S. PATENT DOCUMENTS

2015/0031908 A1   1/2015   Bury et al.

FOREIGN PATENT DOCUMENTS

CN       104445079 A       3/2015
WO    WO 2012/025559 A2   3/2012
(Continued)

OTHER PUBLICATIONS

Manna et al., "Salicylaldimine-Based Metal-Organic Framework Enabling Highly Active Olefin Hydrogenation with Iron and Cobalt Catalysts," J. Am. Chem. Soc., 2014, 136, 13182 (Year: 2014).*
(Continued)

Primary Examiner — Paul A Zucker
(74) Attorney, Agent, or Firm — Jenkins, Wilson, Taylor & Hunt, P.A.

(57) ABSTRACT

Metal-organic framework (MOFs) compositions based on post-synthetic metalation of secondary building unit (SBU) terminal or bridging OH or OH$_2$ groups with metal precursors or other post-synthetic manipulations are described. The MOFs provide a versatile family of recyclable and reusable single-site solid catalysts for catalyzing a variety of asymmetric organic transformations, including the regioselective boryiation and siiylation of benzyiic C—H bonds, the hydrogenation of aikenes, imines, carbonyls, nitroarenes, and heterocycles, hydroboration, hydrophosphination, and cyclization reactions. The solid catalysts can also be integrated into a flow reactor or a supercritical fluid reactor.

20 Claims, 34 Drawing Sheets

(51) Int. Cl.

| | |
|---|---|
| *C07C 209/24* | (2006.01) |
| *C07C 209/62* | (2006.01) |
| *C07D 207/06* | (2006.01) |
| *C07D 209/08* | (2006.01) |
| *C07D 213/127* | (2006.01) |
| *C07D 215/04* | (2006.01) |
| *C07D 307/79* | (2006.01) |
| *C07D 333/54* | (2006.01) |
| *C07F 5/02* | (2006.01) |
| *C07F 7/08* | (2006.01) |
| *C07F 7/18* | (2006.01) |
| *C07F 9/50* | (2006.01) |
| *B01J 31/12* | (2006.01) |

(56) References Cited

FOREIGN PATENT DOCUMENTS

| WO | WO 2015/069926 A1 | 5/2015 |
|---|---|---|
| WO | WO 2015/149068 A1 | 10/2015 |
| WO | WO 2015/149072 A1 | 10/2015 |

OTHER PUBLICATIONS

Lammert et al, ChemComm, Cerium-based metal organic frameworks with UiO-66 architecture: synthesis, properties and redox catalytic activity, 2015, 51, pp. 12578-12581. (Year: 2015).*
Laurier et al, Journal of the American Chemical Society, Iron(III)-Based Metal-Organic Frameworks as Visible Light Photocatalysts, 2013, 135, pp. 14488-14491. (Year: 2013).*
Chakraborty et al., "Nickel and Iron Pincer Complexes as Catalysts for the Reduction of Carbonyl Compounds," Acc. Chem. Res., vol. 48, pp. 1995-2003 (2015).
Das et al., "Functional Mixed Metal-Organic Frameworks and Metalloligands," Agnew. Chem., Int. Ed., vol. 50, pp. 10510-10520 (2011).
Evans et al., "Crystal Engineering of NLO Materials Based on Metal-Organic," Acc. Chem. Res., vol. 35, No. 7, pp. 511-522 (2002).
Falkowski et al., "Privileged Phosphine-Based Metal-Organic Frameworks for Broad-Scope Asymmetric Catalysis," J. Am. Chem. Soc., vol. 136, pp. 5213-5216 (2014).
Furukawa et al., "The Chemistry and Applications of Metal-Organic Frameworks," Science, vol. 341, pp. 1230444-1-1230444-12 (2013).
Furukawa et al., "Water Adsorption in Porous Metal-Organic Frameworks and Related Materials," J. Am. Chem. Soc., vol. 136, pp. 4369-4381 (2104).
Genna et al., "Heterogenization of Homogeneous Catalysts in Metal-Organic Frameworks via Cation Exchange," J. Am. Chem. Soc., vol. 135, 10586-10589 (2013).
International Search Report and Written Opinion corresponding to International application No. PCT/US2016/056649 dated Dec. 30, 2016.
IPRP corresponding to International Application No. PCT/US2016/056649 dated Apr. 26, 2018.
Kesanli et al., "Chiral porous coordination networks: rational design and applications in enantioselective processes," Coord. Chem. Rev., vol. 246, pp. 305-326 (2003).
Kreno et al., "Metal-Organic Framework Materials as Chemical Sensors," Chem. Rev., vol. 112, pp. 1105-1125 (2012).
Lammert et al., "Cerium-based metal organic frameworks with UiO-66 architechture: synthesis, properties and redox catalytic activity," Chem. Commun., vol. 51, pp. 12578-12581 (2015).
Lan et al., "A Luminescent Microporous Metal-Organic Framework for the Fast and Reversible Detection of High Explosives," Angew. Chem., Int. Ed., vol. 48, pp. 2334-2338 (2009).
Li et al., "Metal-Organic Frameworks for Separations," Chem. Rev., vol. 112, pp. 869-932 (2012).

Manna et al., "Chemoselective single-site Earth-abundant metal catalysts at metal-organic framework nodes," Nat. Commun., vol. 7, No. 12610, pp. 1-11, DOI: 10.1038/ncomms12610 (2106).
Moulton et al., "From Molecules to Crystal engineering: Supramolecular Isomerism and Polymorphism in Networks Solids," Chem. Rev., vol. 101, pp. 1629-1658 (2001).
Nguyen et al., "Vanadium-Node-Functionalized UiO-66: A Thermally Stable MOF-Supported Catalyst for the Gas-Phase Oxidative Dehydrogenation of Cyclohexene," ACS Catalysis, vol. 4, No. 8, pp. 2496-2500 (2014).
Ouellet et al., "Enantioselective Organocatalytic Transfer Hydrogenation Reactions using Hantzsch Esters," Acc. Chem. Res., vol. 40, No. 12, pp. 1327-1339 (2007).
Pullen et al., "Enhanced Photochemical Hydrogen Production by a Molecular Diiron Catalyst Incorporated into a Metal-Organic Framework," J. Am. Chem. Soc., vol. 135, pp. 16997-17003 (2013).
Ravel et al., "Athena, Artemis, Hephaestus: data analysis for X-ray absorption spectroscopy using IFEFFIT," Journal of Synchrotron Radiation, vol. 12, pp. 537-541 (2005).
Rehr et al., "Theoretical approaches to x-ray absorption fine structure," Reviews fo Modern Physics, vol. 72, No. 3, pp. 621-654 (2000).
Sawano et al., "The first chiral diene-based metal-organic frameworks for highly enantioselective carbon—carbon bond formation reactions," Chem. Sci., vol. 6, pp. 7163-7168 (2015a).
Sawano et al., "Robust, Chiral, and Porous BINAP-Based Metal-Organic Frameworks for Highly Enantioselective Cyclization Reactions," J. Am. Chem. Soc., vol. 137, pp. 12241-12248 (2015b).
Sheldrick, "A short history of SHELX," Acta Crystallographica Section A, vol. 64, pp. 112-122 (2008).
Sheldrick, "Crystal structure refinement with SHELXL," Acta Crystallographica Section C, vol. 71, pp. 3-8 (2015).
Shustova et al., "Selective Turn-On Ammonia Sensing Enabled by High-Temperature Fluorescence in Metal-Organic Frameworks with Open Metal Sites," J. Am. Chem. Soc., vol. 135, pp. 13326-13329 (2013).
Thimmaiah et al., "Multi-component synthesis of 2-amino-6-(alkylthio)pyridine-3,5-dicarbonitriles using Zn(II) and Cd(II) metal-organic frameworks (MOFs) under solvent-free conditions," Author Manuscript, pp. 1-9, 2012 [published in final edited form in Tetrahedron Lett. 2012, vol. 53, No. 36, pp. 4870-4872].
Uemura et al., "Polymerization Reactions in Porous Coordination Polymers," Chem. Soc. Rev., vol. 38, No. 5, pp. 1228-1236 (2009).
Wang et al., "Asymmetric Hydrogenation of Heteroarenes and Arenes," vol. 112, pp. 2557-2590 (2012).
Wang et al., "Metal-organic Frameworks as a Tunable Platform for Designing Functional Molecular Materials," author manuscript, pp. 1-32, 2013 [Published in final edited form in: J. Am. Chem. Soc. 2013, vol. 135, No. 36, pp. 13222-13234].
Wiers et al., "A Solid Lithium Electrolyte via Addition of Lithium Isopropoxide to a Metal-Organic Framework with Open Metal Sites," J. Am. Chem. Soc., vol. 133, pp. 14522-14525 (2011).
Yang et al., "Metal-Organic Framework Nodes as Nearly Ideal Supports for Molecular Catalysts: NU-1000-and UiO-66-Supported Iridium Complexes," Journal of the American Chemical Society, vol. 137, No. 23, pp. 7391-7396 (2015).
Yu et al., "Catalytic Hydrogenation Activity and Electronic Structure Determination of Bis(arylimidazol-2-ylidene)pyridine Cobalt Alkyl and Hydride Complexes," Author manuscript, pp. 1-43, 2013 [Published in final edited form in: Journal of the American Chemical Society 2013, vol. 135, No. 35, pp. 13168-13184].
Arrowsmith et al., "Magnesium-Catalyzed Hydroboration of Pyridines," Organometallics, 30, 5556-5559 (2011).
Bart et al., "Preparation and Molecular and Electronic Structures of Iron(0) Dinitrogen and Silane Complexes and Their Application to Catalytic Hydrogenation and Hydrosilation," J. Am. Chem. Soc., 126, 13794-13807 (2004).
Behrsing et al., "Cerium acetylacetonates—new aspects, including the lamellar clathrate [Ce(acac)4] 10 H2O," Inorg. Chem. Acta, 352, 229-237 (2003).
Bellow et al., "Reactivity Modes of an Iron Bis(alkoxide) Complex with Aryl Azides: Catalytic Nitrene Coupling vs Formation of Iron (III) Imido Dimers," Organometallics, 34, 2917-2923 (2015).

(56) References Cited

OTHER PUBLICATIONS

Bull et al., "Synthesis of Pyridine and Dihydropyridine Derivatives by Regio- and Stereoselective Addition to N-Acitvated Pyridines," Chem. Rev., 112, 2642-2713 (2012).
Burgess et al., "Transition-Metal-Promoted Hydroborations of Alkenes, Emerging Methodology for Organic Transformations," Chem. Rev., 91, 1179-1191 (1991).
Casey et al., "An Efficient and Chemoselective Iron Catalyst for the Hydrogenation of Ketones," J. Am. Chem. Soc., 129, 5816-5817 (2007).
Cao et al., "End Group Functionalization of PFpP Macromolecules via Fp Migration Insertion Reactions," Macromol. Rapid Commun., 37, 246-250 (2016).
Chakraborty et al., "Iron-Based Catalysts for the Hydrogenation of Esters to Alchohols," J. Am. Chem. Soc., 136, 7869-7872 (2014).
Chen et al., "Selective Catalytic Hydrogenation of Heteroarenes with N-Graphene-Modified Cobalt Nanoparticles (Co3O4—Co/NGr@α-Al2O3)," J. Am. Chem. Soc., 137, 11718-11724 (2015).
Chirik et al., "Getting Down to Earth: The Renaissance of Catalysis with Abundant Metals," Acc. Chem. Res., 48, 2495 (2015).
Choi et al., "Chemical Environment Control and Enhanced Catalytic Performance of Platinum Nanoparticles Embedded in Nanocrystalline Metal-Organic Frameworks," J. Am. Chem. Soc., 137, 7810-7816 (2015).
Comito et al., "Single-Site Heterogeneous Catalysts for Olefin Polymerization Enabled by Cation Exchange in Metal-Organic Framework," J. Am. Chem. Soc., 138, 10232-10237 (2016) (DOI: 10.1021/jacs.6b05200).
Crabtree, "Iridium Compounds in Catalysis," Acc. Chem. Res., 12, 331-337 (1979).
Delacroix et al., "Hydrophosphination of Unactivated Alkenes, Dienes and Alkynes: A Versatile and Valuable Approach for the Synthesis of Phosphines," Current Organic Chemistry, 9, 1851-1882 (2005).
De Quadras et al, "Monophosphine and diphosphine ligands for diplatinum polyynediyl complexes: Efficient syntheses of new functionality-containing systems and model compounds," J. of Organomet. Chem., 692, 1859-1870 (2007).
Dolomanov et al., "OLEX2: a complete structure solution, refinement and analysis program," Journal of Applied Crystallography, 42, 339-341 (2009).
Dudnik et al., "Atom-efficient regioselective 1,2-dearomatization of functionalized pyridines by an earth-abundant organolanthanide catalyst," Nat. Chem., 6, 1100-1107 (2014).
Edraki et al., "Dihydropyridines: evaluation of their current and futrue pharmacological applications," Drug Discov. Today, 14, 1058-1066 (2009).
Fan et al., "Organoborane Catalyzed Regioselective 1,4-Hydroboration of Pyridines," J. Am. Chem. Soc., 137, 4916-4919 (2015).
Fei et al., "Reusable Oxidation Catalysis Using Metal-Monocatecholato Species in a Robust Metal-Organic Framework," J. Am. Chem. Soc., 136, 4965-4973 (2014).
Fendrick et al., "Manipulation of Organoactinide Coordinative Unsaturation and Stereochemistry. Properties of Chelating Bis(polymethylcyclopentadienyl) Hydrocarbyls and Hydrides," J. Organometallics, 3, 819-821 (1984).
Gascon et al., "Metal Organic Framework Catalysis: Quo vadis?," ACS Catal., 4, 361-378 (2013).
Ghebreab et al., "Intermolecular Zirconium-Catalyzed Hydrophosphination of Alkenes and Dienes with Primary Phosphines," J. Am. Chem. Soc., 136, 9240-9243 (2014).
Gonzalez et al., "Single-Crystal-to-Single-Crystal Metalation of a Metal-Organic Framework: A Route toward Structurally Well-Defined Catalysts," Inorg. Chem., 54, 2995-3005 (2015).
Gromada et al., "Group 3 metal catalysts for ethylene and α-olefin polymerization" Coord. Chem. Rev., 248, 397-410 (2004).
Hayashi et al., "Fluoride-mediated phosphination of alkenes and alkynes by silylphosphines," Tetrahedron Lett., 45, 9167-9169 (2004).

Henschel et al., "Catalytic properties of MIL-101," Chem. Commun., 4192-4194 (2008).
Hong et al., "Organolanthanide-Catalyzed Hydroamination," J. Acc. Chem. Res., 37, 673-686 (2004).
Hou et al., "Recent developments in organolanthanide polymerization catalysts," Coord. Chem. Rev., 231, 1-22 (2002).
Hudson et al., "Highly efficient iron(0) nanoparticle-catalyzed hydrogenation in water in flow," Green Chem., 15, 2141-2148 (2013).
Hwang et al., "Amine Grafting on Coordinatively Unsaturated Metal Centers of MOFs: Consequences for Catalysis and Metal Encapsulation," Angew. Chem., Int. Ed., 47, 4144-4148 (2008).
Intemann et al., "Multinuclear Magnesium Hydride Clusters: Selective Reduction and Catalytic Hydroboration of Pyridines," Organometallics, 33, 5722-5729 (2014).
Jagadeesh et al., "Nanoscale Fe2O3-Based Catalysts for Selective Hydrogenation of Nitroarenes to Anilines," Science, 342, 1073-1076 (2013).
Jeske et al., "Highly Reactive Organolanthanides. Synthesis, Chemistry, and Structures of 4f Hydrocarbyls and Hydrides with Chelating Bis(polymethylcyclopentadienyl) Ligands," J. Am. Chem. Soc., 107, 8103-8110 (1985).
Jiang et al., "Brønsted Acidity in Metal-Organic Frameworks,"Chem. Rev., 115, 6966-6997 (2015).
Johnson et al., "Industrial-Scale Synthesis and Applications of Asymmetric Hydrogenation Catalysts," Acc. Chem. Res., 40, 1291-1299 (2007).
Kelsen et al., "The use of ultrasmall iron(0) nanoparticles as catalysts for the selective hydrogenation of unsaturated C—C bonds," Chem. Commun., 49, 3416-3418 (2013).
Klet et al., "Single-Site Organozirconium Catalyst Embedded in a Metal-Organic Framework," J. Am. Chem. Soc., 137, 15680-15683 (2015).
Klet et al., "Synthetic Access to Atomically Dispersed Metals in Metal-Organic Frameworks via a Combined Atomic-Layer-Deposition-in-MOF and Metal-Exchange Approach," Chem. Mater., 28, 1213-1219 (2016).
Mokhov et al., Colloid and Nanodimensional Catalysts in Organic Synthesis: II. The Hydrogenation of Alkenes with Hydrogen at Atmospheric Pressure, Russ. J. Gen. Chem., 84, 622-628 (2014).
Molander et al., "Lanthanocene Catalysts in Selective Organic Synthesis," Chem. Rev., 102, 2161-2185 (2002).
Morris, "Exploiting Metal-Ligand Bifunctional Reactions in the Design of Iron Asymmetric Hydrogenation Catalysts," Acc. Chem. Res., 48, 1494-1502 (2015).
Müller et al., "Hydroamination: Direct Addition of Amines to Alkenes and Alkynes," Chem. Rev., 108, 3795-3892 (2008).
Nair et al., "Recent Advances in Synthetic Transformations Mediated by Cerium(IV) Ammonium Nitrate," J. Acc. Chem. Res., 37, 21-30 (2004).
Nair et al., "Cerium(IV) Ammonium Nitrate—A Versatile Single-Electron Oxidant," Chem. Rev., 107, 1862-1891 (2007).
Nakazawa et al., "Fe—H Complexes in Catalysis. In Iron Catalysis: Fundamentals and Applications," Plietker, B., Ed. Springer Berlin Heidelberg: Berlin, Heidelberg; pp. 27-81 (2011).
Oshima et al., "Regioselective Synthesis of 1,2-Dihydropyridines by Rhodium-Catalyzed Hydroboration of Pyridines," J. Am. Chem. Soc., 134, 3699-3702 (2012).
Park et al., "A versatile metal-organic framework for carbon dioxide capture and cooperative catalysis," Chem. Commun., 48, 9995-9997 (2012).
Peters et al., "Atomically Precise Growth of Catalytically Active Cobalt Sulfide on Flat Surfaces and within a Metal-Organic Framework via Atomic Layer Deposition," ACS Nano, 9, 8484-8490 (2015).
Piro et al., "The electrochemical behavior of cerium(III/IV) complexes: Thermodynamics, kinetics and applications in synthesis," Coord. Chem. Rev., 260, 21-36 (2014).
Pu et al., "A Carbon Dioxide Insertion Reaction into the Co—H Bond of Nitrogentris(triphenylphosphine)cobalt Hydride," J. Am. Chem. Soc., 90, 3896 (1968).
Rösler et al., "A Highly Active and Easily Accessible Cobalt Catalyst for Selective Hydrogenation of C=O Bonds," J. Am. Chem. Soc., 137, 7998-8001 (2015).

(56) References Cited

OTHER PUBLICATIONS

Rossi et al., "Selective Formation of Secondary Amides via the Copper-Catalyzed Cross-Coupling of Alkylboronic Acids with Primary Amides," Org. Lett., 15, 2314-2317 (2013).
Rueping et al., "Advances in catalytic metal-free reductions: from bio-inspired concepts to applications in the organocatalytic synthesis of pharmaceuticals and natural products," Green Chem., 13, 1084-1105 (2011).
Saudan, "Hydrogenation Processes in the Synthesis of Perfumery Ingredients," Acc. Chem. Res., 40, 1309-1319 (2007).
Shibasaki et al., "Lanthanide Complexes in Multifunctional Asymmetric Catalysis," N. Chem. Rev., 102, 2187-2209 (2002).
Stein et al., "Iron Nanoparticles Supported on Chemically-Derived Graphene: Catalytic Hydrogenation with Magnetic Catalyst Separation," Adv. Synth. Catal., 353, 523-527 (2011).
Sridharan et al., "Cerium(IV) Ammonium Nitrate as a Catalyst in Organic Synthesis," Chem. Rev., 110, 3805-3849 (2010).
Stalzer et al., "Single-Face/All-cis Arene Hydrogenation by a Supported Single-Site d0 Organozirconium Catalyst," Angew. Chem., Int. Ed., 55, 5263-5267 (2016).
Stout et al., "Recent Advances in the Chemistry of Dihydropyridines," Chem. Rev., 82, 223-243 (1982).
Tanabe et al., "Postsynthetic modification of metal-organic frameworks—a progress report," Chem. Soc. Rev., 40, 498-519 (2011).
Thacker et al., "Robust and Porous β-Diketiminate-Functionalized Metal-Organic Frameworks for Earth-Abundant-Metal-Catalyzed C—H Amination and Hydrogenation," J. Am. Chem. Soc., 138, 3501-3509 (2016).
Vermoortele et al., "An amino-modified Zr-terephthalate metal-organic framework as an acid-base catalyst for cross-aldol condensation," 47, 1521-1523 (2011).
Wang et al., "Postsyntetic modification of metal-organic frameworks," Chem. Soc. Rev., 38, 1315-1329 (2009).
Wang et al., "Pt Nanoparticles@Photactive Metal-Organic Frameworks: Efficient Hydrogen Evolution via Synergistic Photoexcitation and Electron Injection," J. Am. Chem. Soc., 134, 7211-7214 (2012).
Welther et al., "Iron(0) Particles: Catalytic Hydrogenations and Spectroscopic Studies," ChemCatChem, 4, 1088-1093 (2012).
Xin et al., "Access to 1,2-Dihydroisoquinolines through Gold-Catalyzed Formal [4+2] Cycloaddition," Chemistry—A European Journal, 20, 7926-7930 (2014).
Xu et al., "Acceptorless, Reversible Dehydrogenation and Hydrogenation of N-Heterocycles with a Cobalt Pincer Catalyst," ACS Catal., 5, 6350-6354 (2015).
Yoon et al., "Homochiral Metal-Organic Frameworks for Asymmetric Heterogeneous Catalysis," Chem. Rev., 112, 1196-1231 (2011).
Zhang et al., "Asymmetric Hydrogenation of Ketones Catalyzed by Zeolite-supported Gelatin-Fe Complex," Polymer. Adv. Tech., 12, 642-646 (2001).
Zhang et al., "Developing Chiral Ligands for Asymmetric Hydrogenation," Acc. Chem. Res., 40, 1278-1290 (2007).
Zhang et al., "Mild and Homogeneous Cobalt-Catalyzed Hydrogenation of C=C, C=O, and C=N Bonds," Angew. Chem. Int. Ed., 51 12102-12106 (2012).
Zhang et al., "Metal-Organic Frameworks Stabilize Solution-Inaccessible Cobalt Catalysts for Highly Efficient Broad-Scope Organic Transformations," J. Am. Chem. Soc., 138, 3241-3249 (2016).
Zhang et al., "Highly Porous Zirconium Metal-Organic Frameworks with β-UH3-like Topology Based on Elongated Tetrahedral Linkers," J. Am. Chem. Soc., 138, 8380-8383 (2016).
Zhao et al., "Solvothermal Sysnthesis of Multifunctional Coordination Polymers," Naturforsch., 65b, 976-998 (2010).
Zhao et al., "Porous Metal-Organic Frameworks for Heterogeneous Biomimetic Catalysis," Acc. Chem. Res., 47, 1199-1207 (2014).
Zheng et al., "Transfer hydrogenation with Hantzsch esters and related organic hydride donors," Chem. Soc. Rev., 41, 2498-2518 (2012).
Zhou et al., "Borylation of primary and secondary alkyl bromides catalyzed by Cu2O nanoparticles," RSC Adv., 5, 46672-46676 (2015).
Beletskaya et al., "Hydroborations catalysed by Transition Metal Complexes," Tetrahedron, vol. 53, pp. 4957-5026 (1997).
Knowles et al., "Pioneering Perspectives on Asymmetric Hydrogenation," Acc. Chem. Res., vol. 40, pp. 1238-1239 (2007).
Kobayashi et al., "Rare-Earth Metal Triflates in Organic Synthesis," Chem. Rev., vol. 102, pp. 2227-2302 (2002).
Koshti et al., "Contemporary avenues in catalytic P H bond addition reaction: A case study of hydrophosphination," Coord. Chem. Rev., vol. 265, pp. 52-73 (2014).
Kung et al., "Metal-Organic Framework Thin Films as Platforms for Atomic Layer Deposition of Cobalt Ions to Enable Elecrocatalytic Water Oxidation," ACS Appl. Mater. Interfaces, vol. 7, pp. 28223-28230 (2015).
Lagaditis et al., "Iron(II) Complexes Containing Unsymmetrical P—P—P' Pincer Ligands for the Catalytic Asymmetric Hydrogenation of Ketones and Imines," J. Am. Chem. Soc., vol. 136, pp. 1367-1380 (2014).
Langer et al., "Efficient Hydrogenation of Ketones Catalyzed by an Iron Pincer Complex," Chem., Int. Ed., vol. 123, pp. 2120-2124 (2011).
Lavilla, "Recent developments in the chemistry of dihydropyridines," J. Chem. Soc., Perkin Trans. I, pp. 1141-1156 (2002).
Leyva-Pérez et al., "Cooper(I)-catalyzed hydrophosphination of styrenes," J. Organomet. Chem., vol. 696, pp. 362-367 (2011).
Li et al., "Iron-, Cobalt-, and Nickel-Catalyzed Asymmetric Transfer Hydrogenation and Asymmetric Hydrogenation of Ketones," Acc. Chem. Res., vol. 48, pp. 2587-2598 (2015).
Li et al., "A strategy toward constructing a bifunctionalized MOF catalyst: post-synthetic modification of MOFs on organic ligands and coordinatively unsaturated metal sites," Chem. Commun. vol. 48, pp. 6151-6153 (2012).
Liu et al., "Metal-free aerobic oxidative coupling of amines to imines," Chemical Communications, vol. 47, pp. 10148-10150 (2011).
Liu et al., "Synthesis and migration insertion polymerization (MIP) of CpFe(CO)2(CH2)6PPh2 (FpC6P) for PFpC6P: macromolecule stability, degradability and redox activity," Polym. Chem., vol. 5, pp. 6702-6709 (2014).
Liu et al., "FeCl2-catalyzed hydroboration of aryl alkenes with bis(pinacolato)diboron," J. RSC Adv., vol. 5, pp. 73705-73713 (2015).
Mallat et al., "Asymmetric Catalysis at Chiral Metal Surfaces," Chem. Rev., vol. 107, pp. 4863-4890 (2007).
Manna et al., "Postsynthetic Metalation of Bipyridyl-Containing Metal-Organic Frameworks for Highly Efficient Catalytic Organic Transformations," J. Am. Chem. Soc., vol. 136, pp. 6566-6569 (2014).
Manna et al., "Bipyridine- and Phenanthroline-Based Metal-Organic Frameworks for Highly Efficient and Tandem Catalytic Organic Transformations via Directed C—H Activation," J. Am. Chem. Soc., vol. 137, pp. 2665-2673 (2015).
Manna et al., "Metal-Organic Framework Nodes Support Single-Site Magnesium-Alkyl Catalysts for Hydroboration and Hydroamination Reactions," J. Am. Chem. Soc., vol. 138, pp. 7488-7491 (2016).
McGuirk et al., "Turning on Catalysis: Incorporation of a Hydrogen-Bond-Donating Squaramide Moiety into a Zr Metal-Organic Framework," J. Am. Chem. Soc., vol. 137, pp. 919-925 (2015).
Metzger et al., "Selective Dimerization of Ethylene to 1-Butene with a Porous Catalyst," ACS Cent. Sci., vol. 2, pp. 148-153 (2016).
Mikhailine et al., "Efficient Asymmetric Transfer Hydrogenation of Ketones Catalyzed by an Iron Complex Containing a P—N—N—P Tetradentate Ligand Formed by Template Synthesis," J. Am. Chem. Soc., 131, 1394-1395 (2009).

* cited by examiner

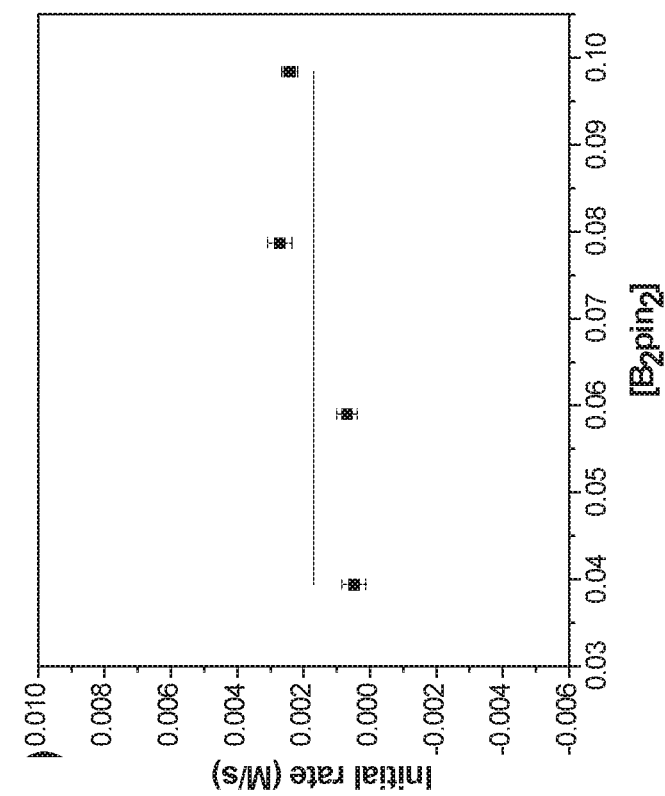
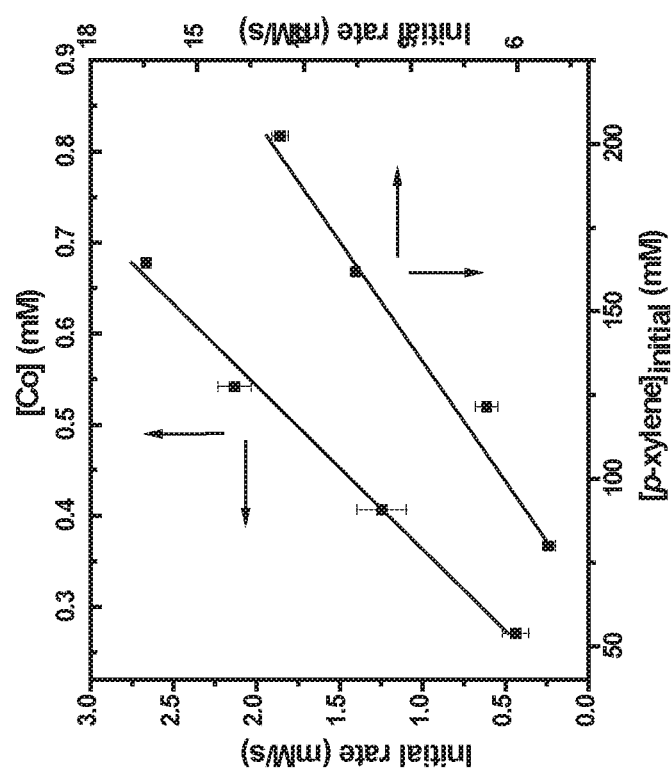
Fig. 5B
Fig. 5A

STABILIZATION OF ACTIVE METAL CATALYSTS AT METAL-ORGANIC FRAMEWORK NODES FOR HIGHLY EFFICIENT ORGANIC TRANSFORMATIONS

RELATED APPLICATIONS

The presently disclosed subject matter claims the benefit of U.S. Provisional Patent Application Ser. No. 62/240,178, filed Oct. 12, 2015; and U.S. Provisional Patent Application Ser. No. 62/380,784, filed Aug. 29, 2016, the disclosures of each of which are incorporated herein by reference in their entireties.

STATEMENT OF GOVERNMENT SUPPORT

This invention was made with government support under Grant No. CHE-1464941 from the National Science Foundation. The government may have certain rights to this invention.

TECHNICAL FIELD

The presently disclosed subject matter relates to metal-organic framework (MOF) materials containing various secondary building units (SBUs) and bridging ligands, wherein the MOF SBUs contain a catalytically active metal, their preparation, and their use as solid catalysts for organic transformations, such as the regioselective borylation and silylation of benzylic C—H bonds, the hydrogenation of alkenes, imines, carbonyls, nitroarenes, and heterocycles, hydroboration, hydrophosphination, and cyclization reactions. More particularly, the MOFs can comprise SBUs containing a first metal and a catalytically active second metal complexed to an SBU oxygen atom.

ABBREVIATIONS

A=angstrom
° C.=degrees Celsius
%=percentage
µL=microliter
µmol=micromole
atm=atmosphere
BTC=trimesic acid
Co=cobalt
Cr=chromium
Cu=copper
d=day
DMF=dimethylformamide
DMSO=dimethylsulfoxide
EtOH=ethanol
EXFAS=extended x-ray absorption fine structure
Fe=iron
g=gram
GC=gas chromatography
h=hour
ICP-MS=inductively coupled plasma-mass spectrometry
kg=kilogram
M=molar
mg=milligram
Mg=magnesium
Me=methyl
min=minute
mL=milliliter
mM=millimolar
mmol=millimole
Mn=manganese
MOF=metal-organic framework
mol=mol
MTBC=methane tetrakis(p-biphenylcarboxylate)
nBuLi (or n-BuLi)=n-butyl lithium
Ni=nickel
nm=nanometer
NMR=nuclear magnetic resonance
pin=pinacolate
Ph=phenyl
PXRD=power x-ray diffraction
r.t. (or rt)=room temperature
SBU=secondary building unit
TFA=trifluoroacetic acid
TGA=thermogravimetric analysis
TLC=thin layer chromatography
TON=turnover number
TPDC=p,p'-terphenyldicarboxylic acid
TPHN=4,4'-bis(carboxyphenyl)-2-nitro-1,1'-biphenyl
XAFS=x-ray absorption fine structure spectroscopy
XANES=x-ray absorption near edge structure
Zr=zirconium
Hf=hafnium

BACKGROUND

For decades, many organic transformations, such as hydrogenation reactions, have relied on precious metal catalysts. However, the low abundance, high price, and inherent toxicity of precious metals have led to intense interest in developing earth-abundant metal catalysts. See Chirik et al., Acc. Chem. Res., 2015, 48, 2495. Significant progress has been made in recent years on the development of base metal catalysts. For example, single-site hydrogenation catalysts based on iron, cobalt, nickel, or copper coordinated with sterically encumbered strong field nitrogen- or phosphorus-donor ligands have been reported. See for example, Bart et al., J. Am. Chem. Soc., 2004, 126, 13794-13807. However, each of these homogeneous base metal catalysts typically only hydrogenates a narrow class of substrates with limited turnover numbers. Furthermore, few examples of earth-abundant metal catalyzed hydrogenation reactions of imines and heterocycles exist and they generally require harsh reaction conditions. See Chen et al., J. Am. Chem. Soc., 2015, 137, 11718-11724; and Zhanaq et al., Angew. Chem. Int. Ed., 2012, 51, 12102-12106.

Homogeneous base metal catalysts typically rely on coordination of sterically bulky chelating ligands to prevent the formation of catalytically incompetent oligomeric species by shutting down the intermolecular decomposition pathways. Such steric protection is important for stabilizing weak-field ligand-coordinated metal catalysts, particularly for late first-row transition metals in a very weak field coordination environment consisting of oxygen-donor atoms. See Bellow et al., Organometallics, 2015, 34, 2917-2923. However, steric protecting groups often weaken metal-ligand binding and impede catalytic activity by preventing challenging hydrogenation substrates, such as tri- and tetra-substituted olefins, from accessing the catalytic sites. See Crabtree, Acc. Chem. Res., 1979, 12,331-337. Immobilization of catalytic species in structurally regular porous solid supports can provide catalytic site isolation without relying on bulky ligands, thus offering an alternative route to obtaining highly active base metal catalysts. Significant efforts have been devoted to the development of zeolite-, silica- or graphene-supported iron- and cobalt-based heterogeneous hydrogenation catalysts (see, e.g., Chen et al., J. Am. Chem. Soc., 2015, 137, 11718-11724) and bare or protected metallic nanoparticles-based catalysts. See Stein et al., Adv. Synth. Catal., 2011, 353, 523-527; Welther et al., ChemCatChem, 2012, 4, 1088-1093; Hudson et al., Green Chem., 2013, 15, 2141-2148; Kelsen et al., Chem. Commun., 2013, 49, 3416-3418; and Mokhov et al., Russ. J. Gen. Chem., 2014, 84, 622-628. However, the activities and lifetimes of these heterogeneous hydrogenation catalysts can still be unsatisfactory.

Metal-organic frameworks (MOFs) are an emerging class of porous molecular materials (see Moulton et al., Chem. Rev., 2001, 101, 1629; Evans et al., Acc. Chem. Res., 2002, 35, 511; Lan et al., Angew. Chem., Int. Ed., 2009, 48, 2334; Uemura et al., Chem. Soc. Rev., 2009, 38, 1228; Das et al., Angew. Chem., Int. Ed., 2011, 50, 10510; Wiers et al., J. Am. Chem. Soc., 2011, 133, 14522; Kreno et al., Chem. Rev., 2012, 112, 1105; Li et al., Chem. Rev., 2012, 112, 869; Furukawa et al., Science, 2013, 341; and Shustova et al., J. Am. Chem. Soc., 2013, 135, 13326) assembled from organic linkers and metal ions or metal cluster nodes. They find application in gas storage (e.g., hydrogen, carbon dioxide, and methane storage), molecule separation, and drug delivery. MOFs can also provide a highly tunable platform to engineer heterogeneous catalysts for chemical reactions, including asymmetric organic transformations and/or transformations that cannot be achieved with traditional porous inorganic materials. See Kesanli et al., Coord. Chem. Rev., 2003, 246, 305.

However, there remains an ongoing need in the art for additional heterogeneous catalysts for catalysis. In particular, there is an ongoing need for additional catalysts that have good stability and recyclability. There is an ongoing need for additional heterogeneous catalysts that can catalyze reactions at low catalyst loadings, with high turnover and good yields. Further, there is a need for additional heterogeneous catalysts to catalyze additional types of reactions and/or reactions of additional types of substrates.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Disclosed herein in some embodiments is a method for preparing a catalyst, said method comprising: providing a metal-organic framework (MOF), wherein the MOF comprises a secondary building unit (SBU) comprising a terminal or bridging OH or $OH_2$ group; and reacting the MOF with a catalyst precursor, wherein the catalyst precursor is a compound of the formula $ML_nX$, wherein X is a halide, H, alkyl or aryl group, M is a catalytically active metal, n is an integer from 0 to 5, and each L is independently selected from the group comprising H, a halide, an alkyl group, an aralkyl group, an aryl group, a heteroaryl group, an alkoxy group, and an amine, thereby forming a catalyst comprising a —$OML_n$ group or a —$(OH)ML_n$ group.

In some embodiments, the SBU is selected from the group comprising Zr-oxo clusters, Hf-oxo clusters, Zn-oxo clusters, Ti-oxo clusters, Al-oxo clusters, Cu-carboxylate paddlewheels, and Ce-oxo clusters. In some embodiments, the MOF comprises a plurality of SBUs, optionally wherein each of the SBUs comprises at least one terminal or bridging OH or $OH_2$ group.

In some embodiments, the MOF further comprises an organic bridging ligand substituted with one or more carboxylate, pyridine, and/or phosphonate moieties, optionally wherein the organic bridging ligand is a dicarboxylate, a tricarboxylate, or a tetracarboxylate. In some embodiments, the organic bridging ligand comprises one or more aryl or arylene groups, optionally wherein the organic bridging ligand is selected from the group comprising 1,4-bis(4-carboxyphenyl)benzene, p,p'-terphenyldicarboxylic acid (TPDC), methane tetrakis(p-biphenylcarboxylate) (MTBC), trimesic acid (BTC), 4,4'-bis(carboxyphenyl)-2-nitro-1,1'-biphenyl (TPHN), and 1,1'-biphenyl-4,4'-dicarboxylate.

In some embodiments, M is selected from the group comprising Mg, Zr, Hf, V, Fe, Co, Cr, Mn, Ni, and Cu. In some embodiments, the catalyst precursor is selected from $CoCl_2$, $Me_2Mg$, $Zr(CH_2Ph)_4$, and $FeBr_2$.

In some embodiments, the MOF is reacted with a base prior to reaction with the catalyst precursor, optionally wherein the base is a salt of a Group 1 element and a carbanion, amide or hydride, further optionally wherein the base is n-butyl lithium (nBuLi) or trimethylsilylmethyllithium ($LiCH_2SiMe_3$).

In some embodiments, the presently disclosed subject matter provides a catalyst prepared by a method comprising: providing a MOF, wherein the MOF comprises a SBU comprising a terminal or bridging OH or $OH_2$ group; and reacting the MOF with a catalyst precursor, wherein the catalyst precursor is a compound of the formula $ML_nX$, wherein X is a halide, H, alkyl or aryl group, M is a catalytically active metal, n is an integer from 0 to 5, and each L is independently selected from the group comprising H, a halide, an alkyl group, an aralkyl group, an aryl group, a heteroaryl group, an alkoxy group, and an amine, thereby forming a catalyst comprising a —$OML_n$ group or a —$(OH)ML_n$ group.

In some embodiments, the presently disclosed subject matter provides a method for preparing a catalyst, said method comprising: providing a MOF, wherein the MOF comprises a SBU comprising a metal and a terminal or bridging OH or $OH_2$ group; and reacting the MOF with a base to form a deprotonated SBU; and reacting the deprotonated SBU with a catalyst precursor comprising a catalytically active metal or with a reducing agent to reduce a metal in the deprotonated SBU into a catalytically active metal.

In some embodiments, the SBU is selected from the group comprising Zr-oxo clusters, Hf-oxo clusters, Zn-oxo clusters, Ti-oxo clusters, Al-oxo clusters, Cu-carboxylate paddlewheels, and Ce-oxo clusters. In some embodiments, the MOF comprises a plurality of SBUs comprising at least one terminal or bridging OH or $OH_2$ group, optionally wherein each of the SBUs comprises at least one terminal or bridging OH or $OH_2$ group, and wherein reacting the MOF with a base deprotonates all or a portion of the SBUs.

In some embodiments, the MOF further comprises an organic bridging ligand substituted with one or more carboxylate, pyridine, and/or phosphonate moieties, optionally wherein the organic bridging ligand is a dicarboxylate, a tricarboxylate, or a tetracarboxylate. In some embodiments, the organic bridging ligand comprises one or more aryl or arylene groups, optionally wherein the organic bridging ligand is selected from the group comprising 1,4-bis(4- carboxyphenyl)benzene, TPDC, MTBC, BTC, TPHN, and 1,1'-biphenyl-4,4'-dicarboxylate.

In some embodiments, the base is a salt of a Group 1 element and a carbanion, amide or hydride, optionally wherein the base is nBuLi or LiCH$_2$SiMe$_3$. In some embodiments, the deprotonated SBU is reacted with a catalyst precursor wherein the catalyst precursor is a compound of the formula ML$_n$X, wherein M is a catalytically active metal, n is an integer between 0 and 5, X is a halide, H, alkyl or aryl group, and each L is independently selected from the group comprising H, halide, an alkyl group, an aralkyl group, an aryl group, a heteroaryl group, an alkoxy group, and an amine. In some embodiments, M is selected from the group comprising Mg, Zr, Hf, V, Fe, Co, Cr, Mn, Ni, and Cu. In some embodiments, the catalyst precursor is selected from CoCl$_2$, Me$_2$Mg, Zr(CH$_2$Ph)$_4$, and FeBr$_2$.

In some embodiments, the deprotonated SBU is reacted with a reducing agent, optionally wherein the reducing agent is a borane, further optionally wherein the reducing agent is pinacolborane. In some embodiments, the SBU comprises a Ce-oxo cluster, optionally wherein the MOF further comprises a trimesic acid organic bridging ligand.

In some embodiments, the presently disclosed subject matter provides a catalyst prepared according to a method comprising: providing a MOF, wherein the MOF comprises a SBU comprising a metal and a terminal or bridging OH or OH$_2$ group; and reacting the MOF with a base to form a deprotonated SBU; and reacting the deprotonated SBU with a catalyst precursor comprising a catalytically active metal or with a reducing agent to reduce a metal in the deprotonated SBU into a catalytically active metal.

In some embodiments, the presently disclosed subject matter provides a MOF comprising a SBU comprising one or more —OM'L$_x$ and/or —(OH)M'L$_x$ groups, wherein M' is a metal, x is an integer between 0 and 5, and each L is independently selected from the group comprising H, a halide, an alkyl group, an aralkyl group, an aryl group, a heteroaryl group, an alkoxy group, and an amine, optionally wherein the O or OH of the —OM'L$_x$ or —(OH)M'L$_x$ group is a metalated terminal oxo group, a metalated oxygen from a deprotonated μ-OH group, a metalated terminal OH group, or a metalated bound water group.

In some embodiments, the metal is free of decomposition due to disproportionation. In some embodiments, M' is selected from Li, Mg, Fe, Co, Cr, Mn, Ni, and Cu, optionally wherein M' is a catalytically active metal selected from Co, Fe, Cu and Mg.

In some embodiments, the MOF comprises a second metal selected from Zr, Hf, Zn, Ti and Ce. In some embodiments, the SBU is derived from a Zr-oxo cluster, a Hf-oxo cluster, a Zn-oxo cluster, a Ti-oxo cluster, an Al-oxo cluster, a Cu-carboxylate paddlewheel, or a Ce-oxo cluster, optionally wherein the SBU is derived from a cubic or octahedral metal oxo cluster, further optionally wherein the cubic or octahedral metal oxo cluster is of the formula Zr(μ$_2$-O)$_8$(μ$_2$-OH)$_4$ or Zr$_6$(μ$_3$-O)$_4$(μ$_3$-OH)$_4$.

In some embodiments, the MOF further comprises an organic bridging ligand substituted with one or more carboxylate, pyridine, and/or phosphonate moieties, optionally wherein the organic bridging ligand is a dicarboxylate, a tricarboxylate, or a tetracarboxylate. In some embodiments, the organic bridging ligand further comprises one or more aryl or arylene groups, optionally wherein the organic bridging ligand is selected from the group comprising 1,4-bis(4-carboxyphenyl)benzene, TPDC, MTBC, BTC, TPHN, and 1,1'-biphenyl-4,4'-dicarboxylate. In some embodiments, the organic bridging ligand is a tetrahedral bridging ligand, optionally MTBC.

In some embodiments, the MOF comprises a plurality of SBUs comprising one or more —OM'L$_x$ and/or —(OH)M'L$_x$ groups, optionally wherein each SBU comprises between 1 and 4 —OM'L$_x$ and/or —(OH)M'L$_x$ groups. In some embodiments, the MOF has the formula Zr$_6$O$_4$(OH$_{4-n}$)(OM'X)$_n$(O$_2$CR)$_{12}$, wherein n is an integer between 0 and 4, M' is Co, Fe, Cu or Mg, and R is an arylene group. In some embodiments, the SBU has the formula Ce$^{III}_6$(μ$_3$-O)$_4$(μ$_3$-OLi)$_4$(H)$_6$(THF)$_6$. In some embodiments, MOF is crystalline and/or porous.

In some embodiments, the presently disclosed subject matter provides a method for preparing a compound comprising contacting a substrate capable of forming a product by catalytic transformation with a heterogeneous catalyst prepared according to one of the presently disclosed methods or an MOF comprising a SBU comprising one or more —OM'L$_x$ and/or —(OH)M'L$_x$ groups, wherein M' is a metal, x is an integer between 0 and 5, and each L is independently selected from the group comprising H, a halide, an alkyl group, an aryl group, a heteroaryl group, an alkoxy group, and an amine. In some embodiments, the catalytic transformation is selected from the group comprising ethylene oligomerization, alkyne coupling, hydromethylation, alkane dehydrosilation, alkane metathesis, dehydrogenative alkyl C—H phosphination, pyridine functionalization, dehydrocoupling, hydrosilation of olefins, ketones and aldehydes, oxidation of primary alcohols, hydroamination, hydroformylation, C—H borylation, hydrogenation of alkenes, imines, carbonyls, nitroarenes, and heterocycles, hydroboration, hydrophosphination, and C—H amination. In some embodiments, the catalytic transformation is conducted in a batch reactor, a flow reactor, or in a supercritical fluid reactor.

Accordingly, it is an object of the presently disclosed subject matter to provide metal-organic framework (MOFs) materials comprising a SBU with a metalated terminal oxo group, a metalated oxygen from a deprotonated μ-OH group, a metalated terminal OH group, or a metalated bound water group, wherein the metal of the metalated group is a catalytically active metal, such as Co, Fe, Cu and Mg, or wherein the SBU otherwise comprises a catalytically active metal; methods of preparing the MOFs, and methods of using the MOFs as catalysts. This and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). A further understanding of the presently disclosed subject matter can be obtained by reference to an embodiment set forth in the illustrations of the accompanying drawings. Although the illustrated embodiment is merely exemplary of the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which:

FIG. 5A is a graph showing the kinetic plots of initial rates (d[p-xylene]/dt) for benzylic C—H borylation of p-xylene versus catalyst concentration ([Co], millimolar (mM)) and initial p-xylene concentration ([p-xylene]$_{initial}$, mM) for the first 12 hours, showing first-order dependence on both components.

FIG. 5B is a graph showing a plot of the initial rate (d[p-xylene/dt) versus initial concentration of pinacolborane ($B_2pin_2$) [$B_2pin_2$] for the first 12 hours (<10% conversion) showing the independence of initial rates on the $B_2pin_2$ concentrations. The catalyst concentration was $2.0 \times 10^{-4}$ molar (M) and the concentration of p-xylene was $3.41 \times 10^{-1}$ M.

DETAILED DESCRIPTION

Figure 2A:
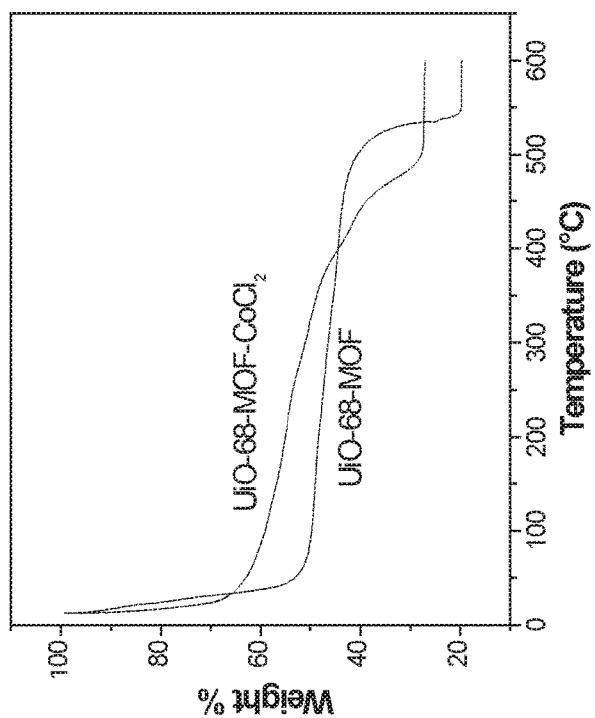
FIG. 2A is a graph showing the thermogravimetric analysis (TGA) curves for the freshly prepared metal organic framework (MOF) described for FIG. 1 (UiO-68-MOF) and the same MOF after metalation of the secondary building units with cobalt chloride (UiO-68-CoCl) in the 25-600 degrees Celsius (° C.) range.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example±20% or ±10%, in another example±5%, in another example±1%, and in still another example±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "arene" refers to an aromatic compound.

The term "olefin" refers to a compound with a carbon-carbon double bond.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "amine" refers to compounds or ligands for metals having the formula $N(R)_3$ wherein each R is independently H, alkyl, substituted alkyl, aryl, substituted aryl, aralkyl, or substituted aralkyl.

The terms "halo", "halide", or "halogen" as used herein refer to fluoro, chloro, bromo, and iodo groups.

The terms "hydroxyl" and "hydroxyl" refer to the —OH group.

The term "alkoxy" refers to the —OR group, where R is alkyl or substituted alkyl.

The term "aryloxy" refers to the —OR group where R is aryl or substituted aryl.

The terms "mercapto" or "thiol" refer to the —SH group.

The terms "carboxylate" and "carboxylic acid" can refer to the groups —C(=O)O⁻ and —C(=O)OH, respectively. In some embodiments, "carboxylate" can refer to either the —C(=O)O⁻ or —C(=O)OH group.

The term "phosphonate" refers to the —P(=O)(OR)$_2$ group, wherein each R can be independently H, alkyl, substituted alkyl, aralkyl, substituted aralkyl, aryl, substituted aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "silyl" refers to groups comprising silicon atoms (Si).

The term "pyridine" refers to a compound or chemical moiety that comprises a heteroaryl group with a six-membered backbone, wherein the six-membered backbone comprises five carbon atoms and one nitrogen atom. The pyridine can optionally be substituted by one or more aryl group substituents.

As used herein, the term "metal-organic matrix material" refers to a solid material comprising both metal and organic components, wherein the organic components include at least one, and typically more than one carbon atom. In some embodiments, the material is crystalline. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate) organic ligand. In some embodiments, the material contains more than one type of metal ion. In some embodiments, the material can contain more than one type of organic bridging ligand.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —CO$_2$H, —NO$_2$, amino, hydroxyl, thio, thioalkyl, —B(OH)$_2$, —SO$_3$H, PO$_3$H, phosphonate, and heteroatoms (e.g., nitrogen, oxygen, or sulfur) in heterocycles. In some embodiments, in addition to binding to at least two metal ions or complexes in an MOF, the bridging ligand can also bind to a further metal ion or complex, e.g., to provide a catalytic moiety.

As used herein, turnover number (TON) refers to the number of moles of substrate that a mole of catalyst can convert before being inactivated.

As used herein, the term "stable" refers to a characteristic of a MOF of the presently disclosed subject matter. A "stable" MOF refers to a MOF that retains its framework structure during the catalytic reaction; such stability can be manifested by the retention of the powder X-ray diffraction pattern after the catalytic reaction. In some embodiments, the term "stable" refers to the characteristic that the MOF does not leach metal to a measurable extent, e.g., during a catalytic reaction. In some embodiments, the term "stable" refers to the characteristic that the MOF comprises a O-metal bond that is stable wherein the O-metal bond is present in a SBU of a MOF, but would disproportionate if not present in the MOF.

II. Metal-Organic Framework (MOF) Catalysts and their Preparation

Metal-organic frameworks (MOFs), constructed from periodic repeats of metal cluster secondary building units (SBUs) and organic linkers, can be used as tunable porous supports for single site catalysts for various organic transformations. The present disclosed subject matter provides metal-organic frameworks (MOFs) comprising various secondary building units (SBUs) that have been post-synthetically modified, e.g., via metalation of an oxygen atom with a catalytically active metal or via changing the oxidation state of a metal already present in the SBU, to provide a catalyst. The MOF framework isolates the catalytic sites from each other, leading to much enhanced catalyst stability, which allows the use of first-row metal catalysts for a number of reactions that are typically catalyzed by precious metal catalysts. MOF frameworks disclosed herein thus allow the transition from precious metal catalysis to base metal catalysis. Further, the synthetic tunability of the MOFs can provide the ability to fine tune the electronic and steric properties of the catalyst sites, whereas the structure regularity and catalytic site homogeneity of the MOFs can facilitate mechanistic studies of reactions catalyzed by the MOFs.

In some embodiments, a MOF catalyst of the presently disclosed subject matter can be prepared by simple post-synthetic metalation of a MOF's SBUs that contain —OH and/or —OH$_2$ groups using metal precursors (such as Mg, Fe, Co, Cr, Mn, Ni and Cu complexes) to afford highly active single-site solid catalysts for organic transformations. The SBU-functionalized MOFs can possess highly electron deficient and coordinatively unsaturated metal centers which can catalyze organic reactions via, for example, σ-bond metathesis pathways. In some embodiments, these MOF-based catalysts do not have homogeneous counterparts. The MOFs provide a versatile family of single-site solid catalysts for catalyzing a broad scope of organic transformations, including regioselective borylation and silylation of benzylic C—H bonds as well as hydrogenation, hydroboration and hydrosilylation of olefins and ketones. The solid catalysts can also be integrated into a flow reactor or a supercritical fluid reactor to enable green manufacturing of fine chemicals.

In some embodiments, the presently disclosed subject matter provides a MOF comprising a SBU comprising one or more —OM'L$_x$ and/or —(OH)M'L$_x$ groups, wherein M' is a metal, x is an integer between 0 and 5, and each L is independently selected from the group consisting of H, a halide, an alkyl group, an aralkyl group, an aryl group, a heteroaryl group, an alkoxy group, and an amine. In some embodiments, the O or OH of the —OM'L$_x$ or —(OH)M'L$_x$ group is a metalated terminal oxo group, a metalated oxygen from a deprotonated μ-OH group, a metalated terminal OH group, or a metalated bound water group. In some embodiments, L is selected from halide (e.g., Cl or Br) and alkyl (e.g., methyl or ethyl). In some embodiments, L is benzyl (—CH$_2$Ph).

In some embodiments, the metal, M', is stabilized in the MOF, for example, such that it is free of decomposition due to disproportionation. The metal M' can be any suitable metal. In some embodiments, M' is a catalytically active and/or base metal (e.g., magnesium (Mg), zirconium (Zr), hafnium (Hf), vanadium (V), iron (Fe), cobalt (Co), lead (Pb), nickel (Ni), manganese (Mn) or Zinc (Zn)). In some embodiments, M' is a Group 1 metal, e.g., lithium (Li), sodium (Na), or potassium (K). In some embodiments, M' is selected from Li, Mg, Fe, Co, Cr, Mn, Ni, and Cu. In some embodiments, M' is a catalytically active metal. In some embodiments, M' is Co, Fe, Cu or Mg. In some embodiments, M' is Li.

As described hereinabove, the presently disclosed MOF catalysts are based on MOFs that contain SBUs that can be metalated. For example, the parent MOF can contain a SBU with a metal-OH or metal-OH$_2$ bond. Exemplary MOFs with metal-OH— or metal-OH$_2$-containing SBUs that can be metallated include, but are not limited to: UiO series, Zr$_6$O$_4$(OH)$_4$L$_6$; MOF-808, Zr$_6$O$_4$(OH)$_4$(HCOO)$_6$L$_2$; PCN-222, Zr$_6$O$_4$(OH)$_8$(H$_2$O)$_4$L$_2$; CAU-8, Al(OH)L, MIL-53, Fe$_3$OL$_3$(H$_2$O)$_2$Cl, POST-1, Zn$_3$OL$_3$(H$_2$O)$_3$; MIL-101, Fe$_3$OL$_3$(H$_2$O)Cl; MIL-68, In(OH)L$_2$; Cerium MOF series, Ce$_6$O$_4$(OH)$_4$L$_6$; STAM-1, Cu(H$_2$O)L; SNU-30, Zn$_2$L$_2$(H$_2$O)$_2$; CAU-1, Al$_4$(OH)$_2$(OCH$_3$)$_4$L$_3$; and HKUST-1, Cu$_3$L$_2$(H$_2$O)$_3$.

Thus, the presently disclosed MOF is derived from a MOF (i.e., a "parent" MOF) containing a SBU already comprising a metal cluster, and therefore can contain another (or second) metal, i.e., in addition to M'. Thus, for example, the presently disclosed MOF can comprise a second metal, such as but not limited to, Zr, Hf, Ti, Zn, Al, Fe, Cu, Co, Ru, Cr, Ga, In, and Ce. In some embodiments, the second metal is selected from Zr, Hf, Ti, Zn, and Ce. In some embodiments, M' is the same metal as the metal in the parent MOF SBUs.

The MOF can comprise any suitable SBU or mixture of SBUs. In some embodiments, the SBU is derived from (i.e., is a M' metalated version of) a Zr-oxo cluster, a Hf-oxo cluster, a Zn-oxo cluster, a Ti-oxo cluster, an Al-oxo cluster, a Cu-carboxylate paddlewheel, or a Ce-oxo cluster. In some embodiments, the SBU is derived from a cubic or octahedral metal oxo cluster. In some embodiments, the cubic or octahedral metal oxo cluster is of the formula Zr$_8$(μ$_2$-O)$_8$(μ$_2$-OH)$_4$ or Zr$_6$(μ$_3$-O)$_4$(μ$_3$-OH)$_4$. Additional exemplary SBUs that can be metalated are show in Scheme 1, below.

Scheme 1. Additional Exemplary Secondary Building Units.

M$^{4+}$ Hydroxyl Clusters

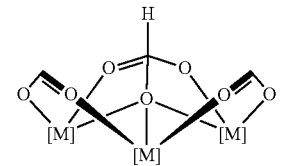

M$_6$O$_4$(OH)$_4$ with 6, 8, or 12 carboxylates
M = Zr$^{4+}$, Hf$^{4+}$, Ce$^{4+}$

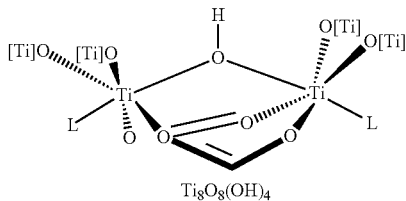

Ti$_8$O$_8$(OH)$_4$

M$^{3+}$ Hydroxyl Clusters

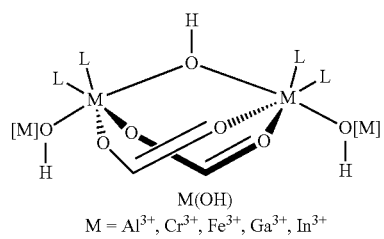

M(OH)
M = Al$^{3+}$, Cr$^{3+}$, Fe$^{3+}$, Ga$^{3+}$, In$^{3+}$

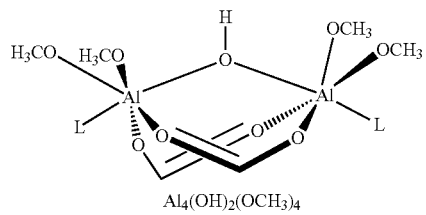

Al$_4$(OH)$_2$(OCH$_3$)$_4$

M$^{2+}$/M$^{3+}$ Aqua Clusters

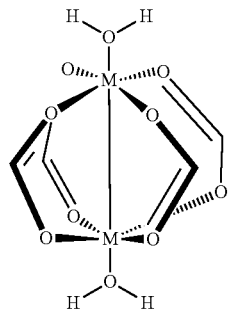

M$_2$(H$_2$O)$_2$
M = Cu$^{2+}$, Zn$^{2+}$, Fe$^{2+}$,
Co$^{2+}$, Ru$^{2+}$

-continued

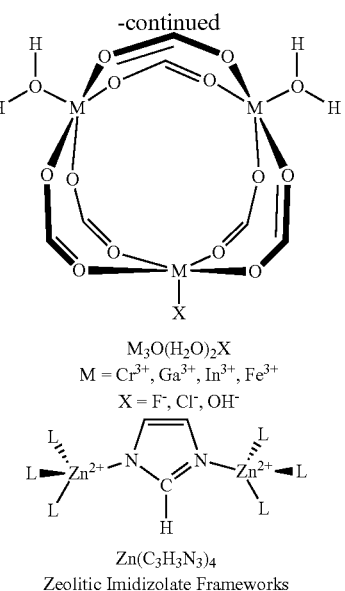

$M_3O(H_2O)_2X$
$M = Cr^{3+}, Ga^{3+}, In^{3+}, Fe^{3+}$
$X = F^-, Cl^-, OH^-$ $Zn(C_3H_3N_3)_4$
Zeolitic Imidizolate Frameworks The MOF can comprise any suitable organic bridging ligand. The organic bridging ligand can comprise chemical moieties that can bond (e.g., coordinatively bond) to the metal containing SBUs. Thus, in some embodiments, the organic bridging ligand is substituted (or derivatized) with one or more groups that include a moiety, such as, but not limited to, a carboxylate or carboxylic acid, an ester, an amide, a pyridine or other nitrogen containing aromatic group, an amine (including nitrogen-containing heterocycles), a hydroxyl, a thiol, a thioalkyl, —B(OH)$_2$, —SO$_3$H, —PO$_3$H, —NO$_2$, or a phosphonate. In some embodiments, the organic bridging ligand comprises one or more carboxylate, pyridine, and/or phosphonate moieties that can coordinate to a metal ion in the SBU. In some embodiments, the organic briding ligand is a carboxylate, e.g., dicarboxylate, a tricarboxylate, or a tetracarboxylate.

The groups (e.g., the carboxylate, pyridine and/or phosphonate groups) that can bond to the SBU metal ion can be substituted on an alkyl, alkylene, aryl, or arylene group. In some embodiments, they are substituted on an aryl or arylene group and, therefore, the organic briding ligand can comprise an aryl or arylene group. In some embodiments, the arylene group can comprise a plurality of phenylene groups, optionally substituted with one or more aryl group substituents in addition to the groups used to coordinate to the metal of the SBU. In some embodiments, the organic bridging ligand is selected from the group comprising 1,4-bis(4-carboxyphenyl)benzene, p,p'-terphenyldicarboxylic acid (TPDC), methane tetrakis(p-biphenylcarboxylate) (MTBC), trimesic acid (BTC), 4,4'-bis(carboxyphenyl)-2-nitro-1,1'-biphenyl (TPHN), and 1,1'-biphenyl-4,4'-dicarboxylate. In some embodiments, the MOF is free of a chiral organic bridging ligand and/or a nitrogen-donor containing organic bridging ligand (such as a pyridine-containing bridging ligand).

In some embodiments, the organic bridging ligand (e.g., 1,4-bis(4-carboxyphenyl)benzene) can have a planar geometry. In some embodiments, the organic bridging ligand can have a tetrahedral geometry. For example, the MTBC ligand has a tetrahedral geometry. In some embodiments, the MOFs can contain a mixture of two or more different organic bridging ligands.

In some embodiments, the MOF can comprise a plurality of SBUs comprising one or more —OM'L$_x$ and/or —(OH)M'L$_x$ groups. In some embodiments, more than 50%, more than 75% or more than 95% of the SBUs of the MOF comprise one or more —OM'L$_x$ and/or —(OH)M'L$_x$ groups. In some embodiments, essentially 100% of the SBUs of the MOF comprise one or more —OM'L$_x$ and/or —(OH)M'L$_x$ groups.

In some embodiments, each SBU comprises between 1 and 4 —OM'L$_x$ and/or —(OH)M'L$_x$ groups. For example, each SBU can comprise 1, 2, 3, or 4 —OM'L$_x$ and/or —(OH)M'L$_x$ groups.

In some embodiments, the MOF comprises one or more Zr oxo clusters. In some embodiments, the MOF has the formula $Zr_6O_4(OH_{4-n})(OM'X)_n(O_2CR)_{12}$, wherein n is an integer between 0 and 4, M' is Co, Fe, Cu or Mg, and R is an arylene group.

In some embodiments, M' is a Group I element. In some embodiments, the SBU has the formula $Ce^{III}_6(\mu_3\text{-}O)_4(\mu_3\text{-}OLi)_4(H)_6(THF)_6$.

In some embodiments, the MOF is crystalline and/or porous. For example, the MOF can comprise internal pores, cavities, and open channels to transport organic substrates and products in and out of the MOF. In some embodiments, the particle sizes of the MOFs can be tuned to minimize the diffusion distance needed for the organic substrates and products to maximize the catalytic turnover frequency and total catalytic turnover number.

In some embodiments the presently disclosed subject matter provides uses of the presently disclosed MOFs in catalyzing organic reactions such as but not limited to the catalytic organic reactions shown in Scheme 2, below, or other related reactions in a batch mode, in conventional solvents, or in the absence of solvents, or in unconventional solvents, such as supercritical carbon dioxide. In some embodiments the presently disclosed subject matter provides uses of the MOFs for catalyzing organic reactions shown in Scheme 2 or other related reactions in a flow reactor. In some embodiments the presently disclosed subject matter provides for the use of the MOFs to catalyze sequential or multistep reactions.

In some embodiments, the presently disclosed subject matter provides methods of preparing catalysts (i.e., MOF-based catalysts) for various chemical transformations. These methods can comprise post-synthetic modification (e.g., via metalation and/or metal ion reduction or oxidation) of an MOF.

In some embodiments, the presently disclosed subject matter provides a method for preparing a catalyst, said method comprising: providing a MOF, wherein the MOF comprises a SBU comprising a terminal or bridging OH or OH$_2$ group; and reacting the MOF with a catalyst precursor, wherein the catalyst precursor is a compound of the formula ML$_n$X, wherein X is a halide, H, alkyl or aryl group, M is a catalytically active metal, n is an integer from 0 to 5, and each L is independently selected from the group comprising H, a halide, an alkyl group, an aralkyl group, an aryl group, a heteroaryl group, an alkoxy group, and an amine, thereby forming a catalyst comprising a —OML$_n$ group or a —(OH)ML$_n$ group.

Typical MOF synthesis involves heating a mixture of metal ions or complexes and organic bridging ligands (or their precursors) to organic bridging ligands in appropriate solvent mixtures (such as dimethylformamide (DMF), diethylformamide, or others). In some instances, various amounts of acids, such as trifluoroacetic acid (TFA), are added to the reaction mixtures to enhance the crystallinity of the MOF crystals/microcrystals. In some cases, crystal growth modulators such as acetic acid or benzoic acid are added to the reaction mixtures to control the particle sizes of the microcrystals. Accordingly, in some embodiments, providing the MOF can comprise synthesizing a MOF comprising an SBU comprising a terminal or bridging OH or $OH_2$ group from a mixture of metal ions or complexes and organic briding ligands or precursors thereof.

The SBU of the provided MOF can be any suitable SBU that comprises a terminal or bridging OH or $OH_2$ group, including those described above as suitable SBUs for a "parent" MOF and in Scheme 1. In some embodiments, the SBU is selected from the group comprising Zr-oxo clusters, Hf-oxo clusters, Zn-oxo clusters, Ti-oxo clusters, Al-oxo clusters, Cu-carboxylate paddlewheels, and Ce-oxo clusters. In some embodiments, the MOF can comprise a plurality of SBUs (e.g., two or more different SBUs). In some embodiments, each of the SBUs comprises at least one, two, three, four or more terminal or bridging OH or $OH_2$ group.

The provided MOF can comprise any suitable organic bridging ligand or mixture of organic bridging ligands. Thus, in some embodiments, the organic bridging ligand is substituted (or derivatized) with one or more groups that include a moiety, such as, but not limited to, a carboxylate or carboxylic acid, an ester, an amide, a pyridine or other nitrogen containing aromatic group, an amine (including nitrogen-containing heterocycles), a hydroxyl, a thiol, a thioalkyl, $—B(OH)_2$, $—SO_3H$, $—PO_3H$, $—NO_2$, or a phosphonate. In some embodiments, the organic bridging ligand comprises one or more carboxylate, pyridine, and/or phosphonate moieties that can coordinate to a metal ion in the SBU. In some embodiments, the organic briding ligand is a carboxylate, e.g., dicarboxylate, a tricarboxylate, or a tetracarboxylate.

The groups (e.g., the carboxylate, pyridine and/or phosphonate groups) that can bond to the SBU the metal ion can be substituted on an alkyl, alkylene, aryl, or arylene group. In some embodiments, they are substituted on an aryl or arylene group and, therefore, the organic briding ligand can comprise an aryl or arylene group. In some embodiments, the arylene group can comprise a plurality of phenylene groups, optionally substituted with one or more aryl group substituents in addition to the groups used to coordinate to the metal of the SBU. In some embodiments, the organic bridging ligand is selected from the group comprising 1,4-bis(4-carboxyphenyl)benzene, TPDC, MTBC, BTC, TPHN, and 1,1'-biphenyl-4,4'-dicarboxylate.

Any suitable catalyst precursor can be used. For example, the catalyst precursor can comprise a metal complex or a hydrate thereof comprising metal M and metal ligands, such as, but not limited to, halides, amines, alkyl groups, aralkyl groups, aryl groups, water, hydroxyl, alkoxy, aryloxy, nitro groups, a carboxylate, etc. In some embodiments, M is selected from the group comprising Mg, Zr, Hf, V, Fe, Co, Cr, Mn, Ni, and Cu. In some embodiments, the catalyst precursor is selected from $CoCl_2$, $Me_2Mg$, $Zr(CH_2Ph)_4$, and $FeBr_2$. The MOF and catalyst precursor can be reacted in any suitable solvent or solvent mixture (e.g., THF) at any suitable temperature. In some embodiments, more than one equivalent of the catalyst precursor (compared to the number of SBU OH or $OH_2$ groups) can be reacted with the MOF. In some embodiments, about 1.5 equivalents of the metal precursor can be reacted with the MOF.

In some embodiments, the MOF is reacted with a base prior to reaction with the catalyst precursor. Reaction with the base can deprotonate the OH or $OH_2$ group of the SBU prior to contact with the catalyst precursor. In some embodiments, the base is a stronger base than hydroxide ion. For example, in some embodiments, the base can be a salt of a Group 1 element (e.g., Na, K, or Li) and a carbanion, amide or hydride. In some embodiments, the base is an alkyllithium, such as, but not limited to, n-butyl lithium (n-BuLi) or trimethylsilylmethyllithium ($LiCH_2SiMe_3$).

In some embodiments, at least one, two, three, four, five, ten, or more equivalents of the base (i.e., compared to the number of SBU OH and/or $OH_2$ groups) can be used. Reaction of the base and the MOF can be performed at any suitable temperature, typically at room temperature or below (e.g., between about room temperature (20-25° C.) and about −78° C.) and in any suitable organic solvent or solvent mixture (e.g., THF, THF/pentanes, THF/hexanes, benzene, etc.).

In some embodiments, the presently disclosed subject matter provides a method for preparing a catalyst, said method comprising: providing a metal-organic framework (MOF), wherein the MOF comprises a secondary building unit (SBU) comprising a metal and a terminal or bridging OH or $OH_2$ group; reacting the MOF with a base to form a deprotonated SBU; and reacting the deprotonated SBU with a catalyst precursor comprising a catalytically active metal or with a reducing agent to reduce a metal in the deprotonated SBU into a catalytically active metal.

The MOF can be provided as described hereinabove and can contain any suitable SBU that comprises a metal and a terminal or bridging OH or $OH_2$ group, such as those described above and in Scheme 1. In some embodiments, the SBU is selected from the group comprising Zr-oxo clusters, Hf-oxo clusters, Zn-oxo clusters, Ti-oxo clusters, Al-oxo clusters, Cu-carboxylate paddlewheels, and Ce-oxo clusters. In some embodiments, the provided MOF can comprise a plurality of SBUs (e.g., two or more different SBUs). In some embodiments, two or more of the SBUs can comprise at least one terminal or bridging OH or $OH_2$ group. In some embodiments, each of the SBUs comprises at least one, two, three, four or more terminal or bridging OH or $OH_2$ group.

The provided MOF can comprise any suitable organic bridging ligand or mixture of organic bridging ligands, such as any of those described hereinabove. In some embodiments, the MOF comprises an organic bridging ligand substituted with one or more carboxylate, pyridine, and/or phosphonate moieties. In some embodiments, the organic bridging ligand is a dicarboxylate, a tricarboxylate, or a tetracarboxylate. In some embodiments, the organic bridging ligand comprises one or more aryl or arylene groups (e.g., one more phenylene or substituted phenylene groups). In some embodiments, the organic bridging ligand is selected from the group comprising 1,4-bis(4-carboxyphenyl)benzene, TPDC, MTBC, BTC, TPHN, and 1,1'-biphenyl-4,4'-dicarboxylate.

In some embodiments, each of the SBUs comprises at least one terminal or bridging OH or $OH_2$ group and reacting the MOF with a base deprotonates all or a portion of the SBUs. In some embodiments, the base is a stronger base than hydroxide. For example, in some embodiments, the base can be a salt of a Group 1 element (e.g., Na, K, or Li) and a carbanion, amide or hydride. In some embodiments, the base is an alkyllithium, such as, but not limited to, n-butyl lithium (n-BuLi) or trimethylsilylmethyllithium ($LiCH_2SiMe_3$) and reacting the MOF with the base provides a SBU with one or more —OLi groups.

In some embodiments, at least one, two, three, four, five, ten, or more equivalents of the base (i.e., compared to the number of SBU OH and/or $OH_2$ groups) can be used. Reaction of the base and the MOF can be performed at any suitable temperature, typically at about room temperature or below (e.g., between about room temperature and about −78° C.) and in any suitable organic solvent or solvent mixture (e.g., THF, THF/pentanes, THF/hexanes, benzene).

In some embodiments, the deprotonated SBU is reacted with a catalyst precursor wherein the catalyst precursor is a compound of the formula $ML_nX$, wherein M is a catalytically active metal, n is an integer between 0 and 5, X is a halide, H, alkyl or aryl group, and each L is independently selected from the group comprising H, halide, an alkyl group, an aralkyl group, an aryl group, a heteroaryl group, an alkoxy group, and an amine. In some embodiments, M is selected from the group comprising Mg, Zr, Hf, V, Fe, Co, Cr, Mn, Ni, and Cu. The catalyst precursor can comprise a metal complex or a hydrate thereof comprising metal M and metal ligands, such as, but not limited to, halides, amines, alkyl groups, aralkyl groups, aryl groups, water, hydroxyl, alkyoxy, aryloxy, nitro groups, a carboxylate, etc. In some embodiments, the catalyst precursor is selected from $CoCl_2$, $Me_2Mg$, $Zr(CH_2Ph)_4$, and $FeBr_2$.

The deprotonated MOF and catalyst precursor can be reacted in any suitable solvent or solvent mixture (e.g., THF). In some embodiments, more than one equivalent of the catalyst precursor (compared to the number of deprotonated SBU OH or $OH_2$ groups) can be reacted with the MOF. In some embodiments, about 1.5 equivalents of the metal precursor can be reacted with the MOF.

Alternatively, in some embodiments, the deprotonated SBU is reacted with a reducing agent. Reaction with the reducing agent can transform a metal center already present in a SBU of the deprotonated MOF (i.e., the metal present in the SBU of the provided/parent MOF) into a catalytically active metal. In some embodiments, the reducing agent is a borane or a silane. In some embodiments, the reducing agent is pinacolborane or triethylsilane.

In some embodiments, the SBU comprises a Ce-oxo cluster. In some embodiments, the MOF further comprises a trimesic acid organic bridging ligand. In some embodiments, the method provides a catalyst comprising a catalytic site comprising $Ce^3$.

In some embodiments the presently disclosed subject matter provides uses of the thus produced catalysts in catalyzing organic reactions such as, but not limited to, the organic reactions shown in Scheme 2, below, or other related reactions in a batch mode, in conventional solvents, or in the absence of solvents, or in unconventional solvents, such as supercritical carbon dioxide. In some embodiments the presently disclosed subject matter provides uses of thus obtained catalysts for catalyzing organic reactions shown in Scheme 2 or other related reactions in a flow reactor. In some embodiments the presently disclosed subject matter provides for the use of the catalysts to catalyze sequential or multistep reactions.

III. Catalytic Reactions

As an emerging class of porous molecular materials, metal-organic frameworks (MOFs) provide a highly tunable platform to engineer heterogeneous catalysts for various potential reactions that cannot be achieved with traditional porous inorganic materials. In some embodiments, the presently disclosed MOFs can stabilize highly active species that could undergo bimolecular deactivation in solution. Due to the high stability of MOF-frameworks and the ease of functionalization of SBUs with a wide range of metal ions, MOFs have offered a versatile platform to develop practical earth-abundant metal and other metal catalysts for sustainable chemical catalysis and industrially important reactions.

In some embodiments the presently disclosed subject matter provides uses of presently disclosed MOFs and/or the catalysts prepared by the presently disclosed methods as catalysts for one or more of the reactions shown in Scheme 2, below, or other related reactions. In some embodiments, the reactions can be performed in a batch mode, in conventional solvents, or in the absence of solvents, or in unconventional solvents, such as supercritical carbon dioxide. In some embodiments the presently disclosed subject matter provides uses of the MOFs and/or catalysts prepared by the methods described above for reactions shown in Scheme 2 or other related reactions in a flow reactor or a supercritical fluid reactor to enable green manufacturing of fine chemicals. In some embodiments the presently disclosed subject matter provides for the use of the MOFs and/or catalysts prepared by the methods described above to catalyze sequential or multistep reactions. In some embodiments the presently disclosed subject matter provides for the use of multiple MOFs and/or catalysts prepared by the methods above in the same system to catalyze sequential or multistep reactions.

Scheme 2. Exemplary Organic Reactions Catalyzed By Metalated MOF-SBUs.

Ethylene Oligomerization

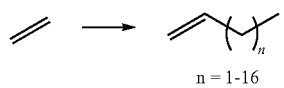

n = 1-16

Alkyne Coupling

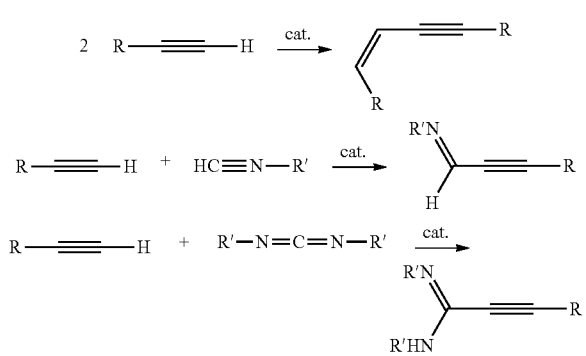

Hydromethylation

Alkane Dehydrosilyation

Alkane Metathesis

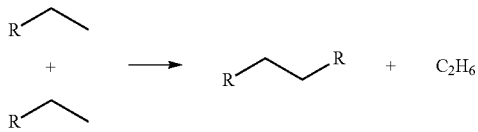

Dehydrogenative alkyl C-H phosphination

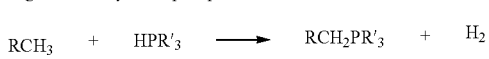

-continued

Pyridine Functionalization

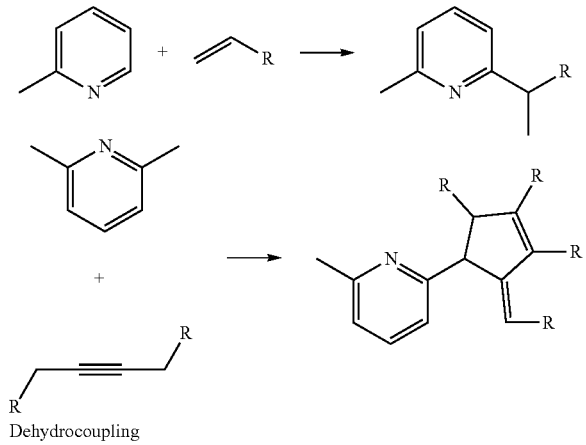

Dehydrocoupling

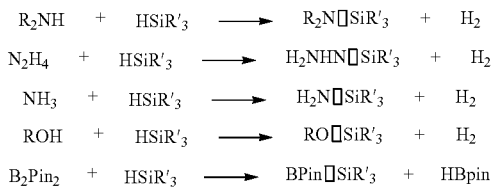

Hydrosilylation of olefins

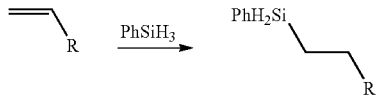

Oxidation of Primary Alcohols to Aldehydes

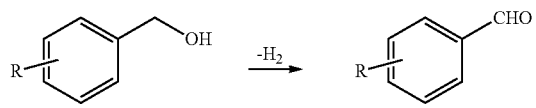

Hydroamination:

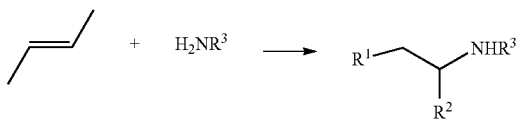

Hydroformylation:

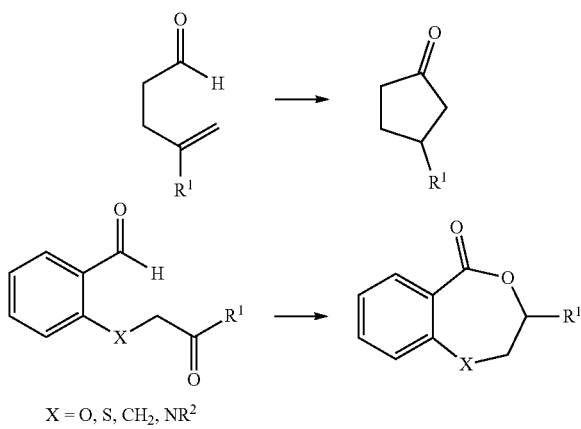

X = O, S, CH$_2$, NR$^2$

Accordingly, in some embodiments, the presently disclosed subject matter provides a method for preparing a compound comprising contacting a substrate capable of forming a product by catalytic transformation with a heterogeneous catalyst prepared according to one of the methods described above and/or with an MOF comprising a SBU comprising one or more —OM'L$_x$ and/or —(OH)M'L; groups, wherein M' is a metal, x is an integer between 0 and 5, and each L is independently selected from the group comprising H, a halide, an alkyl group, an aryl group, a heteroaryl group, an alkoxy group, and an amine. In some embodiments, the catalytic transformation is selected from the group comprising ethylene oligomerization, alkyne coupling, hydromethylation, alkane dehydrosilation, alkane metathesis, dehydrogenative alkyl C—H phosphination, pyridine functionalization, dehydrocoupling, hydrosilation of olefins, ketones and aldehydes, oxidation of primary alcohols, hydroamination, hydroformylation, C—H borylation, hydrogenation of alkenes, imines, carbonyls, nitroarenes, and heterocycles, hydroboration, hydrophosphination, and C—H amination. In some embodiments, the catalytic transformation is selected from the group comprising alkene hydrogenation (including the hydrogenation of trisubstituted alkenes), benzylic C—H borylation of an arene substrate, hydroboration of a carbonyl compound substrate (e.g., a ketone or aldehyde) or an alkene substrate, silylation of a benzylic C—H group, hydroamination, hydrogenation of an imine or carbonyl compound substrate (e.g., a ketone or aldehyde), hydrogenation of a nitroarene substrate, and hydrophosphination of an alkene substrate. In some embodiments, the catalytic transformation is conducted in a batch reactor, a flow reactor, or in a supercritical fluid reactor.

Figure 35:
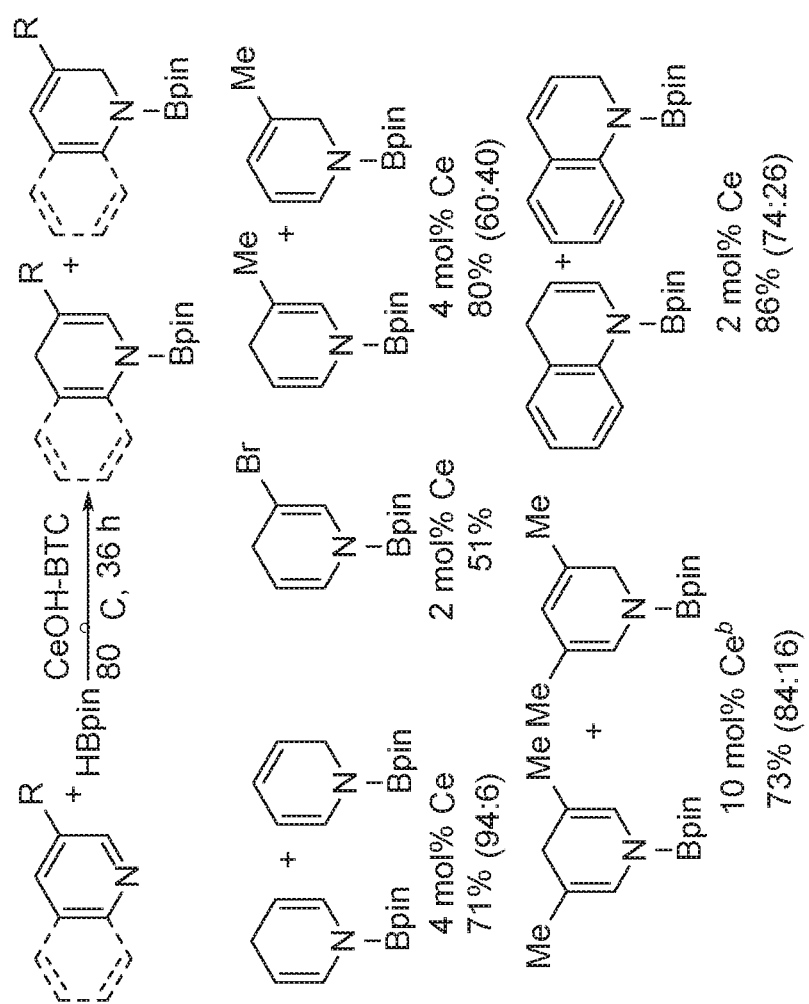
FIG. 35 is a schematic drawing showing a reaction scheme for the 1,4-selective hydroboration of pyridine derivatives catalyzed by the reduced metal organic framework (CeH-BTC) (top) and exemplary products and yields from the catalyzed reaction (bottom).

In some embodiments, the presently disclosed MOF-based catalysts are more active than their homogeneous counterparts (e.g., similar metal complexes that are not present in a MOF and that can be dissolved in a solution with the substrates involved in the catalytic transformation). In some embodiments, the catalyzed transformations can have yields above 80%, above 85%, above 90%, or above 95%. In some embodiments, the transformation can have about 100% yield. In some embodiments, the presently disclosed catalysts have no homogeneous counterpart (i.e., a similar metal complex that can catalyze the same catalytic transformation with the same substrate and/or to produce the same product or product mixture). For example, in some embodiments, the presently disclosed subject matter provides a MOF-based catalyst that can catalyze the hydroboration of a pyridine substrate with 1,4-regioselectivity. See FIG. 35.

The contacting of the substrate and the MOF/catalyst can take place in any suitable solvent, e.g., a solvent in which the substrate can be dissolved. In some embodiments, the solvent is an ether, such as tetrahydrofuran or dioxane; a halogenated alkene, such as dichloromethane, dichloroethane, or chloroform; an aromatic solvent, such as benzene, toluene, or xylene; an alcohol, such as methanol or ethanol; water, or mixtures thereof. In some embodiments, the solvent is an unconventional solvent, such as supercritical carbon dioxide. In some embodiments, no solvent is present. In some embodiments, the contacting takes place in the presence of a gas, such as hydrogen gas, and/or under pressure. In some embodiments, the contacting is done in conjunction with heating or cooling.

In some embodiments, the catalytic transformation is done in a flow reactor, e.g., wherein the MOF/catalyst is present in a reaction chamber into which a solvent or solvents can be pumped in and out and wherein the solvent or solvents can comprise a substrate or substrates dissolved therein.

The presently disclosed catalysts can have high turnover number (TON). For example, in some embodiments, the presently disclosed MOF-based catalysts can have a TON of greater than about 50, greater than about 100, greater than about 500, greater than about 1000, or greater than about 5,000. In some embodiments, the TON can be about 10,000 or greater.

In some embodiments, the presently disclosed catalysts can be used at low catalyst loadings, e.g., at less than about 20 mole (mol) % 10 mol %, less than about 5 mol %, less than about 3 mol %, less than about 1 mol %, less than about 0.5 mol %, or less than about 0.2 mol %. In some embodiments, the catalysts can be used at a catalyst loading of between about 0.001 mol % and about 1 mol % or between about 0.005 mol % and about 0.2 mol % (i.e., at about 0.005 mol %, 0.01 mol %, 0.05 mol %, 0.1 mol % or at about 0.2 mol %). Accordingly, in some embodiments, the contacting can be performed wherein the MOF/catalyst is present at about 1 mol % or less compared to the substrate.

In some embodiments, the presently disclosed catalysts/MOFs can be recycled and reused. In some embodiments, the catalysts/MOFs can be reused at least 2, 3, 4, 5, 6, 7, 8, or 9 times without significant loss of activity.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods for Examples 2-9

Solvents were purchased from Fisher (Thermo Fisher Scientific, Waltham, Mass., United States of America) and used without further purification. All of the other substrates and reagents were commercially available and used as received unless indicated otherwise. Styrene, 1-octene, α-methylstyrene, cis-β-methylstyrene, allyl acetate, and benzaldehyde were distilled and then dried over freshly activated 4 Å molecular sieves prior to use. Cyclohexene, m-xylene, p-xylene, ethylbenzene, 4-tert-butyltoluene, 4-methylanisole, acetophenone, and 2-acetylthiophene were degassed and then dried with freshly activated 4 Å molecular sieves in a glovebox prior to use. Pinacolborane ($B_2pin_2$) was purchased from Fisher (Thermo Fisher Scientific, Waltham, Mass., United States of America) and was freshly distilled prior to use. $^1H$ NMR spectra were recorded on a Bruker NMR 400 DRX spectrometer (Bruker Corporation, Billerica, Mass., United States of America) at 400 MHz and referenced to the proton resonance resulting from incomplete deuteration of the deuterated chloroform (δ 7.26) or deuterated dimethylsulfoxide (DMSO) (δ 2.50). Thermogravimetric analysis (TGA) was performed in air using a Shimadzu TGA-50 (Shimadzu Corporation, Kyoto, Japan) equipped with a platinum pan. Powder X-ray diffraction (PXRD) patterns were collected on a Bruker D8 Venture, dual microsource (Cu and Mo) diffractometer (Bruker Corporation, Billerica, Mass., United States of America) with a CMOS detector. Cu Kα radiation was used. The PXRD patterns were processed with the APEX 2 package using PILOT plug-in. Background diffraction signal from glass capillary tube and solvent at 2θ~20° was simulated and removed by the program PowderX. Inductively coupled plasma mass spectrometry (ICP-MS) data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a 159 Tb internal standard against a six-point standard curve over the range from 0.1 parts-per-billion (ppb) to 1000 ppb. The correlation coefficient was >0.9997 for all analytes of interest. Data collection was performed in Spectrum Mode with five replicates per sample and 100 sweeps per replicate.

GC Analysis:

The conversions of reactions and yields of the products were determined by gas chromatography (GC) using a Shimadzu GC-2010 gas chromatograph (Shimadzu Corporation, Kyoto, Japan) equipped with a flame ionization detector (FID) and Supelco β-dex 120 column (Sigma-Aldrich, St. Louis, Mo., United States of America).

GC conditions: Inj: 220° C.; Det: 250° C.; Column temp: 80° C. followed by a ramp of 2° C./min to 200° C. and held for 10 minutes; Column flow: 1.11 mL/min.

Example 2

Synthesis and Characterization of UiO-MOFs

The 1,4-bis(4-carboxyphenyl)benzene bridging ligand used to prepare UiO MOFs was prepared in two steps from 1,4-diiodobenzene and 4-methoxycarbonylphenylboronic acid as shown in Scheme 3, below.

Scheme 3. Synthesis of 1,4-bis(4-carboxyphenyl)benzene.

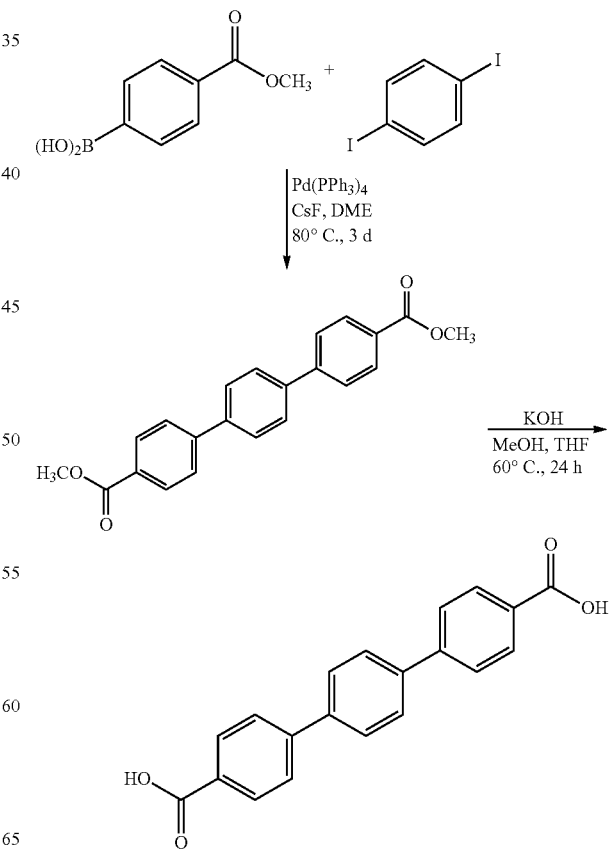

Synthesis of 1,4-bis(4-methoxycarbonylphenyl)benzene 1,4-diiodobenzene (1.00 g, 3.03 mmol) and 4-methoxycarbonylphenylboronic acid (1.64 g, 9.09 mmol) were suspended in 94 mL of 1,2-dimethoxyethane in a glove box. Tetrakis(triphenylphosphine) palladium (175 mg, 0.152 mmol) and cesium fluoride (4.14 g, 27.3 mmol) were then added. The resulting mixture was sealed in a pressure vessel under nitrogen and stirred at 80° C. for 3 days. After cooling to room temperature, the reaction mixture was mixed with $H_2O$ (20 mL), and centrifuged to obtain solid crude compound. The solid was then washed sequentially with $H_2O$, dimethoxyethane and THF to remove impurities and dried in vacuo to afford 1,4-bis(4-methoxycarbonylphenyl)benzene as a white solid (420 mg, 1.21 mmol, 40% yield). $^1$H NMR (500 MHz, CDCl$_3$): δ 8.14 (d, 2H, $^3J_{HH}$=8.4 Hz), 7.74 (s, 4H), 7.72 (d, 4H, $^3J_{HH}$=8.4 Hz), 3.96 (s, 6H).

Synthesis of 1,4-bis(4-carboxyphenyl)benzene 1,4-bis(4-carboxyphenyl)benzene (420 mg, 1.21 mmol) was suspended in THF (65 mL). A solution of KOH (6.17 g, 110 mmol) dissolved in MeOH (20 mL) was then added, and the reaction mixture was stirred at 60° C. for 24 h. The suspension was cooled to room temperature and the resulting precipitate was collected by centrifugation. The solution was washed with dry THF (20 mL) and recollected by centrifugation. The solid was suspended in THF (20 mL) and trifluoroacetic acid (3 mL) was slowly added and stirred for 1.5 h at room temperature. $H_2O$ (15 mL) was then added, and the white solid was isolated by centrifugation, and subsequently washed with THF and Et$_2$O, and dried in vacuo to obtain 1,4-bis(4-carboxyphenyl)benzene (331.9 mg, 1.04 mmol, 86% yield) as a pale-white solid. $^1$H NMR (500 MHz, DMSO-d$_6$) δ 13.00 (br s, 2H), 8.05 (d, 4H, $^3J_{HH}$=8.3 Hz), 7.89 (s, 4H), 7.88 (d, 4H, $^3J_{HH}$=8.3 Hz).

Synthesis and Characterization of UiO-68-MOF

Figure 1:
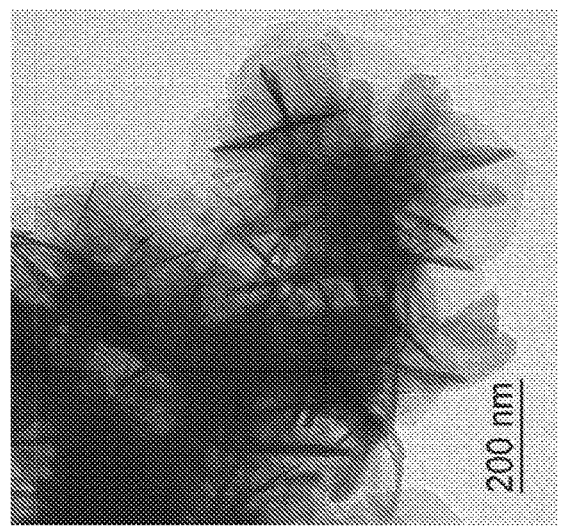
FIG. 1 is a transmission electron microscopy (TEM) image of a metal organic framework, referred to as UiO-68-MOF, prepared from $ZrCl_4$ and 1,4-bis(4-carboxyphenyl)benzene and comprising zirconium oxide secondary building units and the 1,4-bis(4-carboxyphenyl)benzene as a organic bridging ligand.

ZrCl$_4$ (1.30 mg, 5.03 μmol), 1,4-bis(4-carboxyphenyl)benzene (1.6 mg, 5.53 μmol) were dissolved in 0.8 mL of DMF in 1 dram vial, and 15.4 μL of trifluoroacetic acid was then added. The vial was capped and then heated at 12000 for 3 days to afford a white solid as the MOF product (2.0 mg, 95% yield). A transmission electron micrograph image of the as synthesized UiO-68-MOF is shown in FIG. 1.

Synthesis and Characterization of UiO-68-MOF-CoCl

Figure 2B:
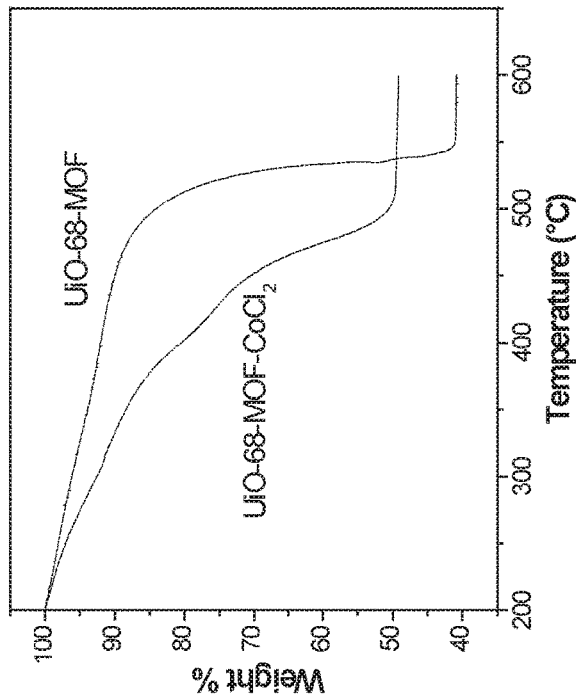
FIG. 2B is an expansion of the thermogravimetric analysis (TGA) curves from FIG. 2A in the 200-600 degrees Celsius (° C.) range. The increase in residual mass at 600° C. for the metalated metal organic framework is due to the presences of the cobalt.

In a glovebox, UiO-68-MOF (20.0 mg) in 3 mL THF was cooled to −30° C. for 30 min. To the cold suspension, 33 μL of nBuLi (2.5 M in hexanes) was added drop wise and the resultant light yellow mixture was stirred slowly overnight at room temperature. The light yellow solid was centrifuged out and washed with THF 5-6 times over 6 h. Then, the lithiated UiO-68-MOF was transferred to a vial containing 5 mL THF solution of CoCl$_2$ (6.0 mg). The mixture was stirred for 15 h and the deep blue solid was then centrifuged out and washed with THF for 5-8 times. The metalated MOFs were then stored in THF in the glovebox for further uses. UiO-68-MOF-CoCl has 45% solvent weight based on TGA analysis (see FIGS. 2A and 2B) and 100% Co-loading with respect to μ$^3$-OH centers based on ICP-MS analysis.

Synthesis and Characterization of UiO-66-MOF-CoCl and UiO-67-MOF-CoCl

UiO-66-MOF-CoCl and UiO-67-MOF-CoCl were prepared by post-synthetic metalation of UiO-66-MOF and UiO-67-MOF, respectively, with CoCl$_2$ using similar method used for synthesizing UiO-68-MOF-CoCl as described above. UiO-66-MOF-CoCl and UiO-67-MOF-CoCl have and 100% Co-loading with respect to μ$^3$-OH centers based on ICP-MS analysis.

Figure 3:
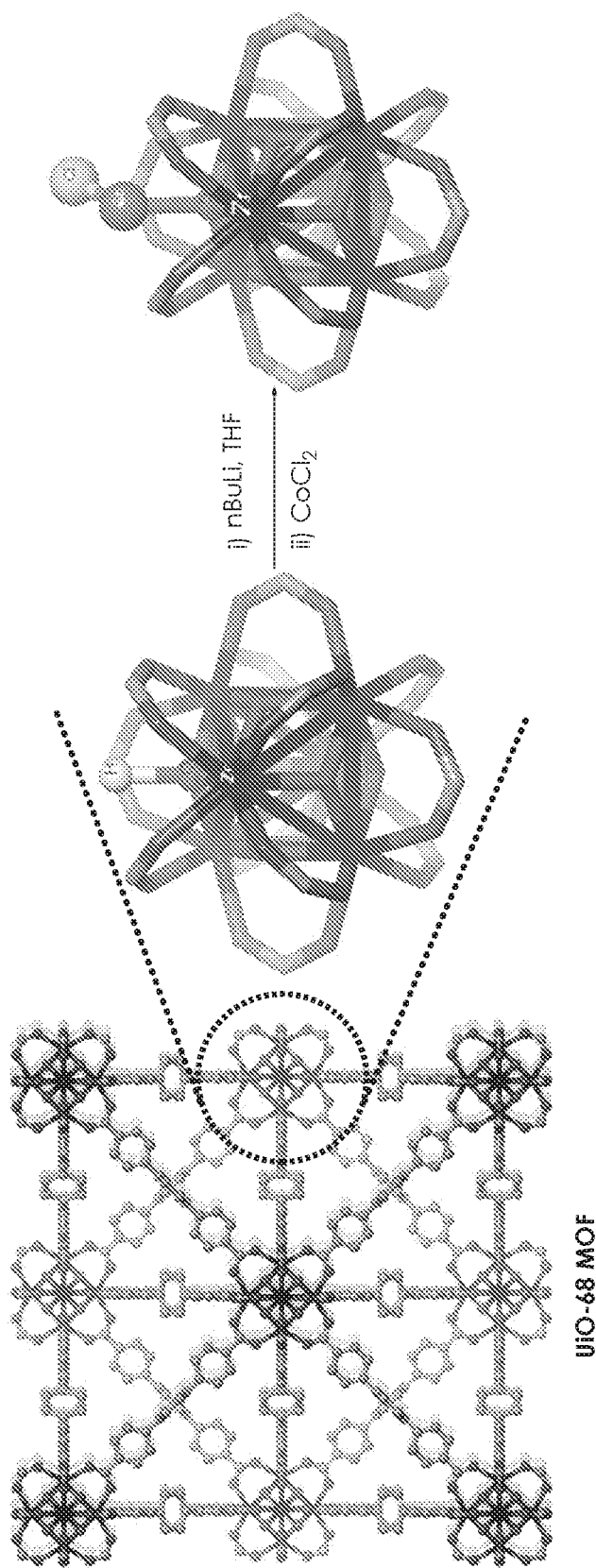
FIG. 3 is a schematic drawing showing the postsynthetic metalation of a zirconium (Zr) oxide secondary building unit (SBU) of the metal organic framework (UiO-68-MOF) described for FIG. 1 with cobalt chloride ($CoCl_2$). n-Butyl lithium (nBuLi) is used to deprotonate a OH group in the SBU prior to metalation.
Figure 4:
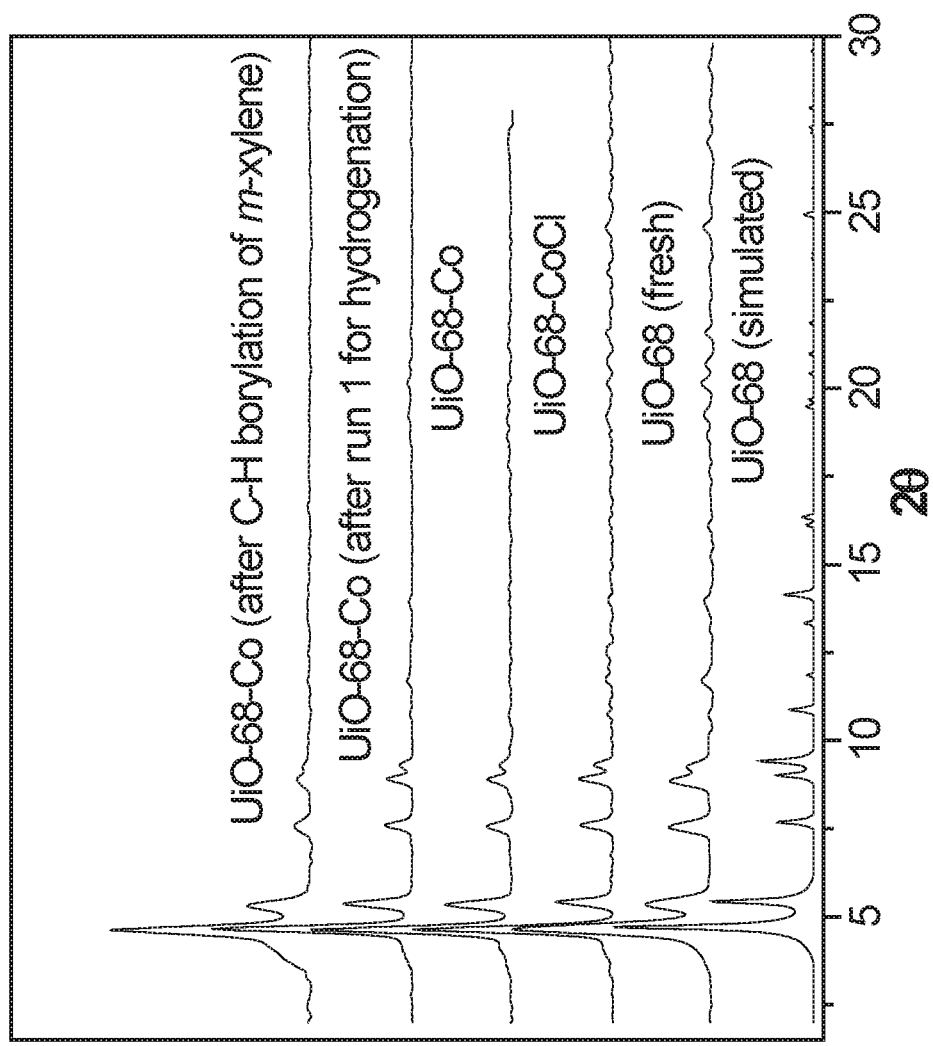
FIG. 4 is a graph showing the powder x-ray diffraction (PXRD) patterns simulated for the metal organic framework (MOF) described for FIG. 1 (UiO-68 (simulated)), experimentally determined for the MOF described for FIG. 1 (UiO-68 (fresh)), experimentally determined for the post-synthetically metalated MOF (UiO-68-CoCl), experimentally determined for the metalated MOF activated for use as a catalyst with sodium triethylborohydride ($NaEt_3BH$) (UiO-68-Co), experimentally determined for the MOF catalyst after recovery from its use as a catalyst for the hydrogenation of 1-octene (UiO-68-Co (after run 1 for hydrogenation)), and experimentally determined for the MOF catalyst after recovery for use as a catalyst for the C—H borylation of m-xylene (UiO-68-Co (after C—H borylation of m-xylene)). The PXRD patterns indicate that the MOF retains crystallinity after post-synthetic metalation and catalysis.

Summary:

UiO-68-MOF was synthesized via a solvothermal reaction between ZrCl$_4$ and 1,4-bis(4-carboxyphenyl)benzene in the presence of DMF and trifluoroacetic acid in 95% yield. The deprotonation of Zr—OH in SBUs with nBuLi followed by reaction with CoCl$_2$ in THF afforded the Co-functionalized UiO-68-MOF as a deep blue solid. See FIG. 3. ICP-MS analysis of the Zr/Co ratio of the digested UiO-68-CoCl revealed 100% metalation of Zr—OH sites at SBUs. Crystallinity of UiO-68-MOF was maintained upon metalation as shown by similar PXRD patterns of UiO-68 and UiO-68-CoCl. See FIG. 4.

Example 3

Benzylic C—H Borylation of Arenes with UiO-MOF-Co

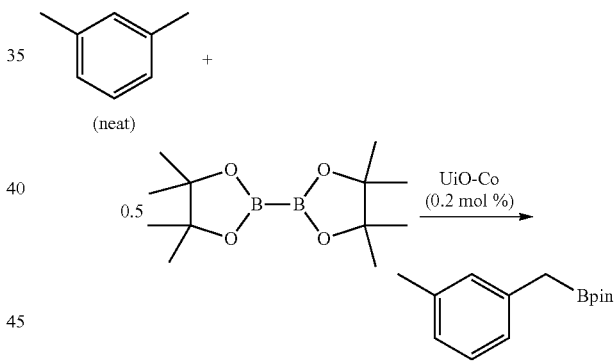

Scheme 4. Typical Borylation Reaction Catayzed by UiO-68-MOF-Co.

Typical Procedure for UiO-68-MOF-Co Catalyzed Benzylic C—H Borylation of Arenes:

Scheme 4, above, shows a typical borylation reaction that can be catalyzed by UiO-68-MOF-Co. In a glovebox, UiO-68-MOF-CoCl (1.0 mg, 0.2 mol % Co) was charged into a small vial and 0.5 mL THF was added. Then, 15 μL NaBEt$_3$H (1.0 M in THF) was added to the vial and the mixture was stirred slowly for 1 h in the glovebox. The solid was centrifuged out of suspension and washed with THF two times and with m-xylene one time. B$_2$pin$_2$ (43.0 mg, 0.169 mmol) in 2.0 mL m-xylene was added to the vial and the resultant mixture was transferred to a Schlenk tube. The tube was heated under nitrogen at 103° C. for 3 d. The reaction mixture was cooled to room temperature and the solid was centrifuged out of suspension. The extract was passed through a short plug of celite and then concentrated in vacuo to give pure boronate ester in 92% yield.

Test of "Heterogeneity" of the MOF Catalysis in C—H Borylation:

In a glovebox, UiO-68-MOF-CoCl (1.0 mg, 0.2 mol % Co) was charged into a small vial and 0.5 mL THF was added. Then, 15 μL NaBEt$_3$H (1.0 M in THF) was added to the vial and the mixture was stirred slowly for 1 h in the glovebox. The solid was centrifuged out of suspension and washed with THF for two times and with p-xylene for one time. B$_2$pin$_2$ (43.0 mg, 0.169 mmol) in 2.0 mL p-xylene was added to the vial and the resultant mixture was transferred to a Schlenk tube. The tube was heated under nitrogen at 103° C. for 48 h to obtain the alkyl boronate ester in 89% yield as determined by GC-analysis.

For comparison, in a glovebox, UiO-68-MOF-CoCl (1.0 mg, 0.2 mol % Co) was charged into a small vial and 0.5 mL THF was added. Then, 15 μL NaBEt$_3$H (1.0 M in THF) was added to the vial and the mixture was stirred slowly for 1 h in the glovebox. The solid was centrifuged out of suspension and washed with THF for two times and with p-xylene for one time. B$_2$pin$_2$ (43.0 mg, 0.169 mmol) in 2.0 mL p-xylene was added to the vial and the resultant mixture was transferred to a Schlenk tube. The tube was heated under nitrogen at 103° C. for 48 h. The solid catalyst was separated via centrifugation and the supernatant was filtered through a celite. Then, the supernatant was stirred at 103° C. for an additional 48 h. GC-analysis showed that the alkyl-boronate ester was obtained in 86% yield. These two reactions afforded almost the same yields, indicating that the UiO-68-MOF-Co is the actual catalyst for benzylic C—H borylation.

Control to Assess Effect of Surface Trapped Co-Species:

To demonstrate the effects of any surface trapped Co-species, control studies were carried out with UiO-68-MOF. UiO-68-MOF (12 mg) was transferred to a vial containing 5 mL THF solution of CoCl$_2$ (4.0 mg). The mixture was stirred slowly for 16 h and the solid was then centrifuged out and washed with THF for 5-8 times over 24 h. The white color of UiO-68-MOF remained unchanged upon metalation. A small amount of Co was detected by ICP-MS (Co:Zr=0.018: 1). Upon treatment of NaEt$_3$BH, the resulting solid was found to be inactive for benzylic C—H borylation of neat p-xylene at 103° C. (0.2 mol % Co loading). These observations suggest that surface trapped nanoparticles contribute little, if any, to the catalytic activity of the MOF catalyst.

A control study was also carried out using Co-nanoparticles. To a THF solution (0.2 mL) of CoCl$_2$ (1.0 mg), NaEt$_3$BH (23 μL) was added and a black precipitate was formed immediately. The resulting mixture was stirred for 1 h and then transferred to a Schenk tube containing B$_2$pin$_2$ (19.6 mg, 0.077 mmol) dissolved in 1.5 mL of p-xylene. The resultant mixture was heated under N$_2$ at 103° C. for 2 days. The gas chromatography (GC) analysis showed no formation of boronate ester.

Investigation of Substrate Size on Catalytic Activity in Benzylic C—H Borylation:

In a glovebox, UiO-68-MOF-CoCl (1.0 mg, 0.2 mol % Co) was charged into a small vial and 0.5 mL THF was added. Then, 15 μL NaBEt$_3$H (1.0 M in THF) was added to the vial and the mixture was stirred slowly for 1 h in the glovebox. The solid was centrifuged out of suspension and washed with THF two times and with heptane two times. B$_2$pin$_2$ (43.0 mg, 0.169 mmol) and p-xylene (41.8 μL, 0.34 mmol) in 2.0 mL heptane was added to the vial and the resultant mixture was transferred to a Schenk tube. The tube was heated under nitrogen at 103° C. for 2.5 d to obtain the alkyl boronate ester in 94% yield as determined by GC analysis.

The borylation reactions of 4-tert-butyl-toluene and 3,5-di-tert-butyl-toluene were conducted using the same procedure described above under identical reaction conditions and the results are summarized in Table 3, below. The yield of the boronate ester decreased upon increase in the size of the substrate. These results indicate that catalysis can be facilitated by Co-sites both inside the pores and on the outside of the MOFs, not the framework surface alone.

Determination of the Rate Law for UiO-68-MOF-Co-Catalyzed Benzylic C—H Borylation:

The rate law of the benzylic C—H borylation of p-xylene was determined by the method of initial rates (up to 10% conversion). The reactions were conducted in heptane (total volume of solution was 2.0 mL) in a Schlenk tube at 103° C. The Schlenk tube was connected to a reflux condenser under N$_2$. To determine the rate dependence on one reagent, the concentration of that reagent was varied, while the concentration of other reagents and the total volume of the solution (2.0 mL) were held constant. After borylation reaction for 12 h, mesitylene (10 μL) was added to the reaction mixture and then the concentration of the p-xylene was determined by GC using mesitylene as the internal standard. The rates refer to the rates of decrease of p-xylene in units of M·s$^{-1}$. To determine the rate dependence on p-xylene, the concentration of p-xylene was varied between $0.8 \times 10^{-1}$-$2.03 \times 10^{-1}$ M, while the concentration of Co was $2.71 \times 10^{-4}$ M and concentration of B$_2$pin$_2$ was $8.5 \times 10^{-2}$ M. See FIG. 5A. To determine the rate dependence on catalyst, the concentration of Co was varied between $2.71 \times 10^{-4}$-$6.78 \times 10^{-1}$ M, while the initial concentrations of p-xylene and B$_2$pin$_2$ was $3.41 \times 10^{-1}$ M and $1.70 \times 10^{-1}$ M, respectively. See FIG. 5A. To determine the rate dependence on B$_2$pin$_2$, the concentration of B$_2$pin$_2$ was varied between $3.94 \times 10^{-2}$-$9.84 \times 10^{-2}$ M, while the concentrations of p-xylene and Co were $3.41 \times 10^{-1}$ M and $2.0 \times 10^{-4}$ M, respectively. See FIG. 5B.

Summary:

Upon treatment of NaEt$_3$BH, UiO-68-Co became an active catalyst for undirected dehydrogenative borylation of benzylic C—H bonds using B$_2$(pin)$_2$ (pin=pinacolate) or HBpin as the borylating agents. Borylation of alkyl C—H bonds provides alkyl boronates, which are versatile reagents in organic synthesis. The UiO-68-Co catalyzed borylation reactions were first screened for optimized conditions such as temperature, solvents, and in neat arenes (without using a solvent) to obtain better results. The screening experiments revealed that high turnover frequencies as well as regioselectivities were observed when the borylation reactions were performed using B$_2$(pin)$_2$ in neat arene or refluxed in n-heptane for solid substrates at 103° C. See Table 1, below. The catalytic activity and regioselectivity of UiO-68-Co was higher compared to those of analogous UiO-MOFs having smaller pore sizes such as UiO-67-Co and UiO-66-Co. See Table 2, below. Under optimized reaction conditions, primary benzylic boronate esters were afforded in excellent yields from a range of methylarenes with 0.2 mol % UiO-68-Co. See Table 1. Impressively, UiO-68-Co catalyzed borylation occurred not only at primary benzylic C—H bonds, but also at secondary and tertiary benzylic C—H bonds. See entries 12 and 13, Table 1.

TABLE 1

UiO-68-Co-catalyzed benzylic C—H borylation of arenes[a]

| Entry | Substrate | Product(s) | % Co-loading | Time | % Conversion [Benzyl:Ar] |
|---|---|---|---|---|---|
| 1 | 3,5-dimethylbenzene (m-xylene) | 3-methylbenzyl-Bpin + 3,5-dimethylphenyl-Bpin | 0.2 | 2.5 d | 100 (92) [96:4] |
| 2 | p-xylene | 4-methylbenzyl-Bpin | 0.2 | 2 d | 100 (96) |
| 3 | toluene | benzyl-Bpin | 0.2 | 5 d | 100 (72) |
| 4 | mesitylene | 3,5-dimethylbenzyl-Bpin | 0.2 | 2 d | 100 |
| 5 | mesitylene | 3,5-dimethylbenzyl-Bpin | 0.05 | 5 d | 100 (94) |
| 6 | mesitylene | 3,5-dimethylbenzyl-Bpin | 0.025 | 12 d | 58 |
| 7 | 4-tBu-toluene | 4-tBu-benzyl-Bpin | 0.2 | 6 d | 100 (86) |
| 8 | 4-MeO-toluene | 4-MeO-benzyl-Bpin + 4-MeO-aryl-Bpin | 0.2 | 2.5 d | 100 (84:12) |
| 9 | 4-iPr-toluene | 4-iPr-benzyl-Bpin + 4-tBu-benzyl-Bpin (CH2Bpin) | 0.2 | 2 d | 100 (60:40) |
| 10 | cyclohexene | cyclohexenyl-Bpin + cyclohexyl-Bpin | 1.0 | 2 d | 100 |
| 11 | 3-Cl-toluene | 3-Cl-benzyl-Bpin | 0.2 | 5 d | 100 (56) |
| 12 | ethylbenzene | PhCH(Bpin)CH3 + PhCH2CH2Bpin + aryl-Bpin | 0.2 | 3 d | 100 (78:11:11) |

TABLE 1-continued

UiO-68-Co-catalyzed benzylic C—H borylation of arenes[a]

| Entry | Substrate | Product(s) | % Co-loading | Time | % Conversion [Benzyl:Ar] |
|---|---|---|---|---|---|
| 13 | 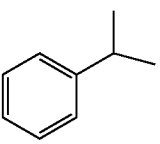 | 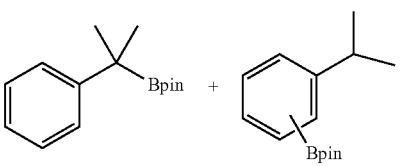 | 0.2 | 6 d | 100 (80:20) |

[a]Reaction conditions: 1.0 mg of UiO-68-CoCl, 5 equiv NaBEt$_3$H (1.0M in THF), arene, B$_2$pin$_2$, 103° C., N$_2$.

TABLE 2

Optimization of benzylic C—H borylation of arenes catalyzed by UiO-MOF-Co.[a]

| Entry | Catalyst (0.2 mol % Co) | Temperature (° C.) | Time (d) | % Conversion [Benzyl:Ar] |
|---|---|---|---|---|
| 1 | UiO-66-Co | 103 | 2.5 d | 21 |
| 2 | UiO-67-Co | 103 | 2.5 d | 25 (40:60) |
| 3 | UiO-68-Co | 103 | 2.5 d | 100 (96:4) |
| 4 | UiO-68-Co | 106 | 2.5 d | 100 (88:12) |
| 5 | UiO-68-Co | 96 | 3 d | 100 (96:4) |
| 6 | UiO-68-Co | 110 | 2.5 d | <50 |

[a]Reaction conditions: 1.0 mg of UiO-CoCl, 5 equiv NaBEt$_3$H (1.0M in THF), m-xylene (2 mL), B$_2$pin$_2$, N$_2$.

At a 1.0 mol % Co loading, the MOF-Co catalyst was reused at least times in the borylation of p-xylene. Notably, the boronate ester was obtained in high purity simply by removing the solid catalyst and the organic volatiles. The heterogeneity of UiO-68-Co was confirmed by several experiments. The PXRD patterns of UiO-68-Co recovered from the first remained the same as that of freshly prepared UiO-68-Co (see FIG. 4), indicating that the MOF framework is stable under the catalytic conditions. The leaching of Co and Zr into the supernatant was very low during the course of the borylation reaction as shown by ICP-MS analysis. The amounts of Co and Zr leaching into the supernatant after the first run were 0.14% and 0.056%, respectively. Moreover, no further conversion was detected after removal of UiO-68-Co from the reaction mixture. In addition, UiO-68-Co gave higher conversion of p-xylene compared to the analogous bulkier alkenes, 4-tert-butyl-toluene and 3,5-di-tert-butyl-toluene under identical conditions, which demonstrates that catalysis is facilitated by Co-sites both inside the pores and on the outside of the MOFs not the framework surface alone. See Table 3.

TABLE 3

Effect of Substrate Size on Catalysis[a]

| Entry | Substrate | Product(s) | % Co-loading | Time | % Yield |
|---|---|---|---|---|---|
| 1 | 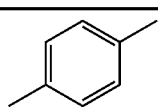 | 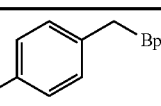 | 0.2 | 2.5 d | 94 |
| 2 | 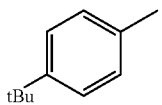 | 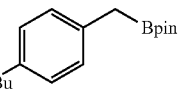 | 0.2 | 2.5 d | 22 |
| 3 | 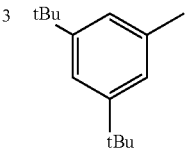 | 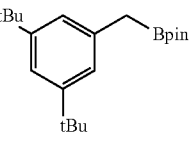 | 0.2 | 2.5 d | 6 |

[a]Reaction conditions: 1.0 mg of UiO-68-CoCl, 5 equiv NaBEt$_3$H (1.0M in THF), arene, B$_2$pin$_2$, 103° C. heptanes (2 mL), reflux under N$_2$.

Figure 6:
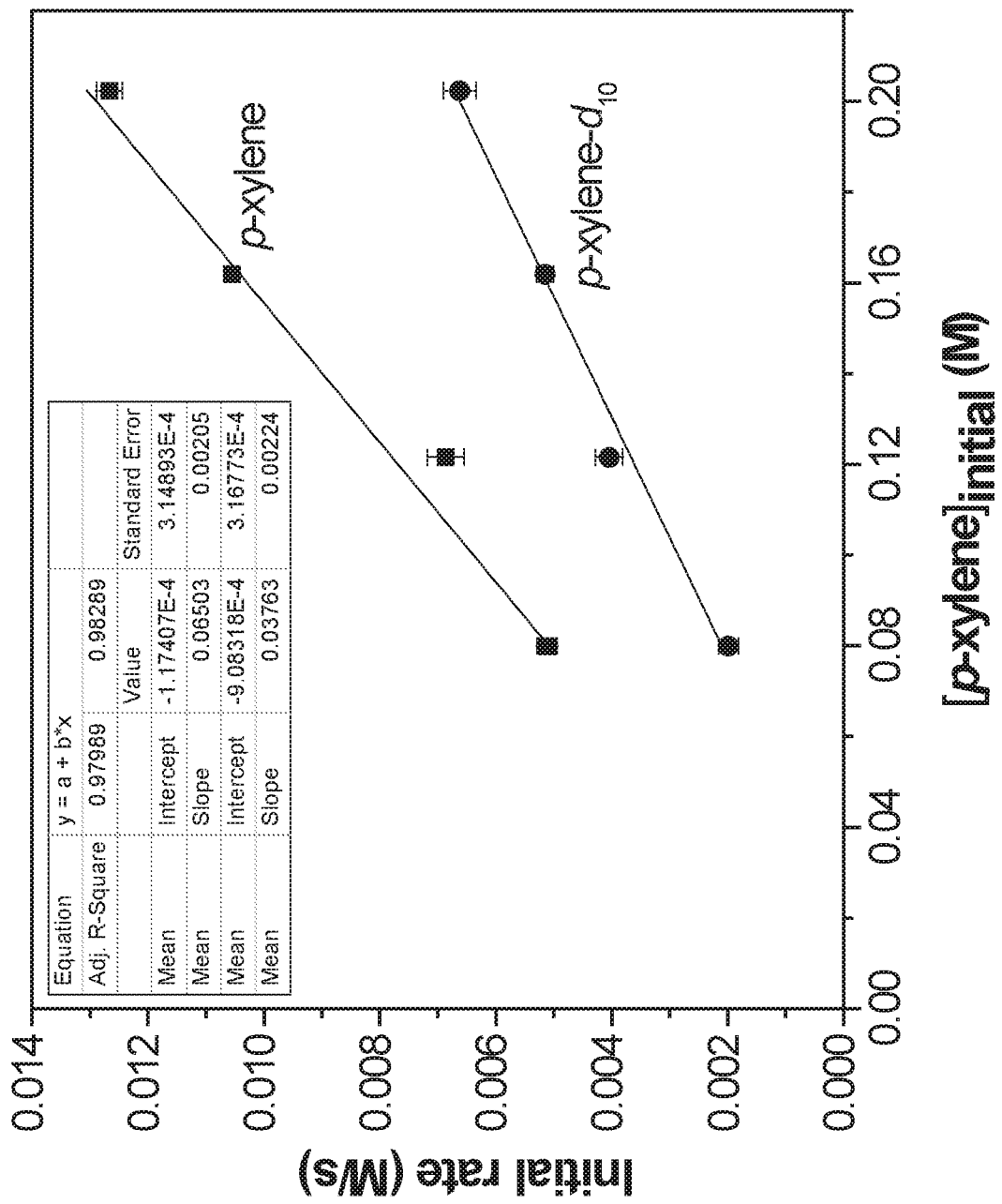
FIG. 6 is a graph showing the plot of initial rates (d[p-xylene]/dt) versus initial p-xylene concentration ([p-xylene]$_{initial}$ (<10% conversion) for benzylic C—H borylation of p-xylene and deuterated p-xylene (p-xylene-$d_{10}$) at 103 degrees Celsius (° C.) catalyzed by the post-synthetically metallated and activated metal organic framework described for FIG. 1 (i.e., UiO-68-Co). From the slopes of the two curves, the ratio of observed reaction rate constants for the two reactions ($k_{obs}^{(H)}/k_{obs}^{(D)}$) was calculated as 1.73.
Figure 7:
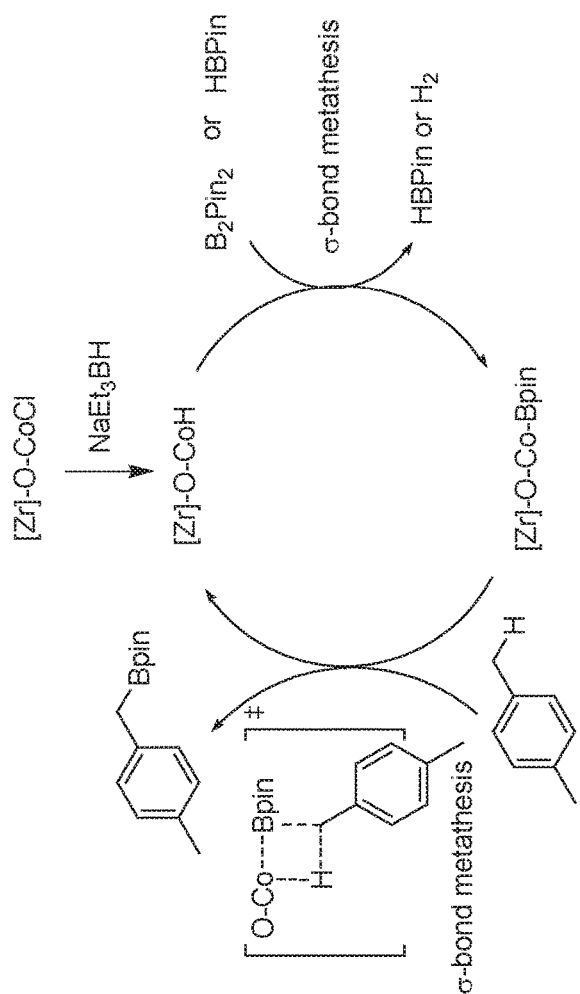
FIG. 7 is a schematic drawing showing the proposed mechanism for the metal organic framework (UiO-68-Co) catalyzed benzylic C—H borylation of alkyl-arenes with pinacolborane ($B_2pin_2$). The metalated metal organic framework is indicated by [Zr]—OCoCl and the activated catalyst is indicated by [Zr]—O—CoH.

UiO-68-Co(H) is believed to be the active catalyst for the reactions as evidenced by spectroscopic results and stoichiometric reactions. The reaction of UiO-68-Co(H) with HBpin readily generates UiO-68-Co(Bpin) and equiv amount of H$_2$, In addition, X-ray absorption near edge structure analysis (XANES) indicates that the Co centers in both UiO-68-Co (H) and UiO-68-Co(Bpin) are in +2 oxidation states. To further investigate the mechanism, the empirical rate law was determined by the method of initial rates (<10% conversion), which shows that the C—H borylation of p-xylene by UiO-68-Co has a first-order dependence on the catalyst and p-xylene concentrations, and a zeroth-order dependence on the B$_2$pin$_2$ concentration. See FIGS. 5A and 5B. Furthermore, the conversion of deuterated p-xylene was slower than proteo-p-xylene. Primary kinetic isotope effects from substrate conversion measurements $[k'_{obs}{}^{(H)}/k'_{obs}{}^{(D)}=1.73(9)]$ indicates that a C—H bond cleavage of p-xylene is the turnover-limiting step. See FIG. 6 Thus, without being bound to any one theory, based on the spectroscopic results as well as rate law and primary isotope effect, UiO-68-Co catalyzed benzylic borylation likely proceeds via four-centered turnover limiting step involving [2σ+2σ] cycloaddition of a 'Co-Bpin' bond with 'H—C' bond of p-xylene as shown in FIG. 7.

Example 4

Hydrogenation of Olefins with UiO-MOF-Co

General Procedure for MOF-Co Catalyzed Hydrogenation of Olefins:

In a nitrogen-filled glove box, UiO-68-MOF-CoCl (0.5 mg, 0.1 mol % Co) in 1.0 mL THF was charged into a glass vial. NaBEt$_3$H (10 μL, 1.0 M in THF) was then added to the vial and the mixture was stirred for 1 h. The solid was then centrifuged, washed with THF twice, and transferred to a glass vial in 0.5 mL THF. The olefin substrate (0.34 mmol) was added to the vial. Then the vial was placed in a Parr reactor which was sealed under a nitrogen atmosphere and charged with hydrogen to 40 bar. After stirring at room temperature for 12 h-3 d, the pressure was released and the MOF catalyst was removed from the reaction mixture via centrifugation. Mesitylene (internal standard) was added to the organic extracts and the yield of the product was determined by integrations of the product and mesitylene peaks in the $^1$H NMR spectra in CDCl$_3$.

Typical Procedure for UiO-68-MOF-Co Catalyzed Hydrogenation of trans-α-methylstilbene:

Scheme 5. UiO-68-MOF-Co Catalyzed Hydrogenation.

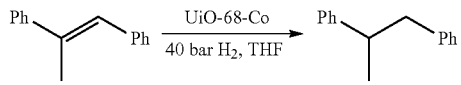

As shown in Scheme 5, above, in a glovebox, UiO-68-MOF-CoCl in THF (0.5 mg, 0.1 mol % Co) was charged into a small vial and 0.5 mL THF was added. Then, 10 μL NaBEt$_3$H (1.0 M in THF) was added to the vial and the mixture was stirred slowly for 1 h in the glovebox. The solid was centrifuged out of suspension and washed with THF two times. Then, the black solid in 0.5 mL THF was transferred to a vial containing 0.5 mL THF solution of trans-α-methylstilbene (65.9 mg, 0.34 mmol). The vial was placed into a Parr pressure reactor in a nitrogen-filled glovebox. The reactor was then pressurized to 40 bar. After stirring at room temperature for 2 d, the solid was centrifuged out of suspension and extracted three times with THF. The combined organic extracts were concentrated in vacuo to afford crude 1,2-diphenylpropane in quantitative yield, which was sufficiently pure as shown in a $^1$H NMR spectrum.

Test of "Heterogeneity" of the MOF Catalysis in Alkene Hydrogenation:

Scheme 6. Test of "heterogeneity" of MOF catalysis for alkene hydrogenation.

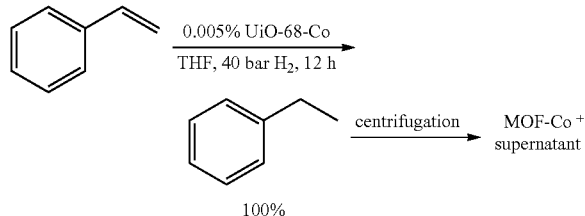

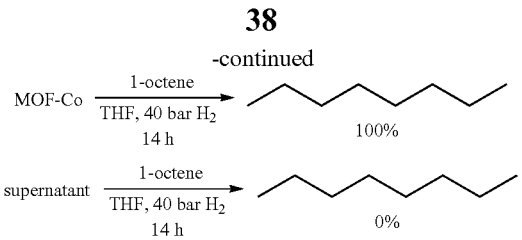

As shown in Scheme 6, above, in a nitrogen-filled glove box, UiO-68-MOF-CoCl (0.5 mg, 0.005 mol % Co) in 1.0 mL THF was charged into a glass vial. NaBEt$_3$H (15 μL, 1.0 M in THF) was then added to the vial and the mixture was stirred for 1 hour. The solid was then centrifuged, washed with THF twice, and transferred to a glass vial containing 0.5 mL THF. Styrene (0.71 g, 6.82 mmol) was then added to the vial. The vial was then placed in a Parr reactor which was sealed under nitrogen atmosphere and later charged with hydrogen to 40 bar. After 12 h, the pressure was released and the MOF catalyst was centrifuged out from suspension. Styrene was completely converted to ethylbenzene as determined by $^1$H NMR spectra based on the integration of substrate and product peaks in the crude.

After the solid and supernatant were separated, 1-octene (1.07 mL, 6.82 mmol) was added to each of the portions which were later placed in a Parr reactor, sealed under nitrogen and charged with hydrogen to 40 bar. After 14 h, the pressure was released and the supernatant was separated from the solid catalyst when necessary. Conversions of 1-octene to n-octane determined based on integration of substrate and product peaks in the crude $^1$H NMR spectra were 100% in the presence of MOF and 0% in the presence of supernatant, indicating that the MOF is the actual catalyst for alkene hydrogenation.

Reuse and Recycle Experiment Procedure for UiO-68-MOF-Co-Catalyzed Hydrogenation of 1-Octene:

Scheme 7. Reuse of UiO-68-MOF-Co in hydrogenation of 1-octene.

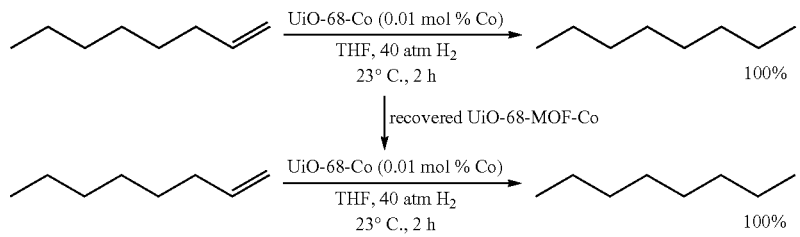

As shown in Scheme 7, in a glovebox, a vial was charged with UiO-68-MOF-Co (2.0 mg, 0.01 mol % Co) in 1 mL THF. 20 μL NaBEt$_3$H (1.0 M in THF) was added to the vial and the mixture was stirred slowly for 1 h in the glovebox. The solid was centrifuged out of suspension and washed with THF two times. Then, the solid in 1.0 mL THF was transferred to a vial and 1-octene (2 mL, 12.7 mmol) was added. The vial was placed into a Parr pressure reactor in a nitrogen-filled glovebox. The reactor was then pressurized to 40 bar. After 2 h, hydrogen was released and the solid was centrifuged out of suspension and extracted 2-3 times with THF in the glovebox. Quantitative yield of n-octane was obtained as determined by GC-MS and $^1$H NMR with mesitylene as the internal standard.

The recovered solid catalyst was added to a vial containing 1-octene (2 mL, 12.7 mmol) in 1.0 mL THF. The vial was placed into a Parr pressure reactor in a nitrogen-filled glovebox. The reactor was then pressurized to 40 bar. After 16 h, the solid was centrifuged out of suspension and extracted 2-3 times with THF in the glovebox. Product n-octane was obtained in quantitative yield as determined by GC-MS and $^1$H NMR with mesitylene as the internal standard. UiO-68-MOF-Co was recovered and reused at least 16 times without loss of catalytic activity.

Summary:

UiO-68-Co is active for catalytic hydrogenation of a range of olefins at room temperature. See Table 4. Monosubstituted alkenes such as 1-octene and styrene were readily hydrogenated in quantitative yields with turnover numbers (TONs)>1.0×10$^5$. See entries 1-2, Table 4. At 0.1-0.01 mol % Co-loading, UiO-68-Co catalyzed hydrogenation of 1,1-, cis-1,2-, α-isopropylstyrene and cyclohexene in quantitative yields. See entries 3-6, Table 4. Additionally, dialkenes, such as allyl ether, and trisubstituted alkenes, such as trans-α-methylstilbene, were completely hydrogenated by UiO-68-Co in excellent yields. See entries 7-8, Table 4. UiO-MOF-Co displayed a TON of 3.54×10$^6$ within 66 h in hydrogenation of 1-octene, which is the highest TON that has ever been reported for Co-catalyzed olefin hydrogenation. See entry 1, Table 4. In addition, the n-octane product contained only 3.7 ppm Co and 1.7 ppm Zr after simple filtration. MOF-Co catalysts are also tolerant of carbonyl groups. The functionalized alkene dimethyl itaconate was hydrogenated to dimethyl 2-methylsuccinate selectively in 91% yield. See entry 9, Table 4.

TABLE 4

UiO-68-MOF-Co-catalyzed hydrogenation of olefins.[a]

| Entry | Substrate | % Co-loading | Time | Yield (%) | TONs |
|---|---|---|---|---|---|
| 1 | 1-octene | 0.265 ppm | 66 h | 94 | 3.54 × 10$^6$ |
| 2 | Ph-CH=CH$_2$ | 0.001 | 7 h | 100 | >1.0 × 10$^5$ |
| 3 | Ph-C(Me)=CH$_2$ | 0.01 | 14 h | 100 | >10000 |
| 4 | Ph-CH=CH-CH$_3$ | 0.1 | 15 h | 100 | >1000 |
| 5 | α-isopropylstyrene | 0.1 | 12 h | 100 | >1000 |
| 6 | cyclohexene | 0.1 | 30 h | 100 | >1000 |
| 7 | Ph-C(Me)=CH-Ph | 0.002[b] | 3 d | 76 | 38000 |
| 8 | allyl ether | 0.1 | 3 d | 93 | 930 |
| 9 | dimethyl itaconate (MeOOC-C(=CH$_2$)-CH$_2$-COOMe) | 0.5 | 3 d | 91 | 182 |

[a]Reaction conditions: 1.0 mg of UiO-68-CoCl, 5 equiv of NaBEt$_3$H (1.0 M in THF) w.r.t. Co, alkene, THF, 40 bar H$_2$, 23° C.
[b]Reaction was performed at 60° C.

Figure 8:
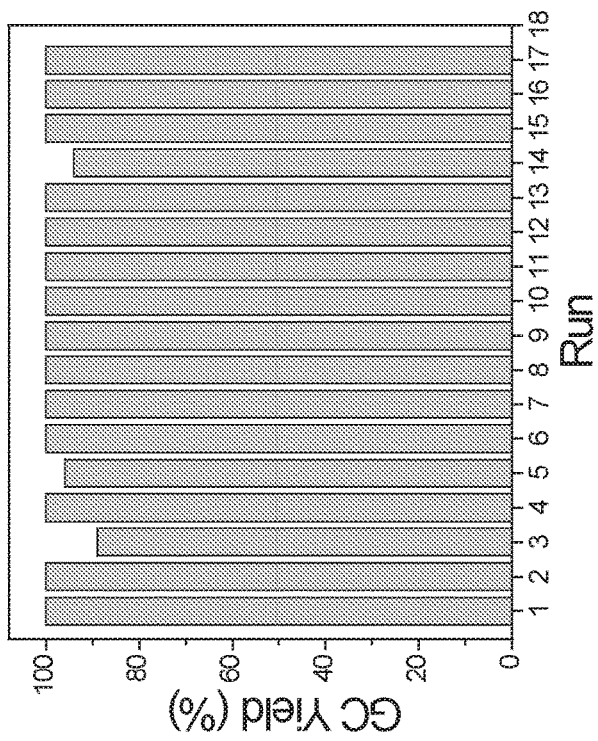
FIG. 8 is a graph showing the yields (% as measured by gas chromatography (GC)) of n-octane at different runs in the reuse study of a metal organic framework catalyst (UiO-68-Co) in the hydrogenation of 1-octene. The cobalt loadings were 0.01 mol %.

At 0.01 mol % Co loading, UiO-68-Co can be recovered and reused at least 16 times for the hydrogenation of 1-octene without loss of catalytic activity. See FIG. 8. Complete conversion was observed in every run without olefin isomerization or formation of other byproducts. PXRD patterns of the MOF catalysts after catalysis were identical to those of the pristine MOF catalysts, indicating the stability of the framework under catalytic conditions. Additionally, ICP-MS analyses of the organic product showed a negligible metal leaching after the 1$^{st}$ run, with the leaching of 0.85% Co and 0.98% Zr, respectively. A "cross" test further confirmed the heterogeneity of MOF-catalysts: after completely hydrogenating styrene in 12 h, UiO-68-Co was separated from the supernatant. An equal amount of 1-octene was added to the solid and supernatant, respectively. After 14 h under hydrogen atmosphere, 1-octene was completely converted to n-octane in presence of the MOF solid but no conversion was observed in the presence of the supernatant, indicating that the MOF-Co, not the leached species, was the active catalyst for hydrogenation.

Example 5

Hydroboration and Hydrosilylation with UiO-MOF-Co

General Procedures for Catalytic Hydroboration of Carbonyl Compounds:

In a glovebox, UiO-68-CoCl (1.0 mg, 0.01 mol % Ir) was charged into a small vial and 0.5 mL THF was added. Then, 8 μL NaBEt$_3$H (1.0 M in THF) was added to the vial and the mixture was stirred slowly for 1 h in the glovebox. The solid was centrifuged out of suspension and washed with THF two times. Then, THF was removed and aldehyde or ketone (6.78 mmol) and pinacolborane (7.40 mmol) was added. The resultant mixture was transferred to a Schlenk tube and then heated at 60° C. outside of the glovebox and the progress of the reaction was monitored by GC. After complete conversion, the solid was centrifuged out of suspension and extracted with hexane 2-3 times. The combined organic extracts were concentrated in vacuo to yield the pure product.

A Typical Procedure for UiO-68-Co Catalyzed Hydroboration of Ketones:

Scheme 8. UiO-68-Co catalyzed hydroboration of a ketone.

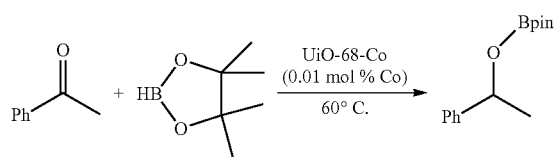

In a glovebox, UiO-68-CoCl (1.0 mg, 0.01 mol % Ir) was charged into a small vial and 0.5 mL THF was added. Then, 8 μL NaBEt$_3$H (1.0 M in THF) was added to the vial and the mixture was stirred slowly for 1 h in the glovebox. The solid was centrifuged out of suspension and washed with THF two times. Then, THF was removed and acetophenone (0.81 g, 6.78 mmol) and pinacolborane (0.95 g, 7.40 mmol) was added. See Scheme 8. The resultant mixture was transferred to a Schlenk tube and then heated at 60° C. outside of the glovebox for 2 d. Then, the solid was centrifuged out of suspension and extracted with hexane for 2-3 times. The combined organic extracts were concentrated in vacuo to yield the borate ester product as a colorless oil (1.63 g, 6.57 mmol, 96.9%). The crude borate ester was sufficiently pure for further use as shown by $^1$H NMR spectrum.

Summary:

The UiO-68-Co materials were evaluated for catalytic hydroboration and hydrosilylation of alkenes and carbonyl compounds. See Tables 5-7. The hydroboration reactions were performed by treating ketones or aldehydes with equimolar HBpin in presence of 0.01-0.0015 mol % UiO-68-Co at 60° C. See Table 5. 0.01 mol % UiO-68-Co afforded borate ester products from a range of carbonyl substrates, including alkyl- and alkoxy-functionalized aryl ketones and aldehydes in essentially quantitative yields. A TON of 54,000 was obtained for hydroboration of acetophenone. See entry 1, Table 5. Pure hydroboration products were obtained by simply removing the catalyst via centrifugation followed by removal of the organic volatiles.

TABLE 5

UiO-68-MOF-Co-catalyzed hydroboration of ketones and aldehydes.[a]

| Entry | Substrate | % Co-loading | Time | Yield (%) | TONs |
|---|---|---|---|---|---|
| 1 | Ph-C(O)-Me | 0.0015 | 5 d | 81 | 54000 |
| 2 | 4-Me-C$_6$H$_4$-C(O)-Me | 0.01 | 2 d | 100 (96) | >10000 |
| 3 | 4-MeO-C$_6$H$_4$-C(O)-Me | 0.01 | 2 d | 100 | >10000 |
| 4 | Et-C(O)-Me | 0.01 | 3 d | 100 (86) | >10000 |

TABLE 5-continued

UiO-68-MOF-Co-catalyzed hydroboration of ketones and aldehydes.[a]

| Entry | Substrate | % Co-loading | Time | Yield (%) | TONs |
|---|---|---|---|---|---|
| 5 | 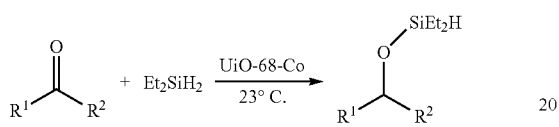 | 0.01 | 1 d | 100 (98) | >10000 |

[a]Reaction conditions: 0.5 mg of MOF-CoCl, 5 equiv of NaBEt$_3$H (1.0 M in THF) w.r.t. Co, carbonyl substrate (neat), HBpin, 60° C.

Scheme 9. Hydrosilylation of carbonyl compounds with UiO-68-MOF-Co.

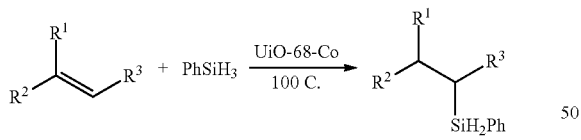

The UiO-68-MOF-Co catalyzed hydrosilylation of acetophenone was carried out using 0.5 mg of the MOF treated with 5 equivalents of NaBEt$_3$H (1.0 M in THF). As shown in Scheme 9, above, the neat substrate was reacted with Et$_2$SiH$_2$ at 23° C. Results are shown in Table 6, below.

TABLE 6

UiO-68-MOF-Co-catalyzed hydrosilylation of ketones and aldehydes.

| Entry | Substrate | % Co-loading | Time | Yield (%) | TONs |
|---|---|---|---|---|---|
| 1 | PhC(O)Me | 0.1 | 3 d | 100 | >1000 |

The hydrosilylation of alkenes catalyzed by UiO-68-Co was carried out at 100° C. for 5 days. See Scheme 10. Results are shown in Table 7.

Scheme 10. Hydrosilylation of alkenes using UiO-68-Co.

$$R^2\text{-CH=CR}^1R^3 + PhSiH_3 \xrightarrow[100\ C.]{UiO\text{-}68\text{-}Co} R^1R^2CH\text{-}CR^3(SiH_2Ph)$$

TABLE 7

UiO-68-MOF-Co-catalyzed hydrosilylation of alkenes[a].

| Entry | Substrate | Product | % Co-loading | Yield (%) | TONs |
|---|---|---|---|---|---|
| 1 | styrene | H$_2$Si(Ph)CH(Me)C$_6$H$_5$ | 0.1 | 81 | 810 |

TABLE 7-continued

UiO-68-MOF-Co-catalyzed hydrosilylation of alkenes[a].

| Entry | Substrate | Product | % Co-loading | Yield (%) | TONs |
|---|---|---|---|---|---|
| 2 |  | 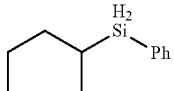 | 0.2 | 28 | 140 |
| 3 | 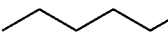 | 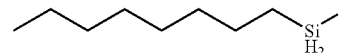 | 0.2 | 12 | 60 |

[a]Reaction conditions: 0.5 mg of MOF-CoCl, 5 equiv of NaBEt$_3$H (1.0 M in THF) w.r.t. Co, alkene substrate (neat), PhSiH3, 100° C.

Example 6

Regioselective Silylation with UiO-MOF-Co

Scheme 11. Benzylic C-H silylation of arenes using UiO-68-Co.

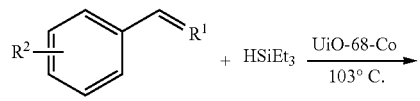

+ HSiEt$_3$ $\xrightarrow{\text{UiO-68-Co}}$ $103°$ C.

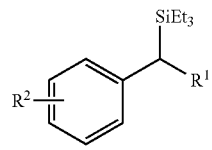

UiO-68-Co is also an active catalyst for regioselective silylation of benzylic C—H bonds without a directing group. See Table 8, below. The silylation reactions were performed with methylarenes (neat) and Et$_3$SiH under N$_2$ at 100° C. catalyzed by 0.2 mol % UiO-68-Co. See Scheme 11, above. Only benzylic silylated products were obtained from p-Xylene and mesitylene in good yields.

TABLE 8

UiO-68-MOF-Co-catalyzed undirected benzylic C—H silylation of arenes[a]

| Substrate | Product(s) | Time | % Conversion [Benzyl:Ar] |
|---|---|---|---|
| 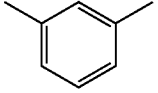 | 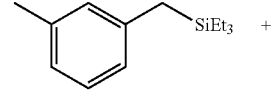 | 2.5 d | 100 [60:40] |
| 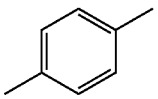 | 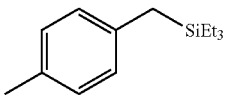 | 2 d | 76 |
| 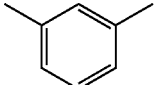 | 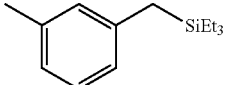 | 2 d | 89 |
| 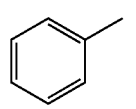 | 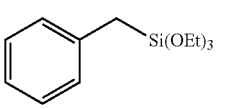 | 3 d | 89 |
| 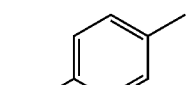 | 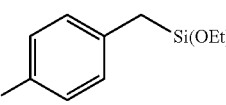 | 3 d | 52 |

[a]Reaction conditions: 1.0 mg of UiO-68-CoCl, 5 equiv NaBEt$_3$H (1.0 M in THF), arene, Et$_3$SiH or (EtO)$_3$SiH, 103° C., reflux under N$_2$.

Example 7

Amination with UiO-MOF-Fe

SBUs of UiO-68-MOF were also metalated with iron complexes such as FeBr$_2$. ICP-MS analysis of the digested UiO-68-Fe indicated 100% metalation of Zr—OH sites. The Fe-functionalized MOF is an active catalyst for benzylic and allylic C—H amination reactions. See Scheme 12, below.

Scheme 12. UiO-68-MOF-Fe catalyzed amination.

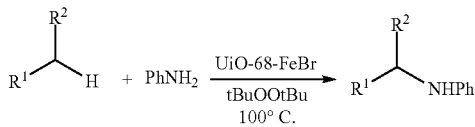

Typical Procedure for UiO-68-MOF-Fe Catalyzed Amination:

In a glovebox, UiO-68-MOF-Fe (8 mmol Co) was washed with THF two times and with tetrahydronaphthalene one time, and then transferred to a Schlenk tube, followed by addition of aniline (7.3 mL, 80 mmol) and peroxide (36.7 mL, 200 mmol). The tube was heated under nitrogen at 100° C. for 5 d. The reaction mixture was cooled to room temperature and the solid was centrifuged out of suspension. The extract was passed through a short plug of celite and then concentrated in vacuo to give crude reaction mixture, then analyzed by $^1$H-NMR using MeNO$_2$ as internal standard.

The treatment of aniline and ($^t$BuO)$_2$ with either tetrahydronaphthalene or ethylbenzene in presence of 2 mol % UiO-68-FeBr at 100° C. afforded the corresponding benzylic amine products in moderate yields. See Table 9.

TABLE 9

UiO-68-MOF-Fe-catalyzed Benzylic and Allylic C—H amination[a]

| Entry | Substrate | Product | Time | Yield (%) | TONs |
|---|---|---|---|---|---|
| 1 | | | 4 d | 49 | 25 |
| 2 | | | 2 d | 6 | 3 |
| 3 | | | 2 d | 41 | 21 |

[a]Reaction conditions: 8 μmol mg of MOF-FeBr w.r.t. Fe, C—H substrate (neat), tBuOOtBu (2.5 eq), 100° C.

Example 8

TPHN-MOF-Mq

TPHN-MOF-MgMe.

In a glovebox, Me$_2$Mg (2.5 mg) in 1.0 mL THF was added to a vial containing TPHN-MOF (15.0 mg) in 3 mL THF. The mixture was slowly stirred for 4 h and the yellow solid was then centrifuged out and washed with THF for 5-8 times. The metalated MOFs were then stored in THF in the glovebox for further uses.

Typical Procedure for TPHN-MOF-Mg Catalyzed Hydroamination of Aminoalkenes:

A J. Young style NMR tube with a resealable Teflon valve was charged with 2,2-diphenyl-4-penten-1-amine (23.0 mg, 0.097 mmol) and TPHN-MOF-Mg (1.0 mg, 1 mol % Mg) in 0.7 mL of benzene-d$_6$. The tube was sealed and then heated at 80° C. for two days until the reaction was completed as monitored by $^1$H NMR spectroscopy. Then, the solid was centrifuged out of suspension and extracted with benzene three times. The combined organic extracts were concentrated in vacuo to yield the pure 2-methyl-4,4-diphenylpyrrolidine as a colorless oil (21.6 mg, 0.091 mmol, 94.0%).

Typical Procedure for TPHN-MOF-Mg Catalyzed Hydroboration of Ketones.

Scheme 13. TPHN-MOF-Mg catalyzed hydroboration of ketones.

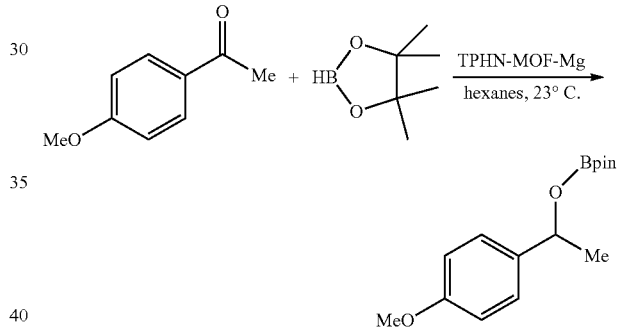

As shown in Scheme 13, in a glovebox, TPHN-MOF-MgMe (1.0 mg, 0.05 mol % Mg) in 1.0 mL hexanes was charged into a small vial. Then, 3.0 mL of a solution of 4-methoxyacetophenone (0.30 g, 2.0 mmol) and pinacolborane (342.5 mL, 2.19 mmol) was added. The resultant mixture was stirred slowly at room temperature within the glovebox for 2 d. Then, the solid was centrifuged out of suspension and extracted with hexane for 2-3 times. The combined organic extracts were concentrated in vacuo to yield the pure borate ester product (0.54 g, 1.96 mmol, 98.0%).

Recycling of TPHN-MOF-Mg in Hydroboration of Acetophenone:

Scheme 14. Recycling of TPHN—MOF—Mg.

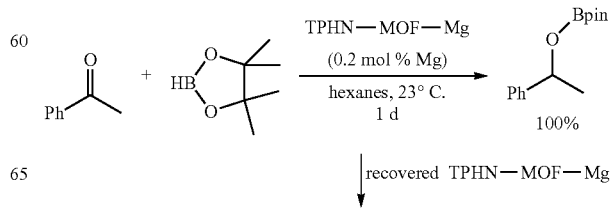

-continued

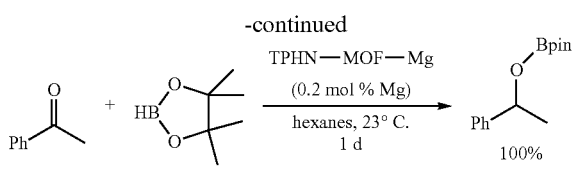

The recycling of the TPHN-MOF catalyst was studied as shown in Scheme 14. In a glovebox, TPHN-MOF-MgMe (2.0 mg, 0.2 mol % Mg) in 1.0 mL hexanes was charged into a small vial. Then, 2.0 mL of a solution of acetophenone (0.12 g, 1.0 mmol) and pinacolborane (172.0 mL, 1.10 mmol) was added. The resultant mixture was stirred slowly at room temperature within the glovebox for 24 h. Then, the solid was centrifuged out of suspension and extracted with hexane for three times. The combined organic extracts were concentrated in vacuo to yield the pure borate ester product (0.248 g, 1.0 mmol, 100.0%).

The recovered solid catalyst in 1.0 mL hexanes was charged into a small vial. Then, 2.0 mL of a solution of acetophenone (0.12 g, 1.0 mmol) and pinacolborane (172.0 mL, 1.10 mmol) was added. The resultant mixture was stirred slowly at room temperature within the glovebox for 24 h. Then, the solid was centrifuged out of suspension and extracted with hexane three times. The combined organic extracts were concentrated in vacuo to yield the pure borate ester product (0.247 g, 0.995 mmol, 99.5%).

Figure 9:
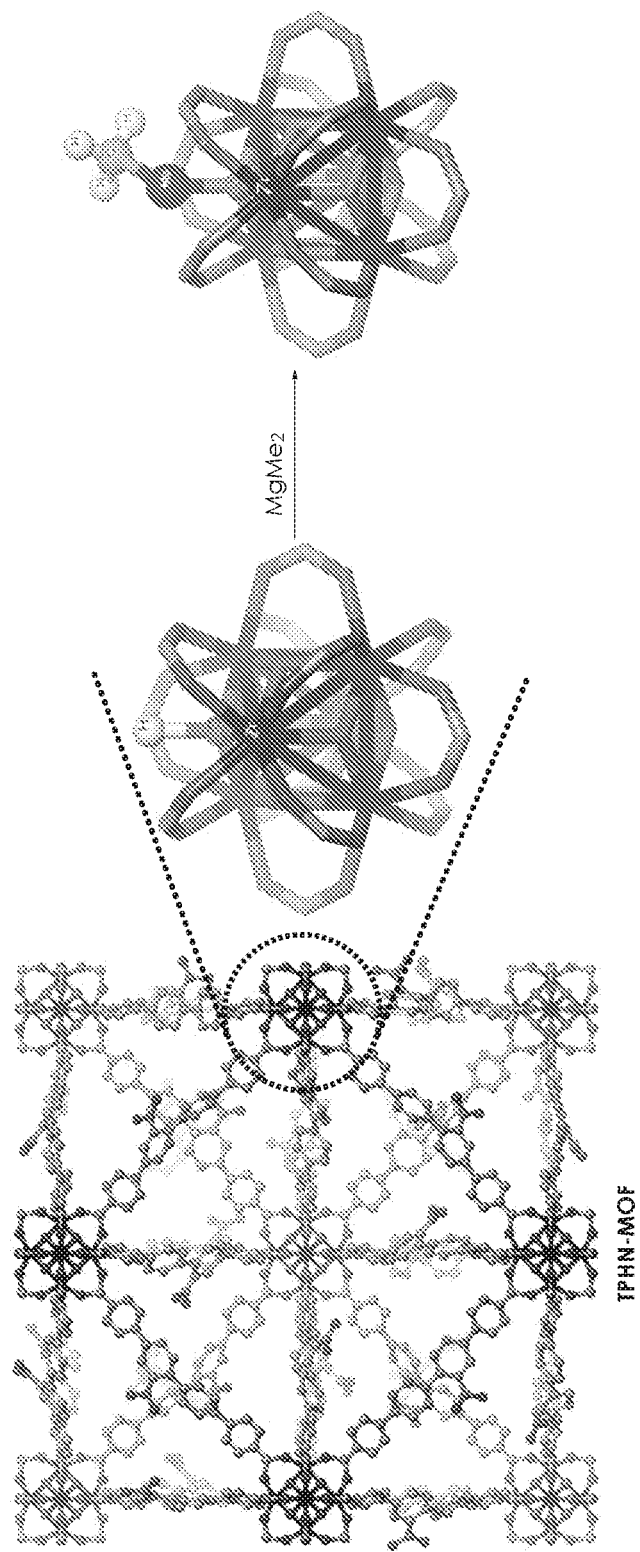
FIG. 9 is a schematic drawing of the post-synthetic metalation of secondary building units (SBUs) in a metal organic framework (MOF) prepared from 4,4'-bis(carboxyphenyl)-2-nitro-1,1'-biphenyl (TPHN) as an organic bridging ligand and zirconium (Zr) oxo clusters (i.e., TPHN-MOF). The post-synthetic metalation of the TPHN-MOF is performed with dimethyl magnesium ($Me_2Mg$) by a protonolysis route.
Figure 10B:
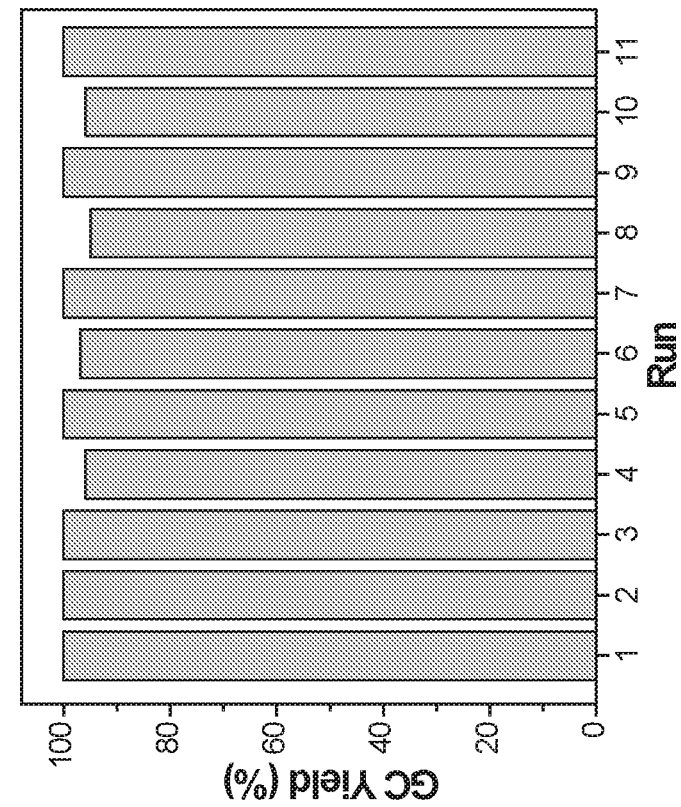
FIG. 10B is a graph showing the plot of yields (% as determined by gas chromatography (GC)) of borate ester at different runs in the reuse study of the catalyst (TPHN-MOF-Mg) prepared from the metal organic framework described in FIG. 9.
Figure 10A:
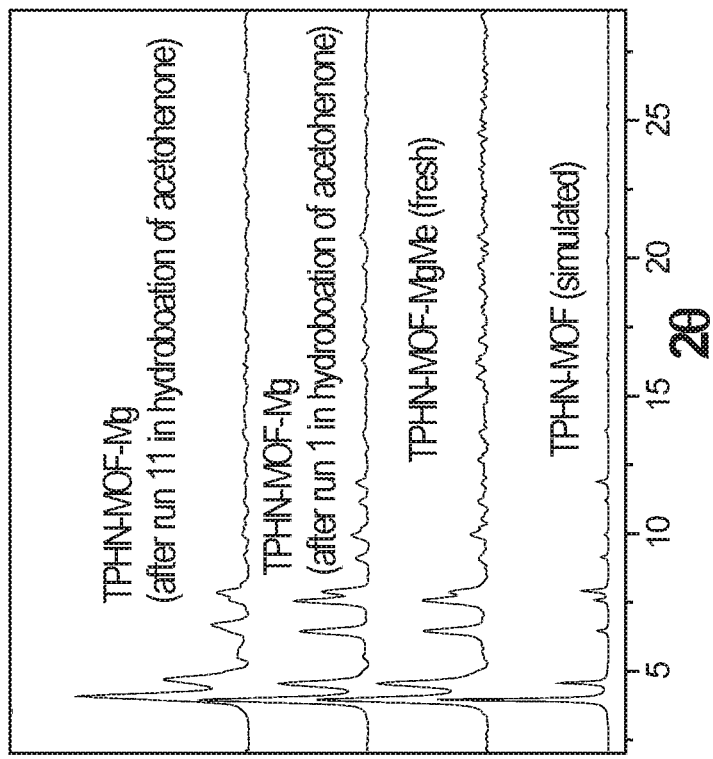
FIG. 10A is a graph showing the powder x-ray diffraction (PXRD) patterns simulated for the metal organic framework (MOF) described for FIG. 9 prior to post-synthetic metallation (TPHN-MOF (simulated)), experimentally determined for the MOF after the post-synthetic metalation shown in FIG. 9 (TPHN-MOF-MgMe (fresh)), experimentally determined for the metalated MOF after recovery from one use as a catalyst for the hydroboration of acetophenone (TPHN-MOF-Mg (after run 1 in hydroboration of acetophenone)), and experimentally determined for metalated MOF after recovery from eleven uses as a catalyst for the hydroboration of acetophenone (TPHN-MOF-Mg (after run 11 in hydroboration of acetophenone)). The PXRD patterns for the recovered MOF catalysts indicate the retention of crystallinity after post-synthetic metalation and catalysis.

Summary:

TPHN-MOF (TPHN=4,4'-bis(carboxyphenyl)-2-nitro-1, 1'-biphenyl) built from Zr-oxo clusters and a TPHN-derived bridging ligand was prepared and then the SBUs of the TPHN-MOF were metalated with Mg complexes via a protonolysis route. The reaction of $Me_2Mg$ with TPHN-MOF in THF at room temperature afforded TPHN-MOF-MgMe. See FIG. 9. PXRD studies indicated that TPHN-MOF remained crystalline after metalation (see FIG. 10A) and ICP-MS analysis showed 100% loading of Mg w.r.t. Zr—OH.

TPHN-MOF-MgMe can be an active precatalyst for intramolecular hydroamination/cyclization of aminoalkenes to cyclic amines, as shown in Scheme 15, below. At 1.0 mol % Mg loading, several 3,3'-disubstituted aminopentenes were readily converted to the corresponding 2-methyl-pyrrolidines in quantitative yields. See Table 10. In addition, the hydroboration of carbonyl compounds were catalyzed efficiently by TPHN-MOF-Mg with TON>10000. See Table 11 and Scheme 16. TPHN-MOF-Mg can be recycled and reused at least 10 times for the hydroboration of acetophenone (see FIG. 10B) and the MOF remained crystalline even after run 11. See FIG. 10A.

Scheme 15. TPHN—MOF—Mg catalyzed hydroaminoiation/cyclization of aminoalkenes.

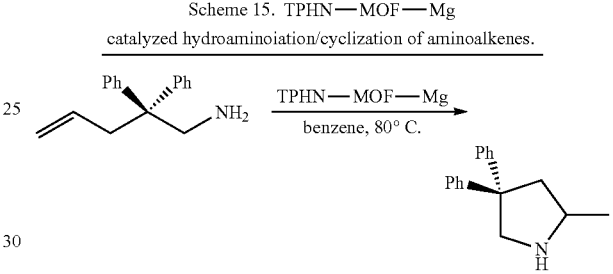

TABLE 10

TPHN-MOF-Mg-catalyzed hydroamination/cyclization of aminoalkenes.[a]

| Entry | Substrate | Product | Time | Yield (%) |
|---|---|---|---|---|
| 1 | Ph, Ph, NH₂ | Ph, Ph, N-H | 2 d | 100 |
| 2 | Ph, NH₂ (diallyl) | Ph, N-H (allyl) | 2 d | 100 |
| 3 | triallyl NH₂ | diallyl N-H | 2 d | 100 |

[a]Reaction conditions: 1.0 mg of TPHN-MOF-Mg, aminoalkene, benzene, 80° C.

Scheme 16. TPHN—MOF—Mg catalyzed hydroboration of carbonyl compounds.

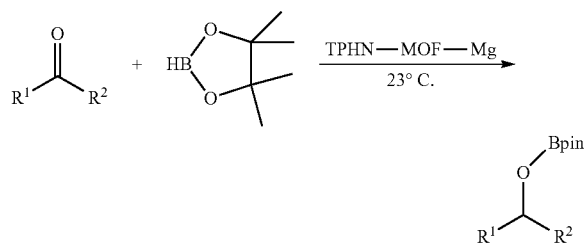

TABLE 11

TPHN-MOF-Mg (TPHN = 4,4'-bis(carboxyphenyl)-2-nitro-1,1'-biphenyl) catalyzed hydroboration of ketones and aldehydes.[a]

| Substrate | % Co-loading | Time | Yield (%) | TONs |
|---|---|---|---|---|
| PhC(O)Me | 0.05 | 24 h | 100 | >2000 |
| 4-MeC6H4C(O)Me | 0.05 | 18 h | 100 | >2000 |
| 4-MeOC6H4C(O)Me | 0.05 | 2 d | 100 | >2000 |
|  | 0.01 | 5 d | 100 | >10000 |
| Et-C(O)-Me | 0.1 | 1 d | 100 | >1000 |
| 4-ClC6H4CHO | 0.05 | 3 d | 100 (96) | >2000 |

[a]Reaction conditions: 1.0 mg of MOF-MgMe, carbonyl substrate (neat), HBpin, 23° C.

Example 9

Ce-UiO-67-Co

Ceria-based MOFs with UiO-67 topology were prepared. The Ce-UiO-67 was built from $Ce_6O_4(OH)_4(O_2CR)_{12}$ (i.e. as the SBU) and (1,1'-biphenyl)-4,4'-dicarboxylate bridging linkers. Similar to UiO-68 MOF, the SBUs of Ce-UiO-67 were easily metalated with $CoCl_2$ by treatment with nBuLi followed by reaction of $CoCl_2$. Upon treatment of $NaEt_3BH$, Ce-UiO-67-Co was an active catalyst for benzylic C—H borylation of methylarenes.

Example 10

General Methods for Examples 11-16

All of the reactions and manipulations were carried out under nitrogen with the use of standard inert atmosphere and Schlenk technique unless otherwise indicated. All solvents used were dry and oxygen-free. All of the alkene substrates were purchased from Fisher (Thermo Fisher Scientific, Waltham, Mass., United States of America) and distilled and dried over 4 Å molecular sieves prior to use. Benzene and tetrahydrofuran were degassed by sparging with nitrogen, filtered through activated alumina columns, and stored under $N_2$. Allyl ether, allyl acetate, α-terpinene and benzaldehyde were distilled and then dried over freshly activated 4 Å molecular sieves prior to use. Diethyldiallylmalonate, 2-vinylpyridine, allyltrimethylsilane, 2,3-dimethyl-2-butene, 1-methylcyclohexene, ethyl-3,3-dimethylacrylate, acetophenone, 6-methyl-5-hepten-2-one, cyclohexanone, quinoline, 6-methylquinoline, 6-methoxyquinoline, 2,6-dimethylquinoline, 2-methyl-6-fluoro-quinoline and benzofuran were purchased from Fisher (Thermo Fisher Scientific, Waltham, Mass., United States of America) and were degassed and then dried with freshly activated 4 Å molecular sieves in a glovebox prior to use. Imines were synthesized according to previously published procedures. See Xin et al., Chemistry—A European Journal, 2014, 20, 7926-7930; and Liu et al., Chemical Communications, 2011, 47, 10148-10150. All of the other substrates and reagents are commercially available and were used as received unless otherwise indicated.

$^1$H NMR spectra were recorded on a Bruker NMR 400 DRX spectrometer (Bruker Corporation, Billerica, Mass., United States of America) at 400 MHz and referenced to the proton resonance resulting from incomplete deuteration of deuterated chloroform (δ 7.26) or deuterated DMSO (δ 2.50). Thermogravimetric analysis (TGA) was performed in air using a Shimadzu TGA-50 (Shimadzu Corporation, Kyoto, Japan) equipped with a platinum pan. Powder X-ray diffraction (PXRD) patterns were collected on a Bruker D8 Venture, dual microsource (Cu and Mo) diffractometer (Bruker Corperation, Billerica, Mass., United States of America) with a CMOS detector. Cu Kα radiation was used. PXRD patterns were processed with APEX 2 package using a PILOT plug-in. Background diffraction signals from a glass capillary tube and solvent at 2θ~20° were simulated and removed from our analysis using the program PowderX. ICP-MS data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a $^{159}$Tb internal standard against a six-point standard curve over the range of 0.1 ppb to 1000 ppb. The correlation coefficient was >0.9997 for all analytes of interest. Data collection was performed in Spectrum Mode with five replicates per sample and 100 sweeps per replicate.

Example 11

Synthesis and Characterization of Zr-MTBC

Figure 11:
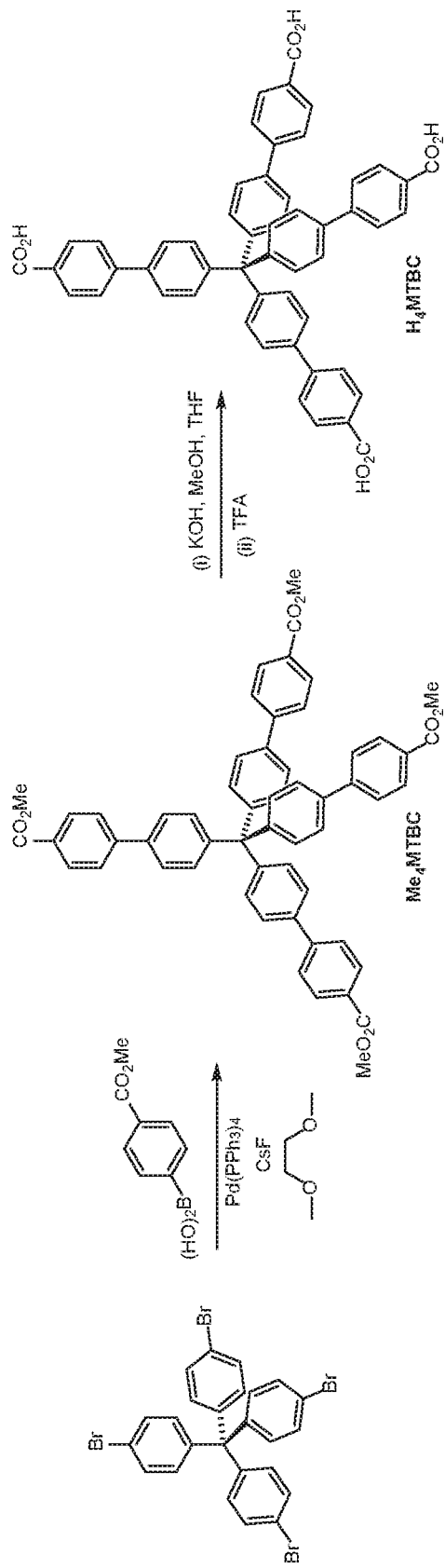
FIG. 11 is a schematic drawing showing the preparation of protonated form, i.e., methane tetrakis(p-biphenylcarboxylic acid) ($H_4MTBC$), of a tetrahedral organic bridging ligand, starting from tetrakis(4-bromophenyl)methane, via a tetra-methyl ester intermediate (i.e., $Me_4MTBC$).

Ligand Synthesis:

The $H_4$MTBC bridging ligand was prepared in two steps as shown in FIG. 11. First, the intermediate tetramethyl 4',4''',4''''',4'''''''-methanetetrayltetrakis([1,1'-biphenyl]-4-carboxylate) ($Me_4$MTBC) (CAS: 1208241-39-7) was synthesized using a modified procedure from the literature.

Tetrakis(4-bromophenyl)methane (723 mg, 1.14 mmol, 1 equiv.), Pd(PPh$_3$)$_4$ (132 mg, 0.114 mmol, 0.1 equiv.), 4-(methoxycarbonyl)phenylboronic acid (1.23 g, 6.82 mmol, 6 equiv.) and CsF (3.11 g, 20.46 mmol, 18 equiv.) were charged in a 120 mL high-pressure reaction tube and pumped into an N$_2$ glove box. To the reaction tube was added 60 mL of degassed dimethoxyethane, and the tube was capped and stirred at 85° C. for 3 days. Progress of the reaction was monitored by thin layer chromatography (TLC) (1% EtOAc/CHCl$_3$). After cooling to room temperature, the reaction mixture was transferred to a round-bottom flask and evaporated with a rotavap. The resulting solid was dissolved with CHCl$_3$ and filtered through celite to remove CsF and Pd nanoparticles. The filtrate was evaporated with a rotavap, then purified by flash column chromatography on silica gel using 1% EtOAc/Hexane as eluent to give white solid as pure product (572 mg, 59% yield). $^1$H NMR (500 MHz, CDCl$_3$): δ 8.10 (d, $^3J_H$=8.3 Hz, 8H), 7.68 (d, $^3J_{HH}$=8.3 Hz, 8H), 7.59 (d, $^3J_{HH}$=8.4 Hz, 8H), 7.44 (d, $^3J_{HH}$=8.5 Hz, 8H), 3.94 (s, 12H).

To prepare 4',4''',4''''',4'''''''-methanetetrayltetrakis(([1,1'-biphenyl]-4-carboxylic acid)) (H$_4$MTBC) (CAS: 1208241-38-6), Me$_4$MTBC (367 mg, 0.428 mmol) was suspended in THF (65 mL). A solution of KOH (6.17 g, 110 mmol) dissolved in MeOH (20 mL) was then added, and the reaction mixture was stirred at 60° C. for 24 h. The suspension was cooled to room temperature and the resulting precipitate was collected by centrifugation. The solution was washed with dry THF (20 mL) and recollected by centrifugation. The solid was suspended in THF (20 mL) and trifluoroacetic acid (3 mL) was slowly added and stirred for 1.5 h at room temperature. H$_2$O (15 mL) was then added, and the white solid was isolated by centrifugation, subsequently washed with THF and Et$_2$O, and dried in vacuo to obtain 4',4''',4''''',4'''''''-methanetetrayltetrakis(([1,1'-biphenyl]-4-carboxylic acid)) (331.9 mg, 1.04 mmol, 86% yield) as a pale-white solid. $^1$H NMR (500 MHz, DMSO-d$_6$): δ 12.98 (s, 4H), 8.02 (dd, $^3J_{HH}$=12.6, $^4J_{HH}$=8.4 Hz, 8H), 7.84 (dd, $^3J_{HH}$=16.9, $^4J_{HH}$=8.3 Hz, 8H), 7.78 (dd, $^3J_{HH}$=8.5, $^4J_{HH}$=4.3 Hz, 8H), 7.43 (d, 3J$_{HH}$=7.9 Hz, 8H).

Zr-MTBC Synthesis:

To a 50 mL flask was added ZrCl$_4$ (91.0 mg, 0.390 mmol), H$_4$MTBC (80 mg, 0.1 mmol), benzoic acid (2.77 g, 22.7 mmol), and DEF (16 mL, 6.25 mM to H$_4$MTBC). The mixture was sonificated for 5 min until all solids were dissolved. The 16 mL solution obtained was heated at 120° C. on a hotplate and stirred at 250 rpm for 24 h. The amount of Zr-MTBC (90 mg, 87% yield) was determined after drying MOF on a filter paper. The powder X-ray diffraction (PXRD) pattern of the obtained MOF was compared to that of a simulated pattern from a single crystal structure to show the good crystallinity of the Zr-MTBC. Hf-MTBC was also obtained using an analogous method.

Thermogravimetric Analysis:

The first weight loss (57.4%) in the 25-420° C. temperature range corresponds to removal of adsorbed solvents in the pores. The second weight loss (74.7%) in the 420-800° C. temperature range corresponds to decomposition of the MOF to ZrO$_2$, consistent with a calculated weight loss of 74.5% based on [Zr$_6$O$_4$(OH)$_4$(L)$_3$]$_6$[Zr$_8$O$_8$(OH)$_4$(L)$_3$]$_2$ to (ZrO$_2$)$_{52}$.

Crystallographic Data of M-MTBC (M=Zr or Hf):

Single crystal X-ray diffraction of M-MTBC was performed with a Bruker APEX II CCD-based detector (Bruker Corporation, Billerica, Mass., United States of America) at ChemMatCARS (Sector 15), Advanced Photon Source (APS), Argonne National Laboratory. Data were scaled and corrected for absorption effects using the multi-scan procedure as implemented in SADABS (Bruker AXS, version 2014/5, 2015, part of Bruker APEX3 software package). The structure was solved by SHELXT (Version 2014/5) (see Sheldrick, Acta Crystallographica Section C, 2015, 71; 3-8) and refined by a full-matrix least-squares procedure using OLEX2 software packages (XL refinement program version 2014/7). See Dolomanov et al., Journal of Applied Crystallography, 2009, 42, 339-341; and Sheldrick, Acta Crystallographica Section A, 2008, 64, 112-122. Crystallographic data and details of the data collection and structure refinement are listed in Table 12.

TABLE 12

Crystallographic information.

| Name | Zr-MTBC | Hf-MTBC |
|---|---|---|
| Formula | C$_{318}$H$_{144}$O$_{66}$Zr$_{13}$ | C$_{318}$H$_{144}$O$_{66}$Hf$_{13}$ |
| Fw | 6206.19 | 7195.55 |
| Temperature (K) | 100 | 100 |
| Wavelength (Å) | 0.41328 | 0.668 |
| Crystal System | Cubic | Cubic |
| Space Group | Pm$\bar{3}$n | Pm$\bar{3}$n |
| a, Å | 41.512(4) | 41.516(2) |
| b, Å | 41.512(4) | 41.516(2) |
| c, Å | 41.512(4) | 41.516(2) |
| α, ° | 90 | 90 |
| β, ° | 90 | 90 |
| γ, ° | 90 | 90 |
| V, Å$^3$ | 71535.21 | 71556.10 |
| Z | 4 | 4 |
| Density (calcd. g/cm$^3$) | 0.576 | 0.668 |
| Absorption coeff. (mm$^{-1}$) | 0.287 | 0.460 |
| F(000) | 12400.0 | 13488.0 |
| θ range data collection | 1.097-26.396 | 0.638-13.369 |
| Limiting indices | −44 <= h <= 50 | −43 <= h <= 46 |
| | −36 <= k <= 51 | −34 <= k <= 46 |
| | −50 <= l <= 50 | −46 <= l <= 45 |
| Reflections collected | 12692 | 9175 |
| Independent reflections | 6116 | 7375 |
| R(int) | 0.257 | 0.169 |
| Data/restraints/parameters | 12692/621/298 | 9175/623/310 |
| Goodness-of-fit on F$^2$ | 1.122 | 1.244 |
| Final R indices [I > 2σ(I)] | R1 = 0.126, wR2 = 0.3136 | R1 = 0.1145, wR2 = 0.2758 |
| R indices (all data) | R1 = 0.2586, wR2 = 0.3628 | R1 = 0.1540, sR2 = 0.3046 |

Figure 12A:
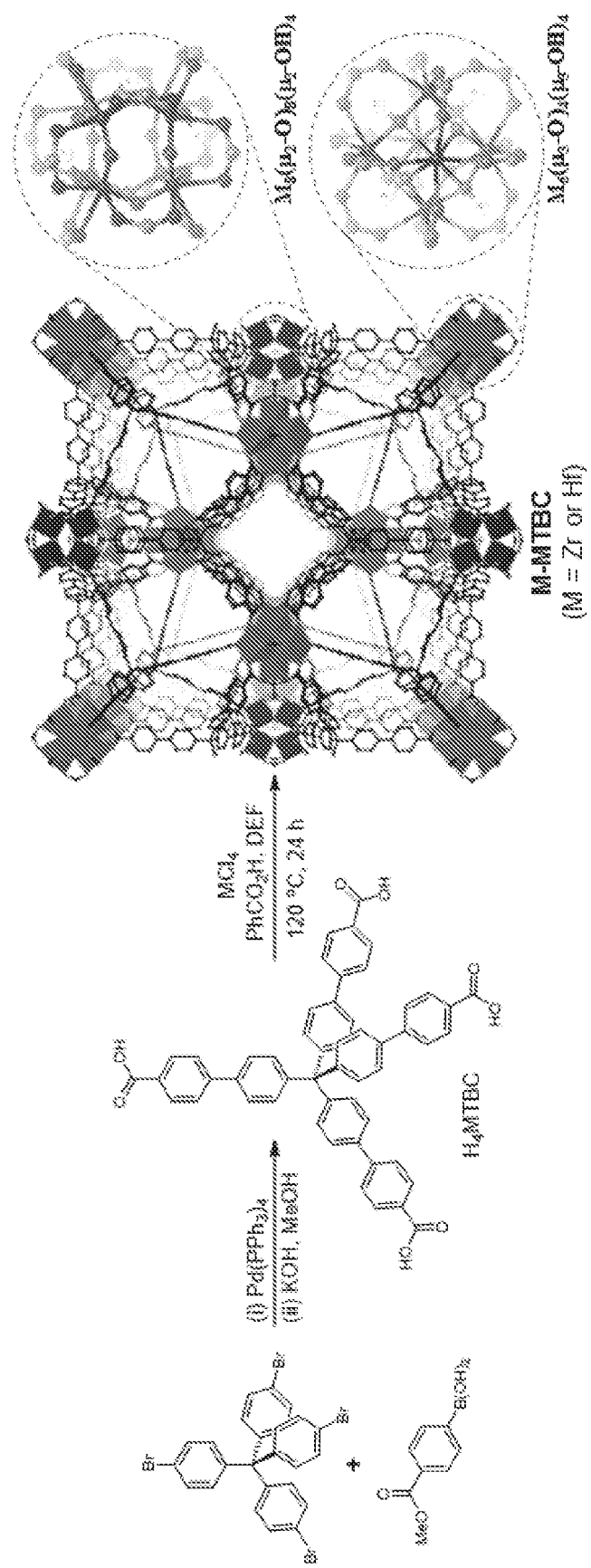
FIG. 12A is schematic drawing showing the synthesis of a metal organic framework comprising methane tetrakis(p-biphenylcarboxylate) (MTBC) organic bridging ligands and a zirconium (Zr)- or hafnium (Hf)-oxo cluster secondary building unit (SBU), M-MTBC.
Figure 12B:
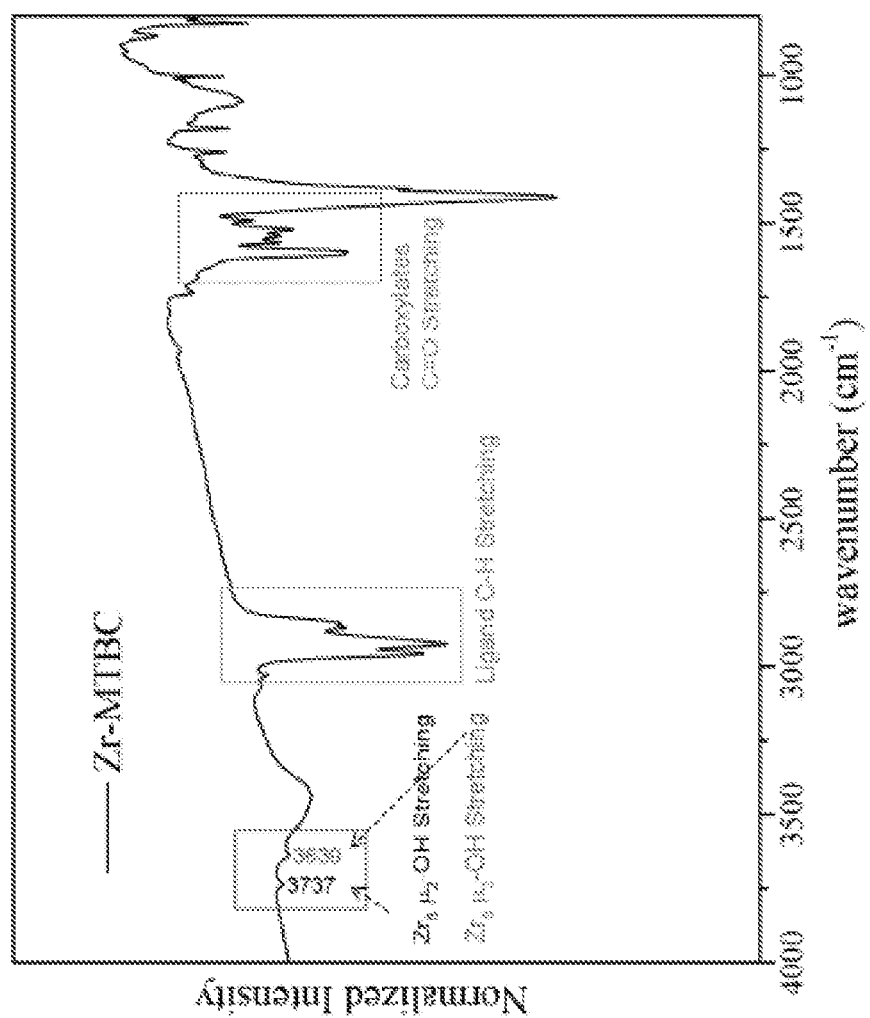
FIG. 12B is a graph showing the infrared (IR) spectrum of the zirconium (Zr) form (Zr-MTBC) of the metal organic framework described for FIG. 12A showing stretching vibrations of $\mu_3$-OH at 3639 wavenumbers ($cm^{-1}$) and $\mu_2$-OH at 3737 $cm^{-1}$ from the $Zr_8$ secondary building units.
Figure 12D:
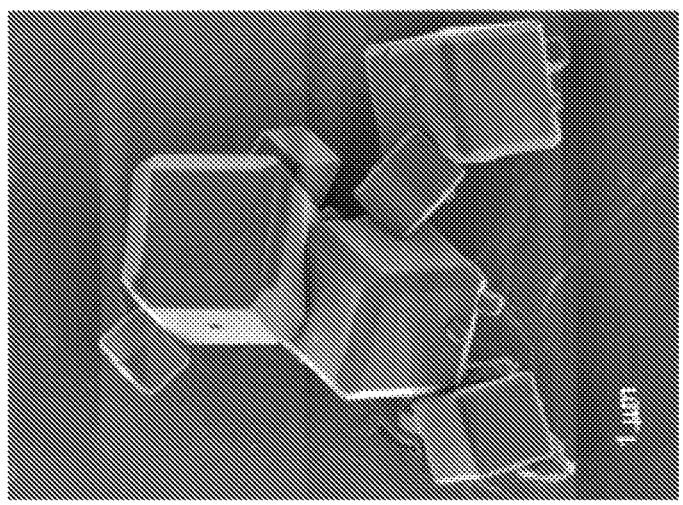
FIG. 12D is a scanning electron microscopy (SEM) image of the zirconium form (Zr-MTBC) of the metal organic framework described for FIG. 12A.
Figure 12C:
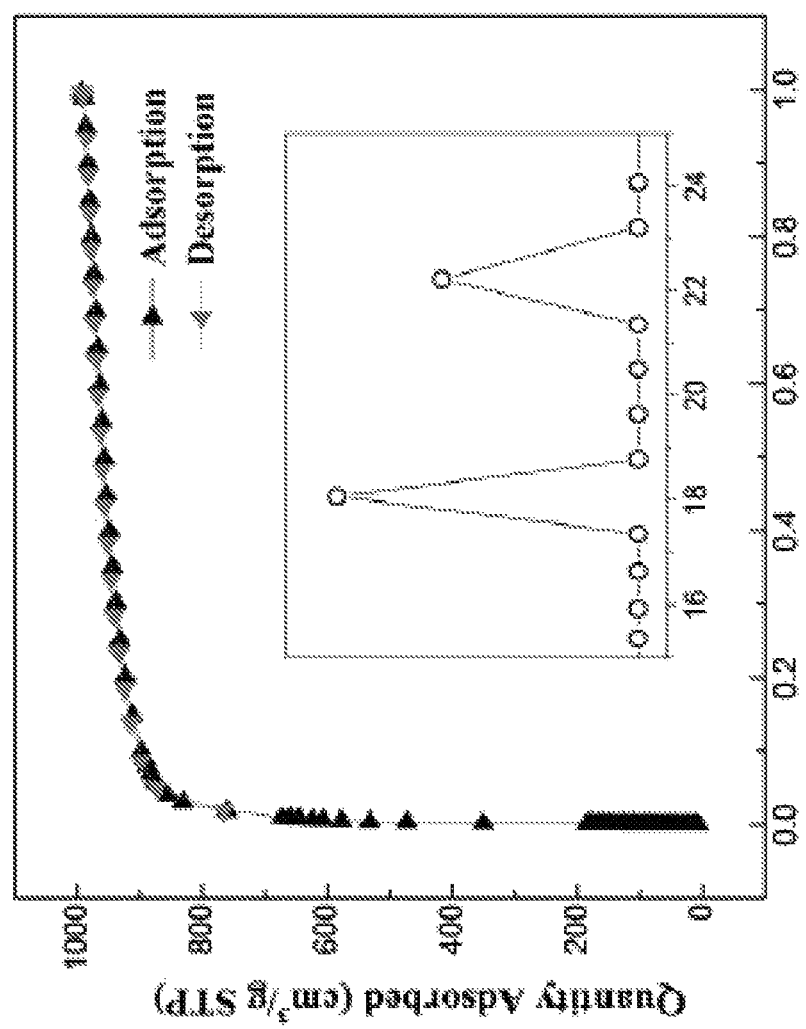
FIG. 12C is a graph showing the nitrogen sorption isotherms of the zirconium form (Zr-MTBC) of the metal organic framework described for FIG. 12A at 77 Kelvin (K). The inset shows the pore size distribution.

Summary:

Zr-MTBC was synthesized in 54% yield via a solvothermal reaction between ZrCl$_4$ and 4',4''',4''''',4'''''''-methanetetrayltetrakis([1,1'-biphenyl]-4-carboxylic acid) (H$_4$MTBC) in DEF using benzoic acid as modulator. A single-crystal X-ray diffraction study of Zr-MTBC indicated that Zr-MTBC crystallizes in the cubic pm-3n space group and revealed the presence of two types of SBUs, Zr$_8$(μ$_2$-O)$_8$(μ$_2$-OH)$_4$ and the Zr$_6$(μ$_3$-O)$_4$(μ$_3$-OH)$_4$ in 1:3 ratio. See FIG. 12A. This is believed to be the first synthesis of a Zr$_8$(μ$_2$-O)$_8$(μ$_2$-OH)$_4$ SBU as either a discrete cluster or as a structural unit in a MOF. In the Zr$_8$(μ$_2$-O)$_8$(μ$_2$-OH)$_4$ SBU, eight Zr$^{IV}$ ions occupy the eight corners of the cube, while eight μ$_2$-oxo and four μ$_2$-OH occupy the twelve edges of the cube. The Zr$_6$(μ$_3$-O)$_4$(μ$_3$-OH)$_4$ unit is isostructural to the SBU of UiO-MOF, with six Zr$^{IV}$ ions occupying six corners of an octahedron that are held together by four μ$_3$-oxo and four μ$_3$-OH groups at eight faces of the octahedron. Solid state infrared spectrum (IR) spectrum showed the presence of both the ν$_{μ2O-H}$ stretching band at 3737 cm$^{-1}$ and ν$_{μ3O-H}$ stretching band at 3639 cm$^{-1}$. See FIG. 12B. The void space was calculated to be 73.53% by PLATON. The MOF possessed two kinds of trigonal-bipyramid cavities of dimensions 24.9 Å×21.6 Å×35.9 Å and 20.8 Å×20.8 Å×13.1 Å, respectively. $N_2$ adsorption isotherm of Zr-MTBC showed a type I adsorption (77K, 1 bar) with Brunauer-Emmett-Teller (BET) surface area of 3700 m$^2$/g. See FIG. 12C. SEM image showed cubic particles of 1-3 μm in length. See FIG. 12D.

The Hf-MTBC analog was synthesized similarly and characterized by single-crystal X-ray diffraction.

Example 12

Synthesis and Characterization of Zr-MTBC-CoCl

Synthesis of Zr-MTBC-CoCl

In a glovebox, Zr-MTBC (45 mg) in 4 mL THF was cooled to −30° for 30 min. To the cold suspension, nBuLi (2.5 M in hexanes, 0.2 mL, 10 equiv. to μ-OH) was added dropwise and the resultant light green-yellow mixture was stirred slowly overnight at room temperature. The light yellow solid was collected after centrifugation, and washed with THF 5-6 times over 6 h. Then, the lithiated Zr-MTBC was transferred to a vial containing 4 mL THF solution of $CoCl_2$ (10.1 mg, 1.5 equiv. to μ-OLi). The mixture was stirred for 15 h and the deep blue solid was then centrifuged and washed with THF 5-8 times. The metalated MOFs were stored in THF in the glovebox for further use.

Figure 13:
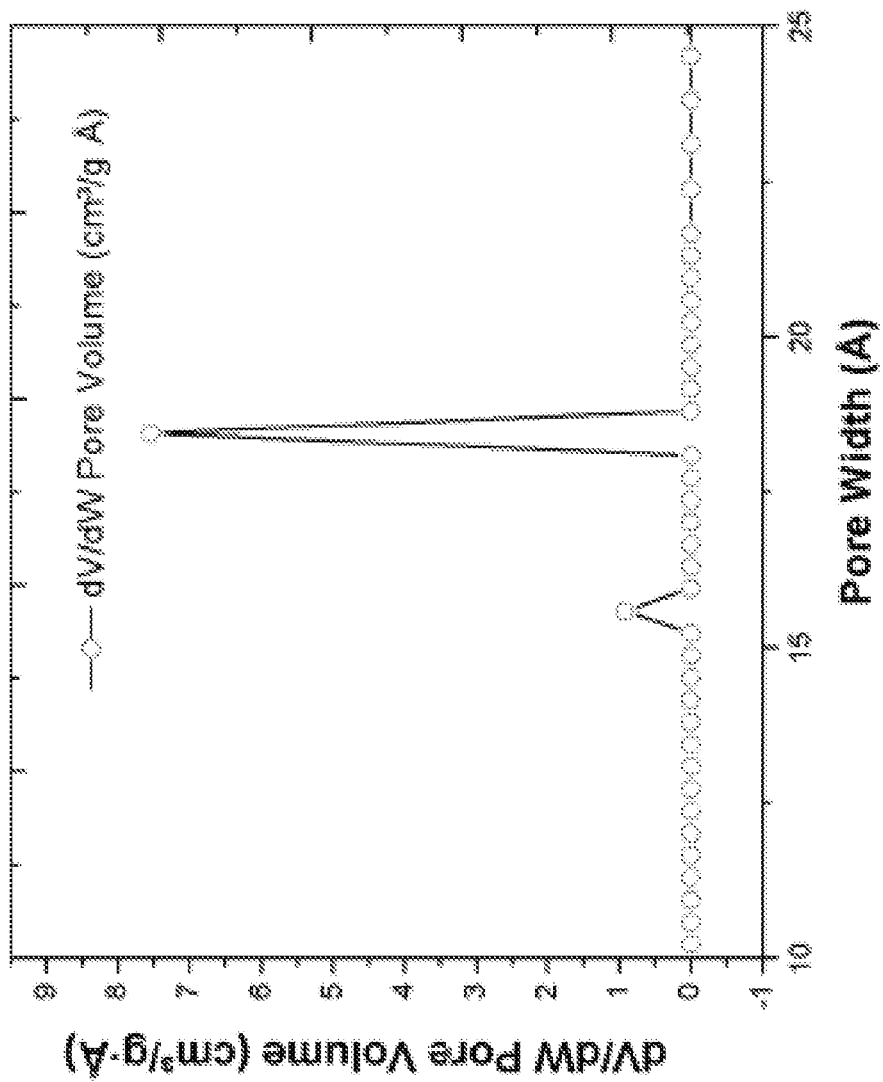
FIG. 13 is a graph showing pore size distributions of the metalated zirconium form (Zr-MTBC-CoCl) of the metal organic framework described for FIG. 12A.

Absorption Isotherms:

Nitrogen sorption isotherms of Zr-MTBC-CoCl were collected at 77K. Zr-MTBC-ColCl have BET surface areas of 12.87 m2/g. FIG. 13 shows the pore size distributions of Zr-MTBC-CoCl.

Thermogravimetric Analysis:

The first weight loss (54.8%) in the 25-400° C. temperature range corresponds to removal of adsorbed solvents in the pores. The second weight loss (73.7%) in the 420-800° C. temperature range corresponds to decomposition of the MOF to $(ZrO_2)_{13}(C_2O_3)_8$, close to calculated weight loss of 67.8% based on $[Zr_6O_4(OCoCl)_4(L)_3]_6[Zr_8O_8(OCoCl)_4(L)_3]_2$ to $(ZrO_2)_{52}(Co_2O_3)_{16}$.

NMR Analysis:

The $^1$H NMR (500 MHz) spectrum of digested Zr-MTBC-CoCl was compared to that of the organic bridging ligand. 5% $D_3PO_4$, in DMSO-$d_6$ was used as the $^1$H NMR solvent. The $^1$H NMR spectrum of the digested lithiated Zr-MTBC-CoCl showed that the ligand of Zr-MTBC remained intact after treatment with $CoCl_2$ and n-BuLi during metalation.

Crystallographic Data for Zr-MTBC-CoCl:

The crystallographic data for Zr-MTBC-CoCl is shown in Table 13, below.

TABLE 13

Crystallographic Data for Zr-MTBC-CoCl.

| Name | Zr-MTBC-CoCl |
|---|---|
| Formula | $C_{318}O_{66}Zr_{13}$ |
| Fw | 6061.04 |
| Temperature (K) | 100 |
| Wavelength (Å) | 0.41328 |
| Crystal system | Cubic |
| Space group | Pm$\bar{3}$n |
| a, Å | 41.616(4) |
| b, Å | 41.616(4) |
| c, Å | 41.616(4) |
| α, ° | 90 |
| β, ° | 90 |

TABLE 13-continued

Crystallographic Data for Zr-MTBC-CoCl.

| Name | Zr-MTBC-CoCl |
|---|---|
| γ, ° | 90 |
| V, Å$^3$ | 72074.21 |
| Z | 4 |
| Density (calcd. g/cm$^3$) | 0.559 |
| Absorption coeff. (mm$^{-1}$) | 0.284 |
| F(000) | 11824.0 |
| θ range data collection | 1.097-26.396 |
| Limiting indices | −46 <= h <= 33; −46 <= k <= 46; −46 <= l <= 37 |
| Reflections collected | 9409 |
| Independent reflections | 8895 |
| R(int) | 0.3798 |
| Data/restraints/parameters | 9409/331/298 |
| Goodness-of-fit on F$^2$ | 1.159 |
| Final R indices [I > 2σ(I)] | R1 = 0.1310, wR2 = 0.3599 |
| R indices (all data) | R1 = 0.1392, wR2 = 0.3539 |

X-Ray Adsorption Spectroscopy Analysis:

X-ray absorption data were collected at Beamline 10-BM at the Advanced Photon Source (APS) at Argonne National Laboratory. Spectra were collected at the cobalt K-edge in transmission mode. The X-ray beam was monochromatized by a Si(111) monochromater and detuned by 25% to minimize harmonics. A metallic cobalt foil standard was used as the reference for energy calibration and was measured simultaneously with experimental samples. The incident beam intensity ($I_0$) was measured by an ionization chamber with 30% $N_2$ and 70% He gas composition. Data was collected in three regions: a pre-edge region −150 to −20 eV (5 eV step size, dwell time 1.0 s), XANES region—20 to 50 eV (0.5 eV step size, dwell time 1.0 s), and EXAFS region 3.62 Å$^{-1}$ to 13.93 Å$^{-1}$ (0.05 Å$^{-1}$ step size, dwell time increased linearly from 1.0 to 3.9 seconds over the region to facilitate higher k-weighted data processing). All energies are listed relative to the elemental Co K-edge (7709 eV). Multiple X-ray absorption spectra were collected at room temperature for each sample. Samples were ground, mixed with polyethyleneglycol (PEG), and packed in a 6-shooter sample holder to achieve adequate absorption length.

Data were processed using the Athena and Artemis programs of the IFEFFIT package based on FEFF 6. See Rehr et al., Reviews of Modern Physics, 2000, 72, 621-654; and Ravel et al., Journal of Synchrotron Radiation, 2005, 12, 537-541. Prior to merging, spectra were calibrated against the reference spectra (metallic Co or Fe) and aligned to the first peak in the smoothed first derivative of the absorption spectrum, background removed, and spectra processed to obtain a normalized unit edge step.

Figure 17:
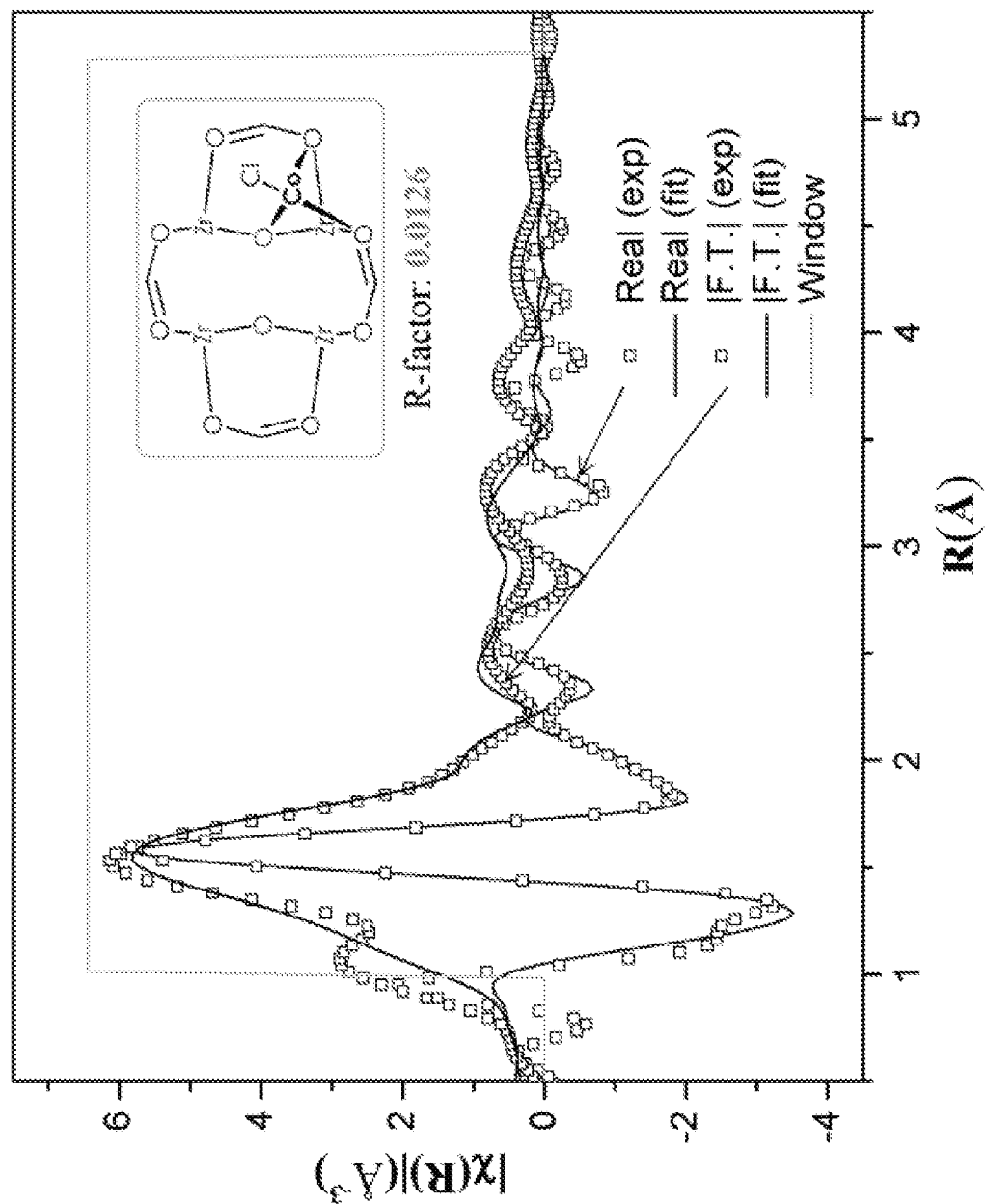
FIG. 17 is a graph of the fitting on extended x-ray absorption fine structure (EXAFS) data of the post-synthetically metalated metal organic framework (Zr-MTBC-CoCl) prepared in FIG. 14 using a proposed tetrahedral cobalt (Co) coordination model for a $Zr_8$ secondary building unit (SBU). The data can be fitted well with an R-factor of 0.0126.

Fitting on EXAFS data of Zr-MTBC-CoCl using only a $Zr_6O_4(OCoCl)_4$ model give a poor R-factor of 0.0499. A proposed tetrahedral Co coordination model to $Zr_8$ SBU is shown in FIG. 17. The EXAFS data of Zr-MTBC-CoCl can be fitted well using this model with an R-factor of 0.0126. EXAFS data of Zr-MTBC-CoCl cannot be fitted well using an alternative triangular Co coordination model to both μ$_2$-O on $Zr_8$ SBU, with an R-factor of 0.0164. EXAFS data of Zr-MTBC-CoCl cannot be fitted well using an alternative triangular Co coordination model to both μ$_2$-O on $Zr_8$ SBU, with an R-factor of 0.0219. Table 14 provides a summary of the EXAFS fitting parameters for Zr-MTBC-CoCl.

TABLE 14

EXAFS fitting parameters for Zr-MTBC-CoCl

| $Zr_8O_8(OCoCl)_4$ SBU (25%) | | $Zr_6O_4(OCoCl)_4$ SBU (75%) | |
|---|---|---|---|
| Fitting range | | k 1.50-11.60 Å$^{-1}$ | |
| Independent points | | 27 | |
| Variables | | 15 | |
| Reduced chi-square | | 84.9 | |
| R-factor | | 0.0126 | |
| $\Delta E_0$(eV) | | $-1.15 \pm 2.11$ | |
| $S_0^2$ | 0.25 | $S_0^2$ | 0.75 |
| R (Co-$\mu_3$-O) | $1.87 \pm 0.03$ | R (Co-$\mu_4$-O) | $1.97 \pm 0.27$ Å |
| R (Co—O$^{CO2-}$) | $2.01 \pm 0.00$ | R (Co—O$^{CO2-}$) | $1.98 \pm 0.14$ Å |
| R (Co—C$^{CO2-}$) | $2.12 \pm 0.03$ | R (Co—C$^{CO2-}$) | $2.17 \pm 0.08$ Å |
| R (Co—Cl) (1) | $2.35 \pm 0.00$ | R (Co—Cl) (1) | $2.19 \pm 0.05$ Å |
| R (Co—Zr) (1) | $2.46 \pm 0.04$ | R (Co—O$^{CO2-}$) | $2.62 \pm 0.04$ Å |
| R (Co—O$^{CO2-}$) | $2.67 \pm 0.00$ | R (Co—Zr1) (1) | $2.90 \pm 0.06$ Å |
| R (Co-C$^{CO2-}$) | $2.88 \pm 0.00$ | R (Co—C$^{Ph}$) (2) | $3.36 \pm 0.04$ Å |
| R (Co-$\mu_2$-O$^{distal}$) (1) | $3.69 \pm 0.10$ | R (Co—O$^{CO2-distal}$) (2) | $3.42 \pm 0.05$ Å |
| R (Co—Zr2) (1) | $3.00 \pm 0.04$ | R (Co—C$^{CO2-distal}$) (2) | $3.45 \pm 0.05$ Å |
| R (Co—Zr3) | $4.26 \pm 0.04$ | R (Co—Zr2) (2) | $3.77 \pm 0.06$ Å |

Degeneracy (coordination number) in parenthesis.

Figure 14:
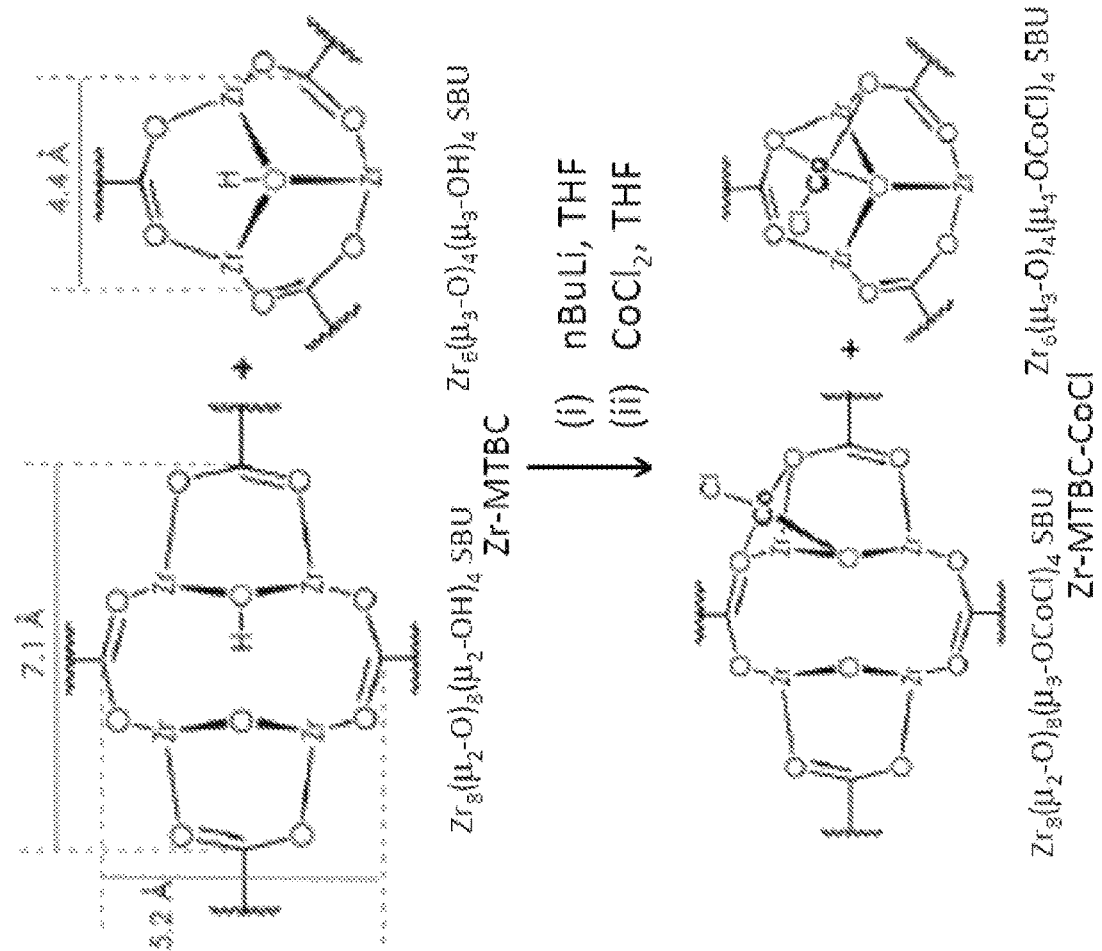
FIG. 14 is schematic drawing of the metalation of zirconium (Zr) secondary building units (SBUs) (both $Zr_8$-SBUs and $Zr_6$ SBUs) of the Zr form (Zr-MTBC) of the metal organic framework (MOF) described in FIG. 12A with cobalt chloride ($CoCl_2$) to from the metalated MOF, Zr-MTBC-CoCl.
Figure 15:
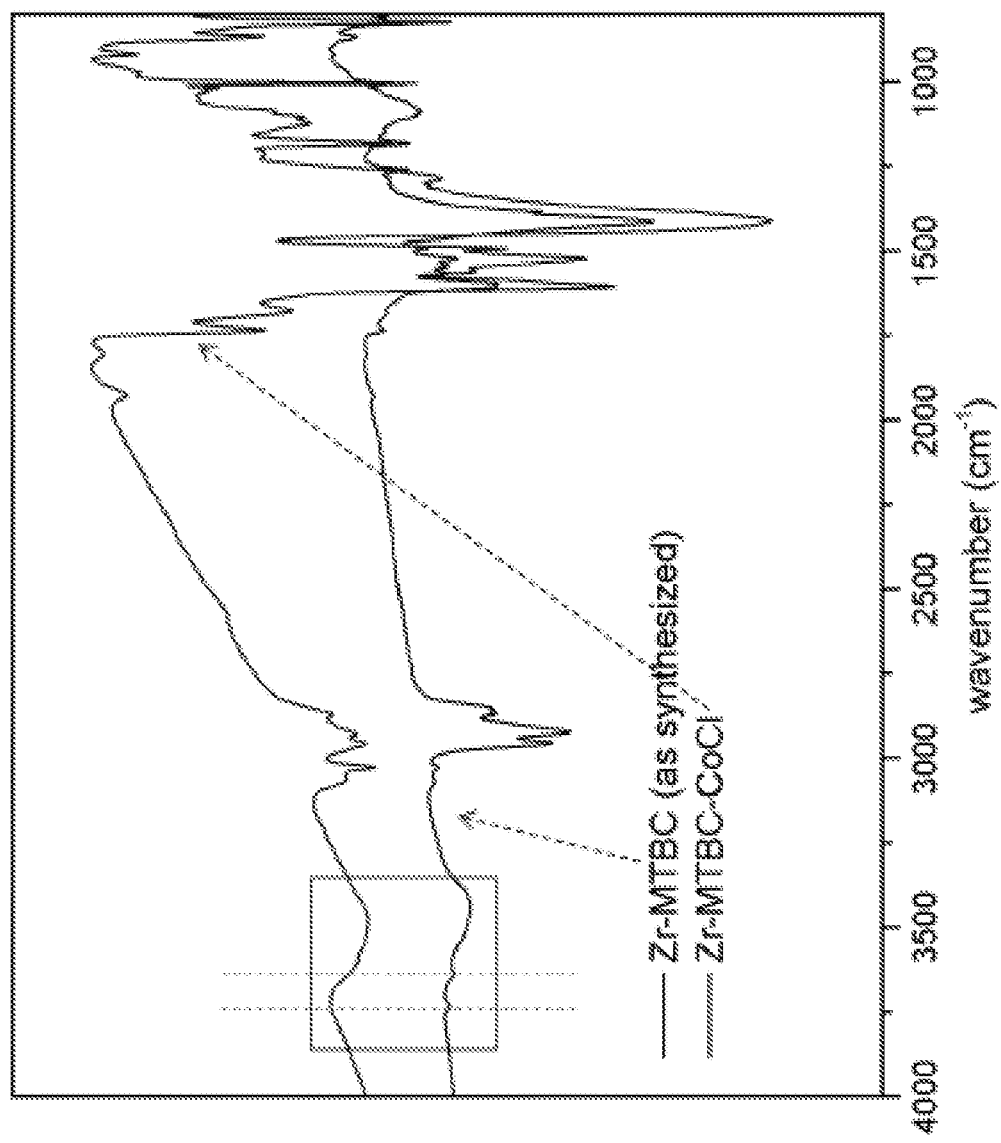
FIG. 15 is a graph showing the infrared (IR) spectra of the freshly prepared metalated metal organic framework (Zr-MTBC-CoCl) shown in FIG. 13 and the corresponding metal organic framework (Zr-MTBC (as synthesized)) prior to post-synthetic metalation. The zirconium $(Zr)_6$ cluster $\mu_3$-OH stretching at 3639 wavenumbers ($cm^{-1}$) and the $Zr_8$ cluster $\mu_2$-OH stretching at 3737 $cm^{-1}$ disappeared after metalation, indicating metalation at both sites.
Figure 16B:
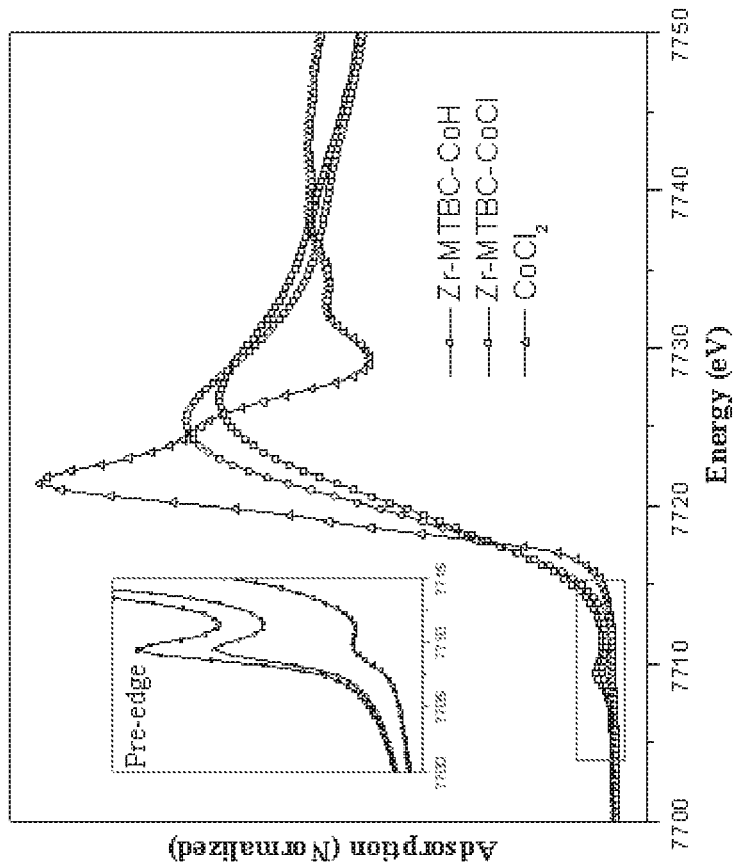
FIG. 16B is a graph of the x-ray absorption near edge structure (XANES) spectra of the post-synthetically metalated metal organic framework (Zr-MTBC-CoCl) described for FIG. 14, the corresponding catalyst (Zr-MTBC-Co), and cobalt chloride ($CoCl_2$). All three spectra are similar, indicating a +2 oxidation state for the cobalt centers in the Zr-MTBC-CoCl and Zr-MTBC-Co.
Figure 16A:
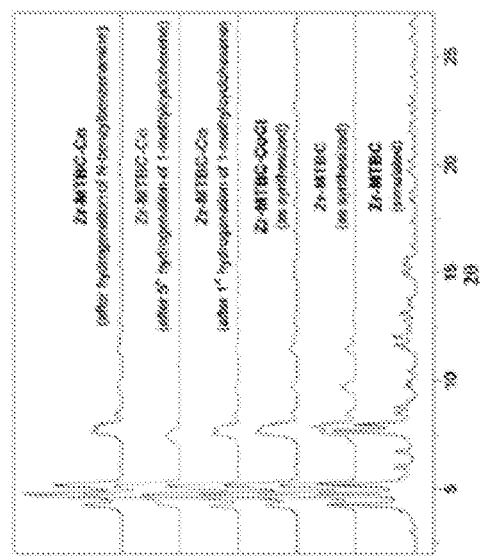
FIG. 16A is a graph showing the powder x-ray diffraction (PXRD) patterns simulated for the zirconium form (Zr-MTBC) metal organic framework (MOF) described for FIG. 12A prior to post-synthetic metallation (Zr-MTBC (simulated)), experimentally determined for same MOF (Zr-MTBC (as synthesized)), experimentally determined for the MOF after the post-synthetic metalation shown in FIG. 14 (Zr-MTBC-CoCl (as synthesized)), experimentally determined for the corresponding MOF catalyst after recovery from one use as a catalyst for the hydrogenation of 1-methylcyclohexene (Zr-MTBC-Co (after $1^{st}$ hydrogenation of 1-methylcyclohexene)), experimentally determined for the corresponding MOF catalyst after recovery from the fifth use as a catalyst for the hydrogenation of 1-methylcyclohexene (Zr-MTBC-Co (after 5th hydrogenation of 1-methylcyclohexene)), and experimentally determined for the corresponding MOF catalyst after recovery from use as a catalyst for the hydrogenation of N-benzylbenzenamine (Zr-MTBC-Co (after hydrogenation of N-benzylbenzenamine)). The PXRD patterns for the recovered MOF catalysts indicate the retention of crystallinity after post-synthetic metalation and catalysis.

Summary:

Zr-MTBC was treated with 10 equiv. of n-BuLi to deprotonate both the $\mu_2$-OH's in $Zr_8$—SBU and the $\mu_3$-OH's in $Zr_6$—SBU, then reacted with a CoCl$_2$ solution in THF to afford Zr-MTBC-CoCl as a deep-blue solid. See FIG. 14. Both the carboxylate groups and the linkers remained intact during lithiation and metalation as evidenced by a $^1$H NMR spectrum of the digested Zr-MTBC-CoCl in D$_3$PO$_4$/DMSO-d$_6$ and by the retention of strong carboxylate carbonyl stretching in the IR spectrum. See FIG. 12B. The disappearance of both the v $\mu_{2O-H}$ band (3737 cm$^{-1}$) and v $\mu_{3O-H}$ band (3639 cm$^{-1}$) in the IR spectrum indicated that the metalation occurred at both SBU sites. See FIG. 15. Inductively coupled plasma-mass spectrometry (ICP-MS) analysis of the digested MOF revealed complete metalation of all $Zr_8$ and $Zr_6$ clusters, corresponding to four Co centers per $Zr_8$ or $Zr_6$ node. Crystallinity of the MOF was maintained after metalation, as indicated by the similarity between the powder X-ray diffraction (PXRD) patterns of Zr-MTBC and Zr-MTBC-CoCl. See FIG. 16A. However, the coordination environments of the Co centers in Zr-MTBC-CoCl could not be established by X-ray diffraction due to intrinsic disorder of coordinated cobalt atoms. Instead, X-ray adsorption spectroscopy (XAS) was used to investigate Co coordination environments. Four out of six faces of the $Zr_8(\mu_2-O)_8(\mu_2-OH)_4$ cubic node had a $\mu_2$-OH group that could be lithiated and used for Co binding. See FIG. 14. Two different Co coordination modes on the $Zr_8$ node are suggested: $\mu_2$-oxide/$\mu_2$-oxo chelation and $\mu_2$-oxide/($\mu$-carboxylate)$_2$ tridentate binding. It is believed that the $\mu_2$-oxide/$\mu_2$-oxo chelation binding mode would not be ideal because the $\mu_2$-oxide to $\mu_2$-oxo distance was only 2.35 Å, too short for chelation to the same Co center. Such a structural model does not fit the extended X-ray adsorption fine structure (EXAFS) data. In contrast, the $\mu_2$-oxide and two $\mu$-carboxylate groups could coordinate to the same Co center in a stable conformation, with Co to $\mu_2$-oxide distance of 1.88 Å and Co to $\mu$-carboxylate distance of 2.00 Å, as indicated by the EXAFS fitting result. Cobalt coordination on $Zr_6$ node also adopts a $\mu_2$-oxide/($\mu$-carboxylate)$_2$ tridentate mode, identical to that observed in the previously studied UiO-68-CoCl system.

Example 13

Synthesis and Characterization of Zr-MTBC-CoH

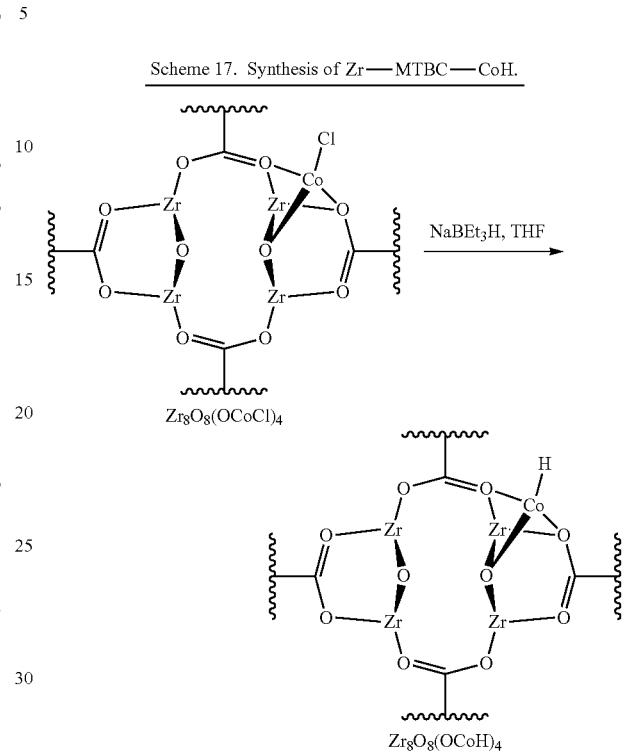

Scheme 17. Synthesis of Zr—MTBC—CoH.

As shown in Scheme 17, in a glovebox, Zr-MTBC-CoCl (2 mg) in 1 mL THF was treated with NaBEt$_3$H (20 µL, 1 M in THF) dropwise, and the resultant black suspension was allowed to sit for one hour. The black solid was centrifuged out and washed with THF three times. Then, the Zr-MTBC-CoH was directly used for catalytic reactions.

Hydrogenation Quantification:

In a J. Young tube, Zr-MTBC-CoH (10 µmol of Co) in 1 mL benzene was treated with formic acid (1.8 µL, 100 µmol) and immediately sealed. After reacting at room temperature for 1 h, the head space was analyzed via GC to quantify the amount of H$_2$. Consistent results were obtained in three runs. The amount of H$_2$ was calculated to be 9.2±1.1 µmol (expected 10 µmol).

In a J. Young tube, Zr-MTBC-CoH (10 µmol of Co) in 1 mL benzene was treated with water (1.8 µL, 100 µmol) and immediately sealed before water could contact the MOF suspension. After heating at 75° C. for 1 h, the head space was analyzed via GC to quantify the amount of H$_2$. Consistent results were obtained in three runs. Amount of H$_2$ was calculated to be 10.97±1.42 µmol (expected 10 µmol).

Adsorption Spectroscopy Analysis:

Table 15 provides a summary of the EXAFS fitting parameters for Zr-MTBC-CoH.

TABLE 15

EXAFS fitting parameters for Zr-MTBC-CoH

| $Zr_8O_8(OCoH)_4$ SBU (25%) | $Zr_6O_4(OCoH)_4$ SBU (75%) |
|---|---|
| Fitting range | k 1.70-12.30 Å$^{-1}$ |
| Independent points | 32 |

TABLE 15-continued

EXAFS fitting parameters for Zr-MTBC-CoH

| Variables | 20 |
|---|---|
| Reduced chi-square | 888.7 |
| R-factor | 0.0059 |
| $\Delta E_0(eV)$ | 2.57 ± 1.76 |

| | $S_0^2$ | 0.25 | | $S_0^2$ | 0.75 |
|---|---|---|---|---|---|
| R (Co-$\mu_3$-O) (1) | | 1.83 ± 0.03 | R (Co-$\mu_4$-O) (1) | | 1.95 ± 0.52 Å |
| R (Co—O$^{CO2-}$) (2) | | 1.94 ± 0.01 | R (Co—O$^{CO2-}$) (2) | | 1.96 ± 0.29 Å |
| R (Co—C$^{CO2-}$) (1) | | 2.07 ± 0.04 | R (Co—C$^{CO2-}$) (2) | | 2.09 ± 0.08 Å |
| R (Co—H) (1) | | 1.56 ± 0.10 | R (Co—H) (1) | | 1.43 ± 0.11 Å |
| R (Co—Zr) (1) | | 2.71 ± 0.07 | R (Co—O$^{CO2-}$) (2) | | 2.99 ± 0.06 Å |
| R (Co—O$^{CO2-}$) (1) | | 2.65 ± 0.11 | R (Co—Zr1) (1) | | 3.08 ± 0.15 Å |
| R (Co—C$^{CO2-}$) (1) | | 2.84 ± 0.00 | R (Co—C$^{Ph}$) (2) | | 3.52 ± 0.12 Å |
| R (Co-$\mu_2$-O$^{distal}$) (1) | | 3.32 ± 0.20 | R (Co—O$^{CO2-distal}$) (2) | | 3.32 ± 0.06 Å |
| R (Co—Zr2) (1) | | 3.08 ± 0.08 | R (Co—C$^{CO2-distal}$) (2) | | 3.35 ± 0.06 Å |
| R (Co—O$^{CO2-distal}$) | | 3.36 ± 0.00 | R (Co—Zr2) (2) | | 3.63 ± 0.08 Å |

Degeneracy (coordination number) in parentheses.

To investigate the possibility of Co nanoparticle formation during the Zr-MTBC-CoH catalyzed hydrogenation reactions, we obtained an XANES spectrum of a Zr-MTBC-CoH sample recovered after hydrogenation of 1-metylcyclohexene. The inclusion of 5 mol % of Co nanoparticles in EXAFS fittings led to an unsatisfactory fit. Due to the high degeneracy of the closest heavy metal atoms within the metal clusters, the presence of only 5% metal clusters would still have a large contribution to the EXAFS spectrum. For Co nanoparticles, one Co atom has 12 Co atoms (1st shell) with 2.50 Å distance and 6 atoms (2nd shell) with 3.54 Å distance, which are responsible for the misfit at 2.1 Å and 3.1 Å in EXAFS spectrum of Zr-MTBC-CoH after hydrogenation.

Figure 16C:
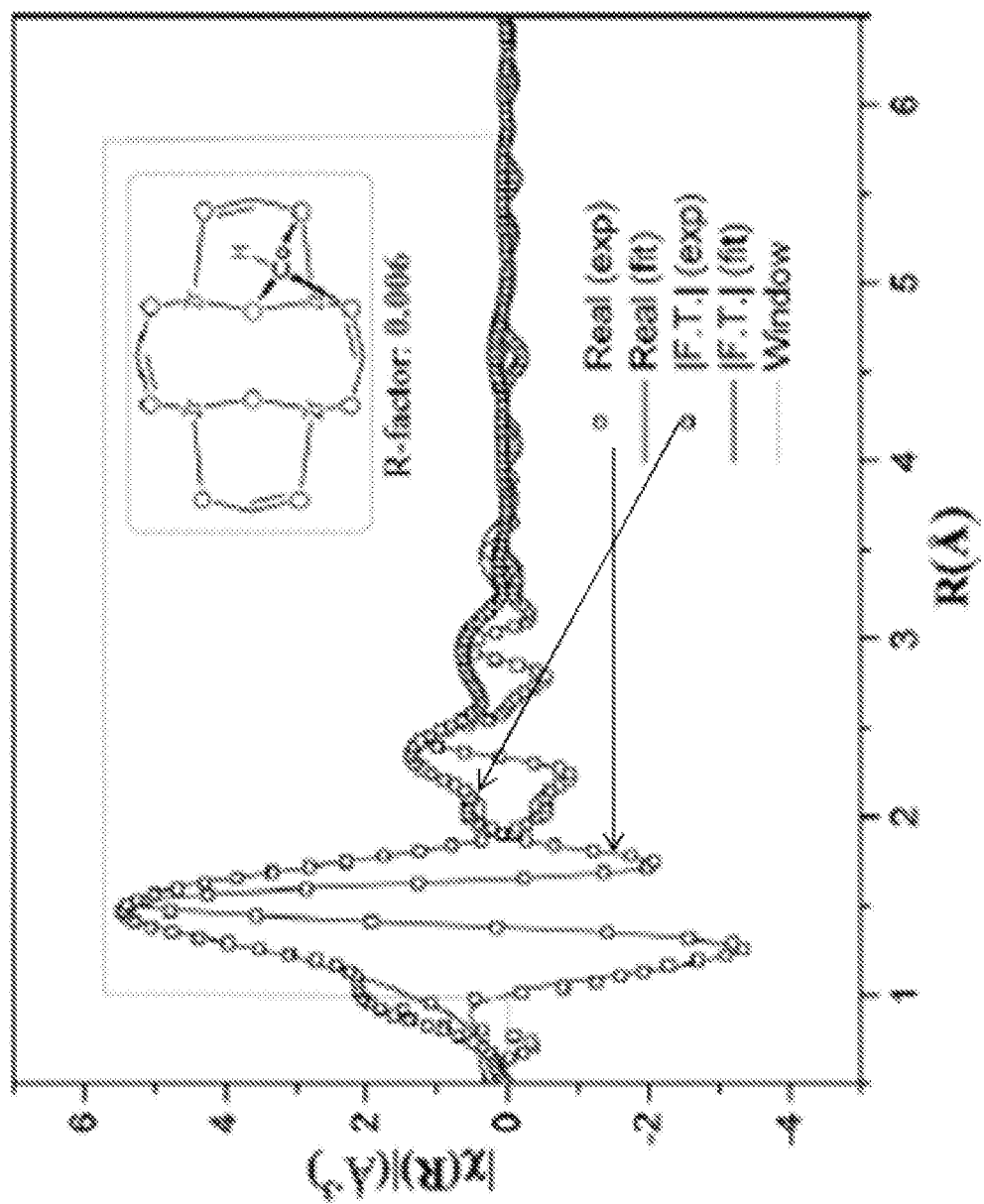
FIG. 16C is a graph of the extended x-ray absorption fine structure (EXAFS) spectra and fits in R-space at the cobalt (Co) K-edge of the hydride (Zr-MTBC-CoH) prepared from the metalated metal organic framework (Zr-MTBC-CoC) shown in FIG. 14, showing the magnitude (hollow squares) and real component (hollow squares) of the Fourier transformation. The fitting range is 1.2-5.8 Angstroms (Å) in R space (within the grey dotted lines).

Summary:

Activation of Zr-MTBC-CoCl with 5 equiv. of NaBEt$_3$H in THF generated the cobalt-hydride species Zr-MTBC-CoH as a black solid for use as an olefin hydrogenation catalyst. No formation of hydrogen gas was observed by GC analysis, indicating H/Cl metathesis during the activation step. The reaction of Zr-MTBC-CoH with 10 equiv. of formic acid at room temperature or with excess water at 75° C. readily generated an equivalent amount of H$_2$, supporting the identity of Zr-MTBC-CoH. XANES analysis of Zr-MTBC-CoH suggested a +2 oxidation state of Co. See FIG. 16B. EXAFS fitting on Zr-MTBC-CoH indicated that the Co adopts $\mu_2$-oxide/$\mu$-carboxylate)$_2$ tridentate binding mode, with Co to $\mu_2$-oxide distance of 1.83 Å and Co to $\mu$-carboxylate distance of 1.94, similar to the structure proposed for Zr-MTBC-CoCl. See FIG. 16C.

Example 14

Catalytic Hydrogenation of Alkenes with Zr-MTBC-CoH

General Procedure for Zr-MTBC-CoH Catalyzed Hydrogenation of Olefins:

In a nitrogen-filled glove box, Zr-MTBC-CoCl (0.25 mg, 0.25 μmol Co) in 1.0 mL THF was charged into a glass vial. NaBEt$_3$H (10 μL, 1.0 M in THF) was then added to the vial and the mixture was stirred for 1 h. The solid was then centrifuged, washed with THF twice, and transferred to a glass vial in 1.0 mL THF. The olefin substrate was added to the vial, which was placed in a Parr reactor, sealed under nitrogen, and charged with hydrogen to 40 bar. After stirring at room temperature for 1-3 d, the pressure was released and the MOF catalyst was removed from the reaction mixture via centrifugation. Mesitylene (internal standard) was added to the organic extracts and the yield of the product was determined by integrations of the product and mesitylene peaks in the $^1$H NMR spectra in CDCl$_3$.

A Typical Procedure for Zr-MTBC-CoH Catalyzed Hydrogenation of Olefins:

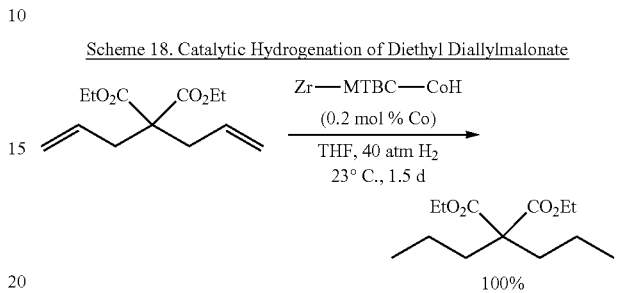

Scheme 18. Catalytic Hydrogenation of Diethyl Diallylmalonate

The catalytic hydrogenation of diethyl diallylmalonate is shown in Scheme 18, above. In a glovebox, Zr-MTBC-CoCl in THF (0.25 mg, 0.2 mol % Co) was charged into a small vial and 0.5 mL THF was added. Then, 10 μL NaBEt$_3$H (1.0 M in THF) was added to the vial and the mixture was stirred slowly for 1 h in the glovebox. The solid was centrifuged out of suspension and then washed with THF two times. Then, the black solid in 0.5 mL THF was transferred to a vial containing 0.5 mL THF solution of diethyl diallylmalonate (30.0 mg, 0.125 mmol). The vial was placed into a Parr pressure reactor in a nitrogen-filled glovebox, then pressurized to 40 bar. After stirring at room temperature for 1.5 d, the solid was centrifuged out of suspension and extracted three times with THF. The combined organic extracts were concentrated in vacuo to afford crude diethyldipropylmalonate in quantitatively yield, which was sufficiently pure as determined via $^1$H NMR.

The above reaction was repeated in presence of metallic mercury under the identical reaction conditions. The catalytic activity of Zr-MTBC-CoH was not affected by the presence of mercury, which suggests that Co-nanoparticles were not the catalytic species in alkene hydrogenation.

Test of "Heterogeneity" of the MOF Catalysis in Alkene Hydrogenation:

The hydrogenation of styrene did not occur in the presence of supernatant obtained after the hydrogenation of 1-methylcyclohexene; however, it proceeded in the presence of recovered Zr-MTBC-Co, demonstrating the "heterogeneous" nature of MOF catalysis. More particularly, in a nitrogen-filled glove box, Zr-MTBC-CoCl (0.25 mg, 0.1 mol % Co) in 1.0 mL THF was charged into a glass vial. NaBEt$_3$H (10 μL, 1.0 M in THF) was then added to the vial and the mixture was stirred for 1 hour. The solid was then centrifuged, washed with THF twice, and transferred to a glass vial containing 1.0 mL THF. 1-Methylcyclohexene (29 μL, 0.25 mmol) was then added to the vial. The vial was then placed in a Parr reactor, which was sealed under nitrogen atmosphere and later charged with hydrogen to 40 bar. After 24 h, the pressure was released and the MOF catalyst was centrifuged out from suspension. 1-Methylcyclohexene was completely converted to methylcyclohexane as determined by $^1$H NMR spectra based on the integration of substrate and product peaks in the crude.

After the solid and supernatant were separated, styrene (1.07 mL, 6.82 mmol) was added to each of the portions which were later placed in a Parr reactor, sealed under nitrogen, and charged with hydrogen to 40 bar. After 24 h, the pressure was released and the supernatant was separated from the solid catalyst. Conversion styrene to ethylbenzene was 100% in the presence of Zr-MTBC-Co and 0% in the presence of the supernatant, determined based on integration of substrate and product peaks in the crude $^1$H NMR spectra. This study indicates that Zr-MTBC-Co is the actual catalyst for alkene hydrogenation.

Investigation of Catalytic Activity of Co-Nanoparticles in Alkene Hydrogenation:

In a nitrogen-filled glove box, CoCl$_2$ (1.0 mg, 2.5 mol % Co) in 2.0 mL THF was charged into a glass vial. NaBEt$_3$H (25 µL, 1.0 M in toluene) was then added to the vial and the mixture was stirred for 30 min. 2,3-dimethyl-2-butene (36 µL, 0.303 mmol) was then added to the vial. The vial was then placed in a Parr reactor, which was sealed under nitrogen atmosphere and then charged with hydrogen to 40 bar. After 24 h, the pressure was released and the MOF catalyst was centrifuged out from suspension. $^1$H NMR spectra showed no conversion of 2,3-dimethyl-2-butene to 2,3-dimethylbutane.

Reuse and Recycle Experiment Procedure for Zr-MTBC-CoH-Catalyzed Hydrogenation of 1-Methylcyclohexene:

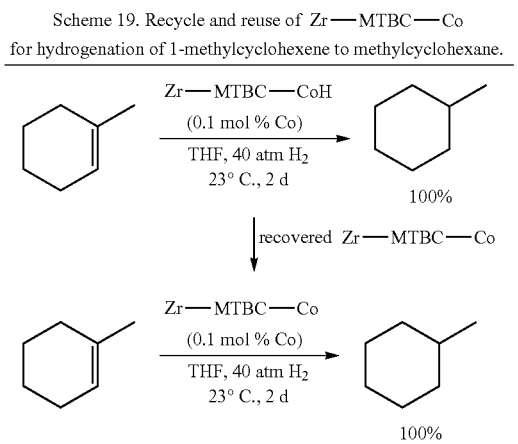

Scheme 19. Recycle and reuse of Zr—MTBC—Co for hydrogenation of 1-methylcyclohexene to methylcyclohexane.

Scheme 19 shows the reuse of Zr-MTBC-Co in an olefin hydrogenation reaction. More particularly, in a glovebox, a vial was charged with Zr-MTBC-CoCl (0.5 mg, 0.1 mol % Co) in 1 mL THF. 14 µL NaBEt$_3$H (1.0 M in THF) was added to the vial and the mixture was stirred slowly for 1 h in the glovebox. The solid was centrifuged out of suspension and washed with THF two times. Then, the solid in 1.0 mL THF was transferred to a vial and 1-cyclohexene (59 µL, 0.50 mmol) was added. The vial was placed into a Parr pressure reactor in a nitrogen-filled glovebox. The reactor was then pressurized to 40 bar. After 2 d, hydrogen was released and the solid was centrifuged out of suspension and extracted two times with THF in the glovebox. Quantitative yield of methylcyclohexane was obtained as determined by $^1$H NMR with mesitylene as the internal standard.

The recovered solid catalyst was added to a vial containing 1-methylcyclohexene (59 µL, 0.50 mmol) in 1.0 mL THF. The vial was placed into a Parr pressure reactor in a nitrogen-filled glovebox. The reactor was then pressurized to 40 bar. After 2 d, the solid was centrifuged out of suspension and extracted two times with THF in the glovebox. Methylcyclohexane was obtained in quantitative yield as determined by $^1$H NMR with mesitylene as the internal standard. Zr-MTBC-Co was recovered and reused 5 times.

Figure 19:
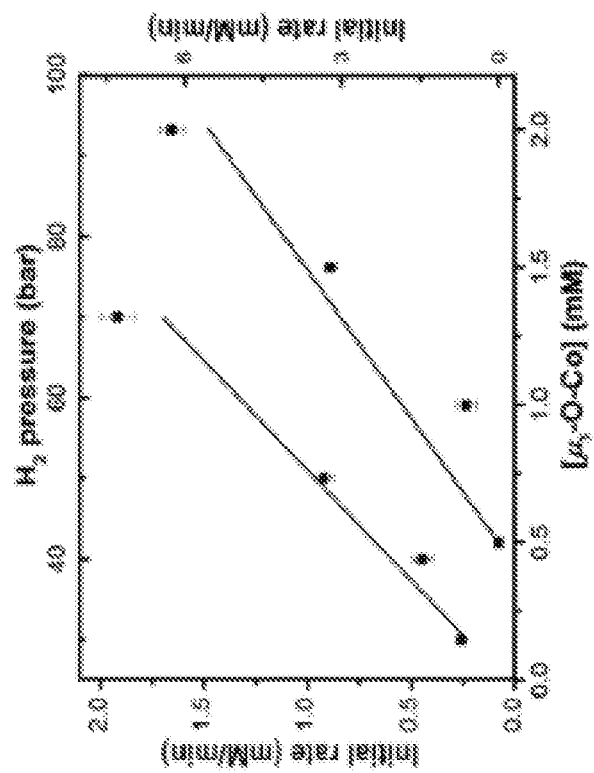
FIG. 19 is a graph showing the kinetic plots of initial rates (d[methylcyclohexane]/dt) for hydrogenation of 1-methylcyclohexene versus concentration of catalytic secondary building units ($Zr_2(\mu_3$-O)Co) and hydrogen pressure for the first 35 minutes, showing first order dependence on both components.
Figure 18:
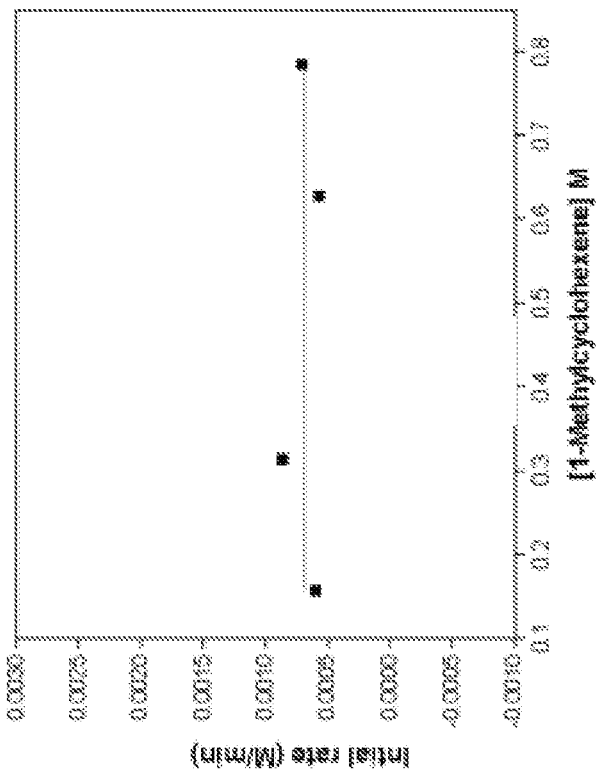
FIG. 18 is a graph of the initial reaction rate (d[methylcyclohexane]/dt) versus initial concentration of 1-cyclohexene ([1-cyclohexene]$_{initial}$) for the first 35 minutes (<10% conversion) of a metal organic framework catalyst catalyzed hydrogenation reaction. The graph shows the independence of the initial rates on alkene concentration. The catalyst concentration was 1.0 millimolar (mM) and the hydrogen pressure was 30 bar.

Determination of the Rate Law for Zr-MTBC-CoH-Catalyzed Hydrogenation of 1-Methylcyclohexene in THF:

The rate law of the hydrogenation of 1-cyclohexene was determined by the method of initial rates (up to 10% conversion). The reactions were conducted in THF (total volume of solution was 0.5 mL) at 23° C. in a small vial within a Parr reactor (inside volume of Parr reactor: 320 mL). To determine the rate dependence on one reagent, the concentration or pressure (in case of H$_2$) of that reagent was varied, while the concentration or pressure of other reagents and the total volume of the solution (0.5 mL) were held constant. After hydrogenation for 35 min, the concentration of the product methylcyclohexane was determined by GC-MS using mesitylene as the internal standard. The rates refer to the rates of product (methylcyclohexane) in units of mM·min$^{-1}$. To determine the rate dependence on 1-methylcyclohexene, the concentration of 1-methylcyclohexene was varied between 0.157-0.784 M, while the concentration of Co was 1.0 mM and pressure of H$_2$ was 30 bar. See FIG. 18. To determine the rate dependence on the catalyst, the concentration of Co was varied between 0.5-2.0 mM, while the concentration of 1-methylcyclohexene was 0.314 M and pressure of H$_2$ was 30 bar. See FIG. 19. To determine the rate dependence on H$_2$, the pressure of H$_2$ was varied between 30-70 bar, while the concentration of 1-methylcyclohexene and Co 0.314 M and 1.0 mM, respectively. See FIG. 19.

Synthesis of Cobalt-Functionalized Mesoporous Silica and Comparion of its Activity with Zr-MTBC-Co Under Identical Reaction Conditions MSU—H type of mesoporous silica (80 mg, from Sigma-Aldrich, St Louis, Mo., United States of America) was weighed in a glove box, dispersed in dry THF, and then treated with nBuLi (400 µL, 2.5 mM). After reaction at room temperature for 6 h, the lithiated mesoporous silica was washed with THF five times to remove excess nBuLi. The washed silica was transferred into CoCl$_2$ solution in THF (6 mL, 20 mM) and stirred for 6 h for metalation. After washing with THF five times to remove excess CoCl$_2$, the silica was directly used for catalytic reactions. ICP-MS analysis of the Co-functionalized mesoporous silica gave the amount of Co content of 2.0 mmol per gm of metalated silica.

The comparison of catalytic activities of Zr-MTBC-CoH to cobalt-functionalized mesoporous silica in hydrogenation of 2,3-dimethyl-2-butene under identical reaction conditions is displayed in Table 16. The results showed that cobalt-functionalized mesoporous silica was an active catalyst in hydrogenation, however with a much lower activity than the Zr-MTBC-CoH catalyst.

TABLE 16

Hydrogenation of alkenes catalyzed by Zr-MTBC-CoH and cobalt-functionalized mesoporous silica under identical reaction conditions.*

| Substrate | Yield (Time) with 0.05 mol % Zr-MTBC-CoH | Yield (Time) with 0.05 mol % cobalt-functionalized mesoporous silica |
|---|---|---|
| (2,3-dimethyl-2-butene) | 100% (48 h) | 41% (48 H) |

*Reaction conditions: 40 atm of H$_2$ at 22° C.

Figure 20:
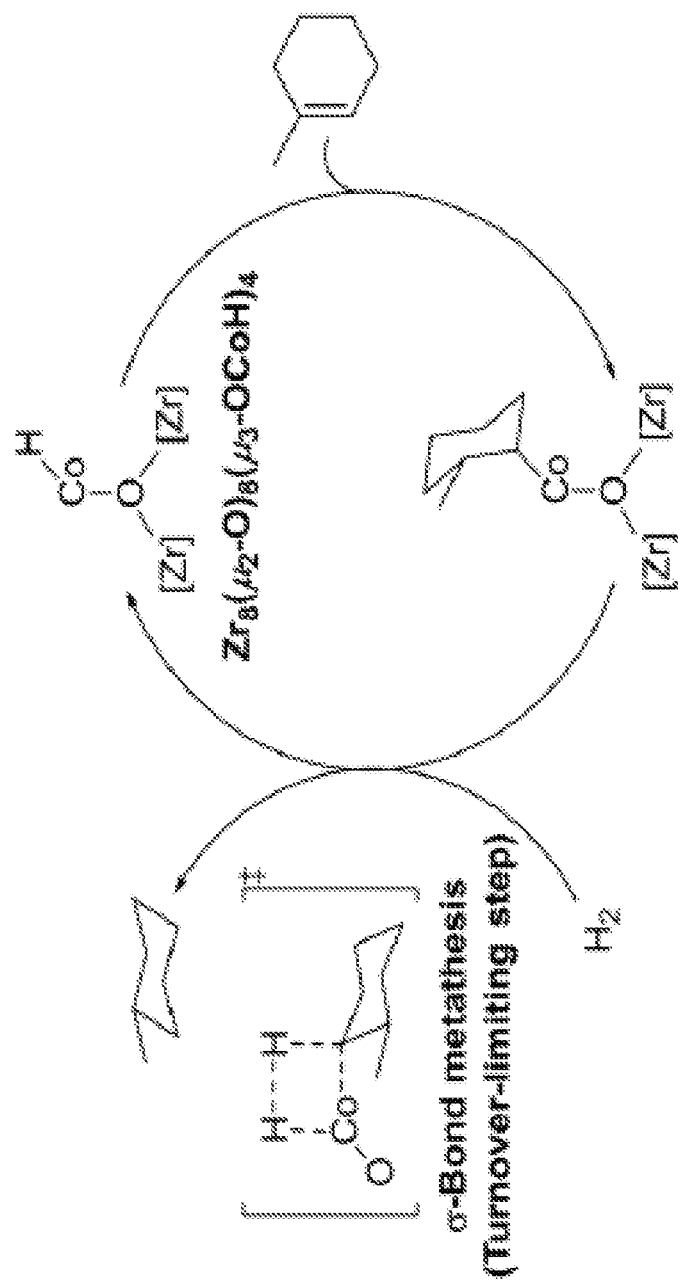
FIG. 20 is a schematic drawing showing a proposed catalytic cycle for alkene hydrogenation: the insertion of the alkene into the cobalt (Co)-hydrogen (H) bond gives a Co-alkyl species, followed by a turnover limiting sigma ($\sigma$)-bond metathesis with hydrogen gas ($H_2$) to generate the alkane product.

Mechanistic Investigation of Zr-MTBC-CoH Catalyzed Hydrogenation of 1-Methylcyclohexene:

As discussed above, the treatment of Zr-MTBC-CoCl with NaEt$_3$BH in THF generated Zr-MTBC-CoH species, which, without wishing to be bound by theory, is likely the active catalyst in the hydrogenation reactions. The EXAFS spectrum of Zr-MTBC-Co recovered from hydrogenation of 1-methylcyclohexene showed the absence of Co—Co scattering from Co nanoparticles, ruling out the formation of any Co-nanoparticles during the catalysis. To further study the mechanism, the rate law was determined by the method of initial rates (<15% conversion) in THF at room temperature. In order to avoid complications caused by the presence of two kinds of Co-centers in Zr-MTBC-CoH, the initial rates were measured for hydrogenation of 1-methylcyclohexene catalyzed by only Zr$_2$($\mu_3$-O)Co sites, since Zr$_3$($\mu_4$-O)CoH at the SBUs of UiO-68 was inactive in hydrogenation of 1-methylcyclohexene. The empirical rate law showed that the initial rates had a first-order dependence on the cobalt concentrations and P$_{H2}$ (see FIG. 19) and a zeroth-order dependence on the alkene concentration. See FIG. 18. The activation of H$_2$ at the electron deficient Co(II)-center via oxidative addition is believed to be unlikely. The kinetic and spectroscopic data thus suggest that the insertion of the C═C bond of the alkene into the Co—H bond generates a Co-alkyl intermediate, which undergoes σ-bond metathesis with H$_2$ in the turn-over limiting step to give an alkane product, simultaneously regenerating the cobalt-hydride species. See FIG. 20.

Summary: Zr-MTBC-CoH proved to be a highly active catalyst for hydrogenation of a range of alkenes in THF at room temperature. At a 0.05 mol % Co loading, terminal alkenes containing oxo-, carboxy-, pyridyl-, or silyl-functionalities (i.e., allyl ether, allyl acetate, dimethyl itaconate, 2-vinyl pyridine, and allyltrimethylsilane) were selectively hydrogenated to afford dipropylether, propylacetate, dimethyl 2-methylsuccinate, 2-ethylpyridine, and propyltrimethylsilane, respectively, in quantitative yields. See entries 1-6, Table 17, below. At a 0.05-0.1 mol % Co loading, Zr-MTBC-CoH was also very active in hydrogenation of trisubstituted alkenes such as ethyl-3,3-dimethylacrylate, α-terpinene, trans-α-methylstilbene, and 1-methyl-1-cyclohexene, and corresponding pure hydrogenated products were obtained in excellent yields by simple filtration of reaction mixtures followed by removal of the volatiles. See entries 8-12, Table 17. Impressively, Zr-MTBC-CoH completely hydrogenated tetrasubstituted alkenes such as 2,3-dimethyl-2-butene at room temperature within 48 h to afford 2,3-dimethylbutane with a TON>8000. See entry 13, Table 17. Hydrogenation of bulkier tetrasubstituted alkenes such as 2,3,4-trimethylpent-2-ene could also be achieved at elevated temperatures, which facilitated their diffusion through MOF channels, as well as the binding and activation of the substrate at the cobalt-site. See entry 14, Table 17. It has been previously observed that the Zr$_3$($\mu_4$-O)Co site in UiO-68 Zr$_6$ SBU is inactive in catalyzing the hydrogenation of bulky and rigid trisubstituted alkenes such as 1-methyl-1-cyclohexene and tetrasubstituted alkenes. See Manna et al., Nat. Commun., 2016, 7, 12610 (DOI: 10.1038/ncomms12610). Therefore, without being bound to any one theory, it is believed that the hydrogenation of these bulky alkenes occurred exclusively at the Zr$_2$($\mu_3$-O)Co sites in Zr$_8$-SBUs of Zr-MTBC-CoH. The hydrogenation of methylheptenone to methylheptenone catalyzed by Pd/C or Pd/Al$_2$O$_3$ is a key step to synthesizing dimethyloctenol (DMOE), an important fragrance compound. See WO 2012/025559. At a 0.5 mol % Co loading, Zr-MTBC-CoH also selectively hydrogenated methylheptenone to afford methylheptanone at 40° C. in quantitative yield. See entry 15, Table 17. Interestingly, 6-methyl-2-heptanol was obtained quantitatively upon heating the reaction mixture at 80° C. See entry 16, Table 17.

TABLE 17

Catalytic Hydrogenation of Olefins with Zr-MTBC-H.

| Entry | Substrate | Product | mol % Co | Time (d) | Yield[b] | TON |
|---|---|---|---|---|---|---|
| 1 | allyl ether | dipropyl ether | 0.05 | 1.5 | 100 (86) | >2000 |
| 2 | allyl OAc | propyl OAc | 0.05 | 1.5 | 100 | >2000 |
| 3 | dimethyl itaconate (MeO$_2$C, CO$_2$Me) | dimethyl 2-methylsuccinate (MeO$_2$C, CO$_2$Me) | 0.05 | 1.5 | 100 | >2000 |
| 4 | diethyl diallylmalonate (EtO$_2$C, CO$_2$Et) | hydrogenated (EtO$_2$C, CO$_2$Et) | 0.2 | 15 | 100 | >500 |
| 5 | 2-vinylpyridine | 2-ethylpyridine | 0.05 | 1.5 | 100 (99) | >2000 |
| 6 | allyl-SiMe$_3$ | propyl-SiMe$_3$ | 0.05 | 1.5 | 100 | >2000 |
| 7 | CO$_2$Me acrylate | CO$_2$Me saturated | 0.05 | 1.5 | 100 (99) | >2000 |

TABLE 17-continued

Catalytic Hydrogenation of Olefins with Zr-MTBC-H.

| Entry | Substrate | Product | mol % Co | Time (d) | Yield[b] | TON |
|---|---|---|---|---|---|---|
| 8 | (CH₃)₂C=CH-CO₂Me | (CH₃)₂CH-CH₂-CO₂Me | 0.1 | 2 | 81 | 810 |
| 9 | 4-isopropyl-1-methylcyclohexa-1,3-diene | 1-isopropyl-4-methylcyclohexane | 0.05 | 2 | 100 (91) | >2000 |
| 10[c] | 4-(prop-1-en-2-yl)-1-methylcyclohexene | 1-isopropyl-4-methylcyclohexane | 0.05 | 2 | 100 dr; 1.3:1 | >2000 |
| 11 | Ph₂C=C(CH₃) (stilbene-type) | Ph₂CH-CH(CH₃) | 0.05 | 1.5 | 100 (95) | >2000 |
| 12 | 1-methylcyclohexene | methylcyclohexane | 0.05 | 0.5 | 100 | >8000[d] |
| 13 | 2,3-dimethyl-2-butene | 2,3-dimethylbutane | 0.05 | 2 d | 100 | >8000[d] |
| 14[c] | iPr-C(CH₃)=C(CH₃)₂ | iPr-CH(CH₃)-CH(CH₃)₂ | 0.5 | 2 d | 46 | 368[d] |
| 15[e] | 6-methylheptan-2-one (as product shown) | — | 0.5 | 0.75 | 100 | >200 |
| 16[f] | 6-methylhept-5-en-2-one | 6-methylheptan-2-ol | 0.5 | 2 d | 100 | >200 |

[a]Reaction conditions: 0.25 mg of Zr-MTBC-CoCl, 5 equiv of NaBET₃H (1.0 M in THF) w.r.t. Co, alkene, THF, 40 bar H₂, 23° C.
[b]Yields were determined by ¹H NMR with mesitylene as the internal standard. Isolated yield in the parenthesis.
[c]Reaction was performed at 70° C. in toluene.
[d]TON was calculated based on only Zr₂(μ₃-O)Co sites.
[e]Reaction was performed at 40° C.
[f]Reaction was performed at 80° C. in toluene.

Figure 21:
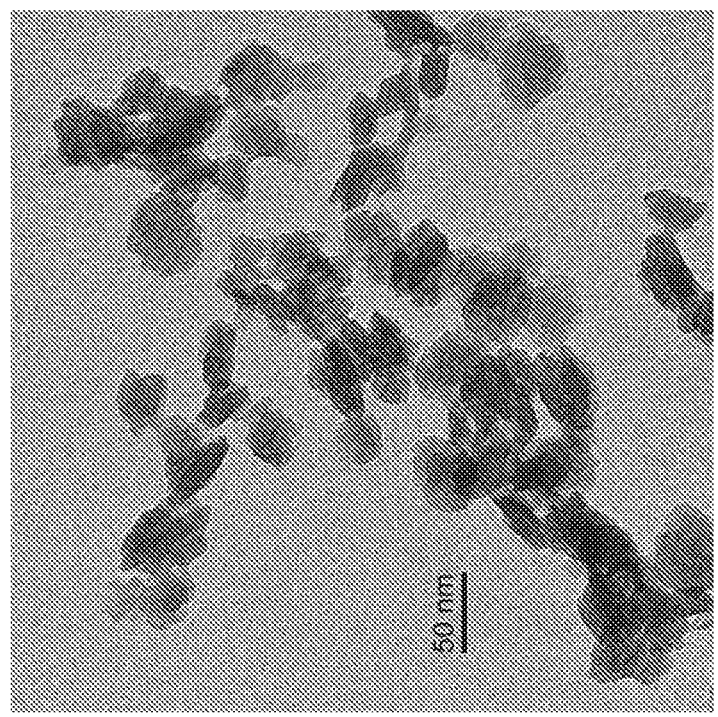
FIG. 21 is graph of the yields (%) of methylcyclohexane at different runs in the reuse study of the catalyst (Zr-MTBC-Co) corresponding to the metalated metal organic framework shown in FIG. 14 used in the hydrogenation of 1-methylcyclohexene. The cobalt (Co) loadings were about 0.1 mole %.

At a 0.1 mol % Co-loading, Zr-MTBC-CoH could be recovered and reused at least 5 times for the hydrogenation of 1-methylcyclohexene (see FIG. 21) without loss of MOF crystallinity. See FIG. 16A. Excellent yields (92-100%) of methylcyclohexane were obtained consistently in the reuse experiments with no observation of other byproducts. The PXRD patterns of Zr-MTBC-CoH recovered from the 1st and 6th runs remained unchanged from that of pristine Zr-MTBC-CoH. See FIG. 16A, indicating the stability of the MOF under reaction conditions. The heterogeneity of Zr-MTBC-CoH was confirmed by several experiments. ICP-MS analyses showed that the amounts of Co and Zr that leached into the supernatant after the first run were only 1.6% and 0.02%, respectively. Moreover, the rate of hydrogenation was unchanged in the presence of mercury and no additional hydrogenation was observed after removal of Zr-MTBC-CoH from the reaction mixture, which appears to rule out the role of the leached Co-nanoparticles or other Co-species in catalyzing hydrogenation reactions.

Example 15

Catalytic Hydrogenation of Imines and Carbonyls with Zr-MTBC-CoH

A Typical Procedure for Zr-MTBC-CoH Catalyzed Hydrogenation of Imines:

Scheme 20. Catalytic Hydrogenation of Imines with Zr—MTBC—Co

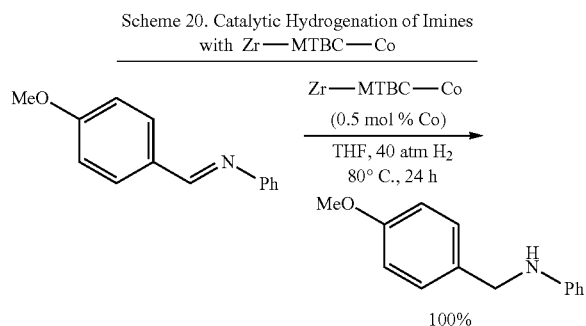

100%

The catalytic hydrogenation of an exemplary imine, N-(4-methoxybenzylidene)benzenamine) is shown in Scheme 20. More particularly, in a glovebox, Zr-MTBC-CoCl in THF (0.25 mg, 0.2 mol % Co) was charged into a small vial, and 0.5 mL THF was added. Then, 10 µL NaBEt₃H (1.0 M in THF) was added to the vial and the mixture was stirred slowly for 1 h in the glovebox. The solid was centrifuged out of suspension and then washed with THF two times. Then, the black solid in 0.5 mL THF was transferred to a vial containing 0.5 mL THF solution of N-(4-methoxybenzylidene)benzenamine (26.4 mg, 0.125 mmol). The vial was placed into a Parr pressure reactor in a nitrogen-filled glovebox, then pressurized to 40 bar. After stirring at 80° C. for 24 h, the solid was centrifuged out of suspension and extracted three times with THF. The combined organic extracts were concentrated in vacuo to afford crude N-(4-methoxybenzyl)aniline in quantitative yield, which was sufficiently pure as shown in $^1$H NMR spectrum.

Summary

Scheme 21. Catalytic Hydrogenation of Iminies and Carbonyls.

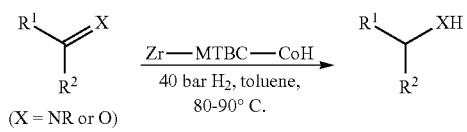

Prompted by the hydrogenation of the carbonyl group of methylheptenone at elevated temperatures, the hydrogenation of imines and carbonyls with Zr-MTBC-CoH was studied. See Scheme 21. Zr-MTBC-CoH displayed excellent activity in catalytic hydrogenation of imines. See Table 18, below. Though hydrogenation of imines is an important synthetic route to amines, examples of base metal catalysts for imine hydrogenation are rare. See Zhanq et al., Organometallics, 2015, 34, 2917-2923. The present imine hydrogenation reactions were performed in toluene at 80° C. under 40 bar of H₂ in presence of 0.5 mol % Zr-MTBC-CoH. N-benzylideneaniline was completely hydrogenated to N-benzylaniline in 5 h. The pure product was isolated in 98% yield after simple filtration followed by removal of the volatiles in vacuo. See entry 1, Table 18. The Zr-MTBC-CoH recovered after this reaction remained crystalline, as shown by PXRD. See FIG. 16B, and the leaching of Co and Zr into the supernatant was 0.23% and 0.08%, respectively. N-(4-chlorobenzylidene)benzenamine, N-(2-methoxybenzyli-dene)benzenamine, N-(4-methoxybenzylidene)benzenamine and N-benzylidenebenzylamine were efficiently reduced within 24 h to afford corresponding N-benzylanilines in excellent yields. See entries 2-5, Table 18. The hydrogenation of trisubstituted imines, such as (E)-N-(1-phenylethylidene)aniline, however, required longer reaction times (see entry 7, Table 18), presumably due to the decreased rates of diffusion of the larger substrate and product through the MOF channels and less facile binding and activation of the substrate.

Zr-MTBC-CoH is also active in catalyzing hydrogenation of carbonyls to their corresponding alcohols in toluene at 90° C. At a 0.5 mol % Co loading, Zr-MTBC-CoH afforded 1-phenylethanol, 1-(4-chlorophenyl)ethanol and cyclohexanol from the corresponding ketone substrates in good yields. See entries 8-10, Table 18. Benzaldehyde was also efficiently reduced to benzyl alcohol in 90% isolated yield.

TABLE 18

Zr-MTBC-CoH-catalyzed Hydrogenation of Imines and Carbonyls.

| Entry | Substrate | Time | % Yield$^b$ |
|---|---|---|---|
| 1 | ![PhCH=NPh] | 5 h | 100 (98) |
| 2 | ![4-ClC6H4CH=NPh] | 24 h | 100 |
| 3 | ![2-MeOC6H4CH=NPh] | 24 h | 100 (90) |
| 4 | ![4-MeOC6H4CH=NPh] | 24 h | 100 (99) |
| 5 | ![PhCH=NCH2Ph] | 24 h | 100 |
| 6 | ![PhCH=N-4-BrC6H4] | 48 h | 70 |
| 7 | ![PhC(Me)=NPh] | 48 h | 100 |

TABLE 18-continued

Zr-MTBC-CoH-catalyzed Hydrogenation of Imines and Carbonyls.

| Entry | Substrate | Time | % Yield[b] |
|---|---|---|---|
| 8 | acetophenone | 48 h | 79 |
| 9 | 4′-chloroacetophenone | 48 h | 64 |
| 10 | cyclohexanone | 72 h | 76 |
| 11 | benzaldehyde | 48 h | 90 |

[a]Reaction conditions: 0.25 mg of Zr-MTBC-CoCl (0.5 mol % Co), 5 equiv of NaBEt$_3$H (1.0 M in THF) w.r.t. Co, alkene, toluene, 40 bar H$_2$, 80° C.
[b]Yields were determined by $^1$H NMR with mesitylene as the internal standard. Isolated yield in the parenthesis.

Example 16

Catalytic Hydrogenation of Heterocycles with Zr-MTBC-CoH

Zr-MTBC-CoH Catalyzed Hydrogenation of Benzofuran:

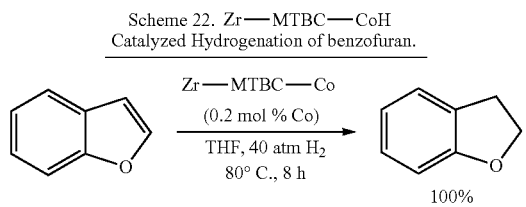

Scheme 22. Zr—MTBC—CoH Catalyzed Hydrogenation of benzofuran.

Scheme 22 shows the Zr-MTBC-CoH-catalyzed hydrogenation of an exemplary heterocycle, benzofuran. More particularly, in a glovebox, Zr-MTBC-CoCl in THF (0.5 mg, 0.2 mol % Co) was charged into a small vial and 0.5 mL THF was added. Then, 10 μL NaBEt$_3$H (1.0 M in THF) was added to the vial and the mixture was stirred slowly for 1 h in the glovebox. The solid was centrifuged out of suspension and then washed with THF two times. Then, the black solid in 0.5 mL THF was transferred to a vial containing 0.5 mL THF solution of benzofuran (30.0 mg, 0.254 mmol). The vial was placed into a Parr pressure reactor in a nitrogen-filled glovebox, then pressurized to bar. After stirring at 80° C. for 24 h, the solid was centrifuged out of suspension and extracted three times with THF. The combined organic extracts were concentrated in vacuo to afford crude 2,3-dihydrobenzofuran in quantitatively yield, which was sufficiently pure as determined by $^1$H NMR spectrum.

Summary:

The hydrogenation of heterocycles can be challenging due to their resonance stabilization and potential poisoning of catalysts by substrates and their products. Although significant progress has been made in developing precious metal-based molecular and heterogeneous catalysts for selective hydrogenation of N-heteoarenes such as indoles and quinolines, the advancement of the analogous earth abundant-metal catalysts has lagged behind. See Chen et al., J. Am. Chem. Soc., 2015, 137, 11718-11724; and Xu et al., ACS Catal., 2015, 5, 6350-6354. Catalytic hydrogenation of O-heteroarenes such as furans and benzofurans is also significantly under-developed. Additionally, the hydrogenation of heteroarenes typically requires harsh reaction conditions, high catalyst loadings, and excess additives.

At a 0.5 mol % Co loading, Zr-MTBC-CoH catalyzed hydrogenation of indole in toluene at 80° C. to afford a mixture of indoline and 4,5,6,7-tetrahydroindole. Indoline was obtained in 84% isolated yield after preparative TLC. See first entry, Table 19, below. Hydrogenation of 3-methyl-indole gave 3-methyl-indoline and 3-methyl-4,5,6,7-tetra-hydroindole in 46:54 ratio, which indicates that reduction of the phenyl ring is also possible. Hydrogenation of quinolines in toluene at 80° C. gave a mixture of two products, 1,2,3,4-tetrahydroquinoline and 5,6,7,8-tetrahydro-quinoline in a 1:1 ratio. Under identical reaction conditions, the selectivity appears dependent on the substitution of the phenyl ring. Electron-donating substituents at the 6-position of the quinolines favor the hydrogenation of the phenyl ring. For example, the 6-methylquinoline, 6-methoxyquinoline and 2,6-dimethylquinoline were hydrogenated to give 6-methyl-5,6,7,8-tetrahydro-quinoline, 6-methoxy-5,6,7,8-tetrahydro-quinoline and 2,6-dimethyl-5,6,7,8-tetrahydro-quinoline, respectively, as the major products. See Table 19. In contrast, strong electron-withdrawing substituents seem to disfavor the reduction of the phenyl ring. The hydrogenation of 2-methyl-6-fluoro-quinoline afforded 2-methyl-6-fluoro-1,2,3,4,-tetrahydro-quinoline exclusively in 72% yield. See second to last entry, Table 19. Zr-MTBC-CoH was also an active catalyst for hydrogenation of benzofuran. At a 0.2 mol % Co loading, benzofuran was completely hydrogenated to 2,3-dihydrobenzofuran in qualitative yield. See next to last entry, Table 19.

TABLE 19

Zr-MTBC-CoH-catalyzed Hydrogenation of Heterocycles.

| Substrate | Product | Mol % Co | Time | Yield[b] |
|---|---|---|---|---|
| indole | indoline + 4,5,6,7-tetrahydroindole | 0.5 | 66 h | 84 (93:7) |

TABLE 19-continued

Zr-MTBC-CoH-catalyzed Hydrogenation of Heterocycles.

| Substrate | Product | Mol % Co | Time | Yield[b] |
|---|---|---|---|---|
| 3-methylindole | 3-methylindoline + 3-methyl-4,5,6,7-tetrahydroindole | 0.5 | 72 h | 87 (46:54) |
| 6-chloroindole | 6-chloroindoline | 0.5 | 72 h | 16[d] |
| quinoline | 5,6,7,8-tetrahydroquinoline + 1,2,3,4-tetrahydroquinoline | 0.5 | 48 h | 95 (50:50) |
| 6-methylquinoline | 6-methyl-5,6,7,8-tetrahydroquinoline + 6-methyl-1,2,3,4-tetrahydroquinoline | 0.5 | 48 h | 100 (60:40) |
| 6-methoxyquinoline | 6-methoxy-5,6,7,8-tetrahydroquinoline + 6-methoxy-1,2,3,4-tetrahydroquinoline | 0.5 | 48 h | 82 (74:26) |
| 2,6-dimethylquinoline | 2,6-dimethyl-5,6,7,8-tetrahydroquinoline + 2,6-dimethyl-1,2,3,4-tetrahydroquinoline | 0.2 | 48 h | 100 (84:16) |
| 6-fluoro-2-methylquinoline | 6-fluoro-2-methyl-1,2,3,4-tetrahydroquinoline | 0.2 | 48 h | 100 (72) |
| benzofuran | 2,3-dihydrobenzofuran | 0.2 | 8 h | 100 |
| benzothiophene | 2,3-dihydrobenzothiophene | 0.2 | 48 h | 0 |

[a]Reaction conditions: 0.25 mg of Zr-MTBC-CoCl, 5 equiv of NaBEt$_3$H (1.0 M in THF) w.r.t. Co, alkene, toluene (2 mL), 40 bar H$_2$, 80° C.
[b]Yields were determined by $^1$H NMR with mesitylene as the internal standard. Ratios of the products, as determined by GC-MS, are in the parenthesis.
[c]Reaction was performed at 100° C.
[d]Yields determined by GC-MS analysis.

Example 17

Synthesis and Characterization of Zr$_{12}$-TPDC

Synthesis of Zr$_{12}$-TPDC

To a 20 mL vial was added ZrCl$_4$ (4.2 mg, 18 μmol), H$_2$TPDC (5.7 mg, 18 mmol), acetic acid (0.75 mL), and DMF (10 mL). The mixture was sonicated for 5 min until all solids were dispersed and then kept in a 120° C. oven for 3 d. 3.1 mg of Zr$_{12}$-TPDC (48% yield) was obtained as light gray powder.

Figure 22:
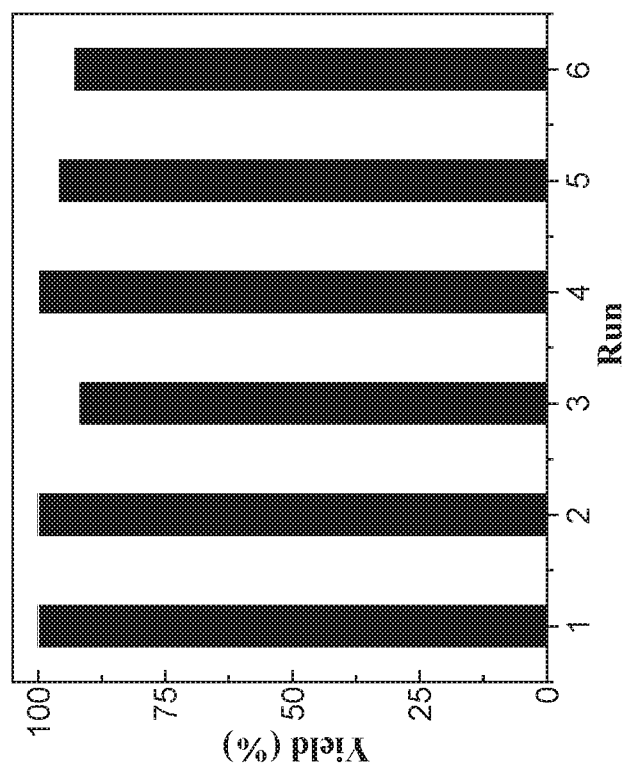
FIG. 22 is a transmission electron microscopy (TEM) image of a metal organic framework prepared from zirconium tetrachloride ($ZrCl_4$) and p,p'-terphenyldicarboxylic acid (TPDC), designated $Zr_{12}$-TPDC.
Figure 23:
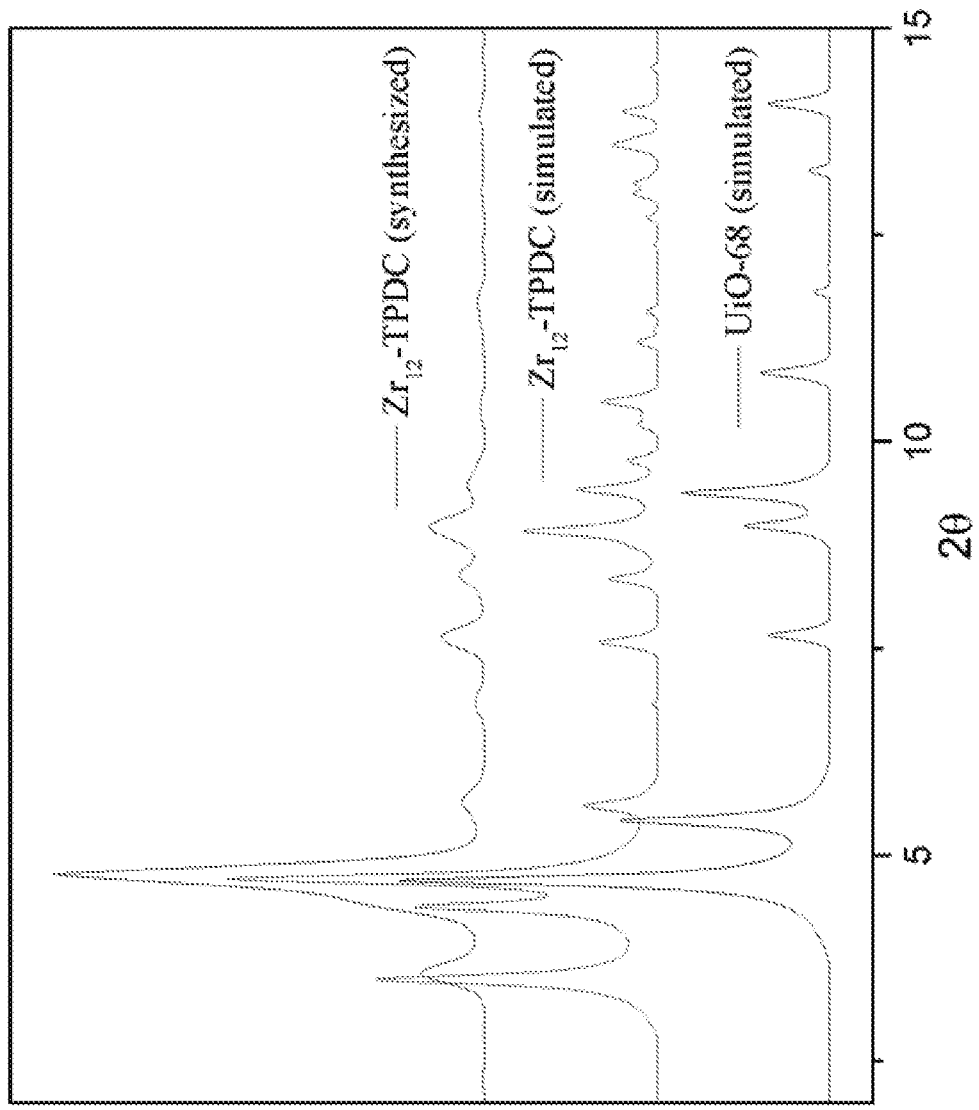
FIG. 23 is a graph of the simulated and experimental (synthesized) powder x-ray diffraction (PXRD) patterns of the as-synthesized metal organic framework ($Zr_{12}$-TPDC) described in FIG. 22. For comparison, a simulated PXRD pattern for the metal organic framework (UiO-68) having a $Zr_6$ secondary building unit and the same TPDC linker.
Figure 24B:
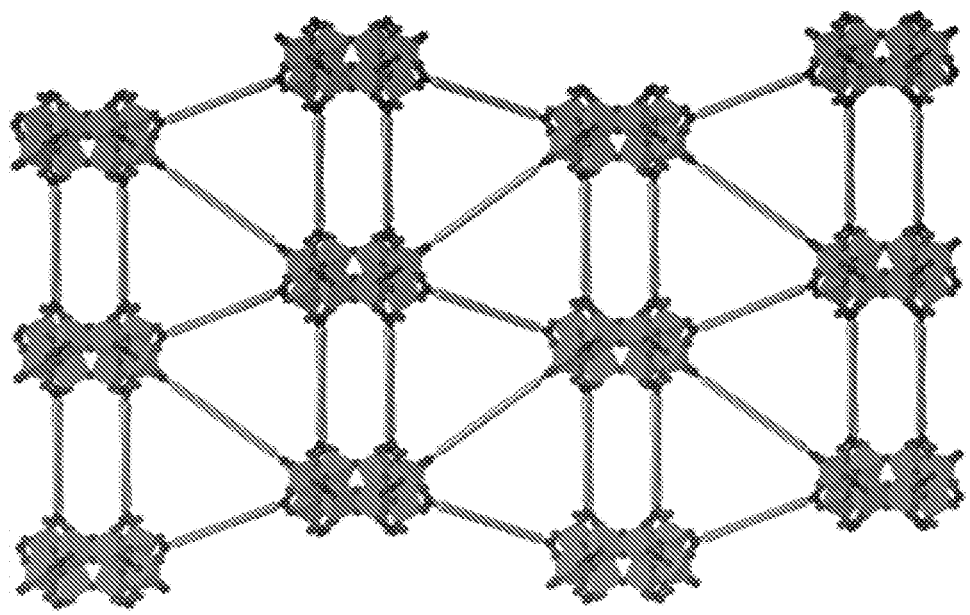
FIG. 24B is a schematic drawing showing a ball and stick model of the metal organic framework ($Zr_{12}$-TPDC) described for FIG. 22 as viewed along the [110] plane.
Figure 24A:
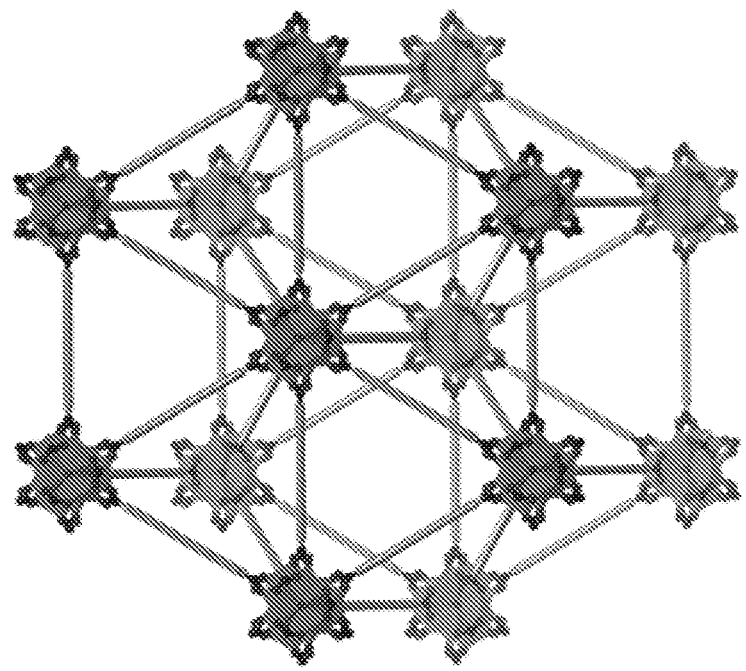
FIG. 24A is a schematic drawing showing a ball and stick model of the metal organic framework ($Zr_{12}$-TPDC) described for FIG. 22 as viewed along the [002] plane.

Characterization of Zr$_{12}$-TPDC:

FIG. 22 shows a transmission electron microscopy micrograph of the as-synthesized Zμ$_2$-TPDC, showing a size distribution of about 50 nm. FIG. 23 shows the similarly between the PXRD patterns of Zr$_{12}$-TPDC (top) with the simulated PXRD pattern (middle). The PXRD pattern of the Zr$_{12}$-TPDC MOF is different from the UiO-68 MOF, which has a Zr$_6$ SBU and the same TPDC linker. See FIG. 23,

Example 18

Synthesis and Characterization of $Zr_{12}$-TPDC-Co

Figure 25:
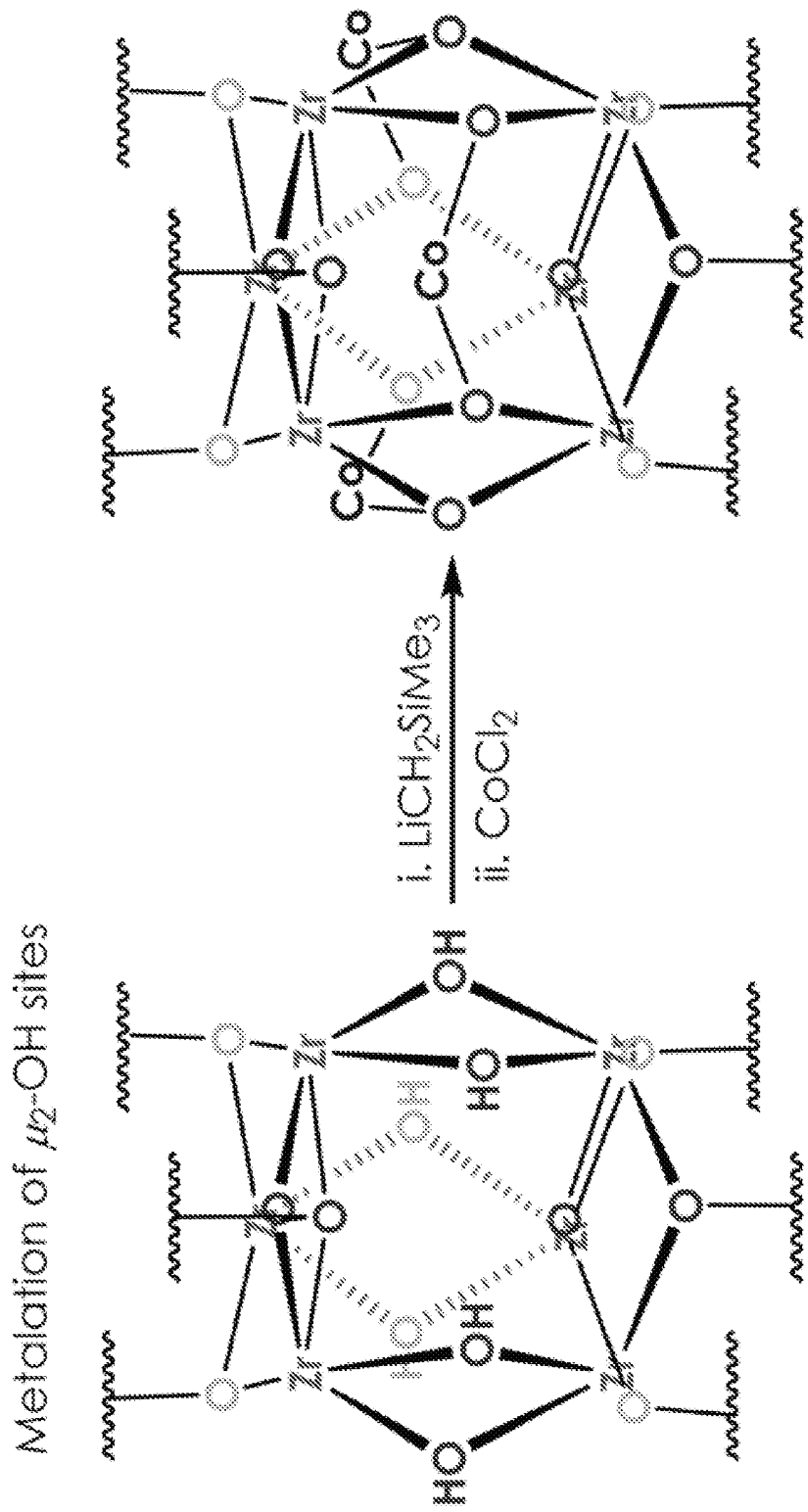
FIG. 25 is a schematic drawing showing a proposed metalation mode for zirconium $(Zr)_{12}$ secondary building unit (SBU) $\mu_2$-OH sites with cobalt chloride ($CoCl_2$). Trimethylsilylmethyllithium ($LiCH_2SiMe_3$) is used to deprotonate the hydroxyl groups.

In a glovebox, $Zr_{12}$-TPDC (14 mg) in 4 mL THF was cooled to −30° C. for 30 min. To the cold suspension, $LiCH_2SiMe_3$ (1 M in pentane, 0.17 mL, 5 equiv. to μ-OH) was added dropwise and the resultant light green-yellow mixture was stirred slowly for 1 h at room temperature. The light yellow solid was collected after centrifugation, and washed with THF 5-6 times. Then, the lithiated $Zr_{12}$-TPDC was transferred to a vial containing 4 mL THF solution of $CoCl_2$ (6.6 mg, 1.5 equiv. to —OLi). The mixture was stirred for 12 h and the deep blue solid was then centrifuged and washed with THF 5 times. The metalated MOFs were stored in THF in the glovebox for further use. ICP-MS analysis indicates Co/Zr ratio of 1.1. FIG. 25 shows a schematic drawing of the proposed metalation mode of $CoCl_2$ to $Zr_{12}$—SBU $μ_2$-OH sites.

Example 19

$Zr_{12}$-TPDC-Co Catalyzed Hydrogenation of Nitroarenes

Scheme 23. $Zr_{12}$—MOF—Co Catalyzed Hydrogenation of Nitroarenes

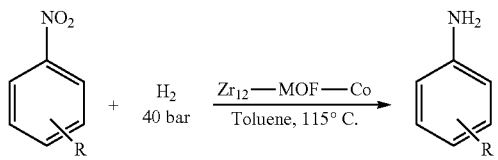

General Procedure for $Zr_{12}$-TPDC-CoH Catalyzed Hydrogenation of Nitroarenes:

Scheme 23 shows the hydrogenation of nitroarenes catalyzed by $Zr_{12}$-TPDC-Co. In a nitrogen-filled glove box, $Zr_{12}$-TPDC-CoH (0.50 mg) in 1.0 mL THF was charged into a glass vial. $NaBEt_3H$ (10 μL, 1.0 M in THF) was then added to the vial and the mixture was stirred for 1 h. The solid was then centrifuged, washed with THF twice, and transferred to a glass vial in 1.0 mL toluene. The nitroarene substrate was added to the vial, which was placed in a Parr reactor, sealed under nitrogen, and charged with hydrogen to 40 bar. After stirring at 115° C. for 1-2 d, the pressure was released and the MOF catalyst was removed from the reaction mixture via centrifugation. Mesitylene (internal standard) was added to the organic extracts and the yield of the product was determined by integrations of the product and mesitylene peaks in the $^1H$ NMR spectra in $CDCl_3$.

$Zr_{12}$-TPDC-CoH Catalyzed Hydrogenation of 4-Nitroanisole:

In a glovebox, $Zr_{12}$-TPDC-CoH in THF (0.50 mg, 0.5 mol % Co) was charged into a small vial and 0.5 mL THF was added. Then, 10 μL $NaBEt_3H$ (1.0 M in THF) was added to the vial and the mixture was stirred slowly for 1 h in the glovebox. The solid was centrifuged out of suspension and then washed with THF two times. Then, the black solid in 1.0 mL toluene was transferred to a vial containing 4-nitroanisole. The vial was placed into a Parr pressure reactor in a nitrogen-filled glovebox, then pressurized to 40 bar. After stirring at 115° C. for 44 h, the solid was centrifuged out of suspension and extracted three times with THF. The combined organic extracts were concentrated in vacuo to afford crude aniline in quantitatively yield, which was sufficiently pure as analyzed by $^1H$ NMR spectrum.

Summary: Table 20, below summarizes the optimization of conditions for the MOF-CoH catalyzed hydrogenation of nitroarenes using nitrobenzene as an exemplary nitroarene. Table 21 summarizes results of the hydrogenation of various nitroarenes using $Zr_{12}$-TDPC-CoH.

TABLE 20

Optimization of conditions for MOF-CoH catalyzed hydrogenation of nitroarenes.

| Entry | Catalyst | Temp./° C. | Loading/% | Time/h | % Yield |
|---|---|---|---|---|---|
| 1[b] | Co-NP | 115 | 0.5 | 22 | 5 |
| 2 | UiO-68-Co | 115 | 1.0 | 40 | 87 |
| 3 | UiO-68-Fe | 115 | 1.0 | 40 | 59 |
| 4 | $Zr_{12}$-MOF-Co | 105 | 1.0 | 40 | 86 |
| 5 | $Zr_{12}$-MOF-Co | 115 | 0.5 | 44 | 99 |
| 6 | $Zr_{12}$-MOF-Ni | 105 | 1.0 | 41 | 42 |

TABLE 21

$Zr_{12}$-TPDC-CoH catalyzed hydrogenation of nitroarenes.

| reactant | product | Loading | Time/hr | % Yield[a]/% |
|---|---|---|---|---|
| NO₂-phenyl | NH₂-phenyl | 0.5 | 44 | 99 |

TABLE 21-continued

Zr$_{12}$-TPDC-CoH catalyzed hydrogenation of nitroarenes.

| reactant | product | % Loading | Time/hr | Yield$^a$/% |
|---|---|---|---|---|
| 4-bromonitrobenzene | 4-bromoaniline | 0.5 | 43 | 70 |
| 4-nitroanisole | 4-methoxyaniline | 0.5 | 44 | 100 |
| 1-nitronaphthalene | 1-naphthylamine | 0.5 | 43 | 100 |
| 4-nitrobenzotrifluoride | 4-(trifluoromethyl)aniline | 0.5 | 43 | 100 |
| 2-bromonitrobenzene | 2-bromoaniline | 0.5 | 43 | 98 |
| 4-nitrotoluene | 4-methylaniline | 0.5 | 43 | 41 |
| 2-methyl-1,4-dinitrobenzene | 2-methyl-4-nitroaniline | 0.5 | 43 | 10 |
| 4-nitroindole | 4-aminoindole | 1.0 | 72 | 55 |

TABLE 21-continued

Zr$_{12}$-TPDC-CoH catalyzed hydrogenation of nitroarenes.

| reactant | product | % Loading | Time/hr | Yield$^a$/% |
|---|---|---|---|---|
| 5-nitroindole | 5-aminoindole | 1 | 42 | 60 |
| 4-nitro-N,N-dimethylaniline | 4-amino-N,N-dimethylaniline | 0.5 | 42 | 47 |
| 4-nitro-N-methylaniline | 4-amino-N-methylaniline | 1.0 | 40 | 100 |
| 4-nitrobenzophenone | 4-aminobenzophenone | 1.0 | 42 | 34 |
| 4′-nitroacetophenone | 4′-aminoacetophenone | 2 | 44 | 54 |
| nitrosobenzene | aniline | 0.5 | 40 | 100 |

Example 20

General Methods for Examples 21-26

All of the reactions and manipulations were carried out under nitrogen with the use of standard inner atmosphere and Schlenk techniques unless otherwise indicated. Tetrahydrofuran was purified by passing through a neutral alumina column under $N_2$. d$_6$-Benzene was distilled over CaH$_2$. Alkenes and pyridine derivatives were purchased from Fisher (Thermo Fischer Scientific, Waltham, Mass., United States of America), distilled and then dried over 4 Å molecular sieves prior to use. $(NH_4)_2Ce(NO_3)_6$ was purchased from Sigma-Aldrich (St. Louis, Mo., United States of America) and used as received. Powder X-ray diffraction data were collected on Bruker D8 Venture diffractometer (Bruker Corporation, Billerica, Mass., United States of America) using Cu Kα radiation source (I=1.54178 Å). Nitrogen adsorption experiments were performed on a Micrometrics TriStar II 3020 instrument (Micrometrics Instrument Corporation, Norcross, Ga., United States of America). Thermogravimetric analysis (TGA) was performed in air using a Shimazu TGA-50 (Shimadzu Corporation, Kyoto, Japan) equipped with a platinum pan and heated at a rate of 3° C. per min. $^1$H NMR spectra were recorded on a Bruker NMR 500 DRX spectrometer (Bruker Corporation, Billerica, Mass., United States of America) at 500 MHz or a Bruker NMR 400 DRX spectrometer (Bruker Corporation, Billerica, Mass., United States of America) at 400 MHz, and referenced to the proton resonance resulting from incomplete deuteration of the CDCl$_3$ (δ 7.26) or C$_6$D$_6$ (δ 7.14). $^{13}$C NMR spectra were recorded at 125 MHz, and all of the chemical shifts were reported downfield in ppm relative to the carbon resonance of CDCl$_3$ (δ77.00) or C$_6$D$_6$ (δ128.00). $^{11}$B NMR spectra were recorded at 128 MHz, and all of the chemical shifts were reported downfield in ppm relative to an external BF$_3$.OEt$_2$ standard. The following abbreviations are used here: s: singlet, d: doublet, t: triplet, q: quartet, m: multiplet, br: broad, app: apparent. Gas chromatography data were obtained on an Agilent 7890B Gas Chromatograph (Agilent Technologies, Santa Clara, Calif., United States of America). ICP-MS data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a $^{159}Tb$ internal standard against a 12-point standard curve over the range from 0.1 ppb to 500 ppb. The correlation was >0.9997 for all analyses of interest. Data collection was performed in Spectrum Mode with five replicates per sample and 100 sweeps per replicates.

Example 21

Synthesis and Characterization of Ce-BTC

Ce-BTC Synthesis:

$(NH_4)_2Ce(NO_3)_6$ (117 mg) was dissolved in $H_2O$ (0.4 mL) at 100° C. under stirring, followed by the dropwise addition of a trimesic acid ($H_3BTC$, 15 mg) solution in DMF (1.2 mL). The solution was kept at 100° C. to afford Ce-BTC as a yellow solid. The resultant MOF was centrifuged, then washed with DMF twice and DMSO twice to remove residual metal and ligand precursors. After freeze-drying with benzene, the MOF sample was stored in a nitrogen-filled glove box.

Structure Analysis of Ce-BTC MOF:

Despite the good crystallinity of Ce-BTC as evident in the powder X-ray diffraction pattern, diffraction quality single crystals were not obtained after numerous attempts. The structure of Ce-BTC was simulated based on the reported structure of Zr-BTC (MOF-808). See Furukawa et al., J. Am. Chem. Soc., 2014, 136, 4369-4381. The good match between simulated pattern and experimental data confirmed that Ce-BTC adopts the spn topology. One important structural difference between $Ce_6$ clusters versus $Zr_6$ clusters is the longer Ce—Ce distance (3.74 Å) compared to Zr—Zr distance (3.50 Å).

X-Ray Absorption Spectroscopy:

X-ray absorption data were collected at Beamline 10-BM-A, B (Ce-BTC) and Beamline 9-BM (CeOH-BTC and CeH-BTC) at the Advanced Photon Source (APS) at Argonne National Laboratory. Spectra were collected at the cerium L3-edge (5723 eV) in transmission mode. The X-ray beam was monochromatized by a Si(111) monochromater and detuned by 50% to reduce the contribution of higher-order harmonics below the level of noise. A metallic chromium foil standard was used as a reference for energy calibration and was measured simultaneously with experimental samples. The incident beam intensity ($I_0$), transmitted beam intensity ($I_t$), and reference ($I_r$) were measured by 20 cm ionization chambers with gas compositions of 29% $N_2$ and 71% He, 90% $N_2$ and 70% Ar, and 100% $N_2$, respectively. Data were collected over five regions: −250 to −30 eV (10 eV step size, dwell time of 0.25 s), −30 to −12 eV (5 eV step size, dwell time of 0.5 s), −12 to 30 eV (0.3 eV step size, dwell time of 1 s), 30 eV to 6 Å$^{-1}$, (0.05 Å$^{-1}$ step size, dwell time of 2 s), 6 Å$^{-1}$ to 10 Å$^{-1}$, (0.05 Å$^{-1}$ step size, dwell time of 8 s). Multiple X-ray absorption spectra were collected at room temperature for each sample. Samples were ground and mixed with polyethyleneglycol (PEG) and packed in a 6-shooter sample holder to achieve adequate absorption length.

Data were processed using the Athena and Artemis programs of the IFEFFIT package based on FEFF 6. See Rehr et al., Rev. Mod. Phys., 2000, 72, 621-654; and Ravel et al., J. Synchrotron Rad., 2005, 12, 537-541. Prior to merging, spectra were calibrated against the reference spectra and aligned to the first peak in the smoothed first derivative of the absorption spectrum, the background noise was removed, and the spectra were processed to obtain a normalized unit edge step.

Figure 26:
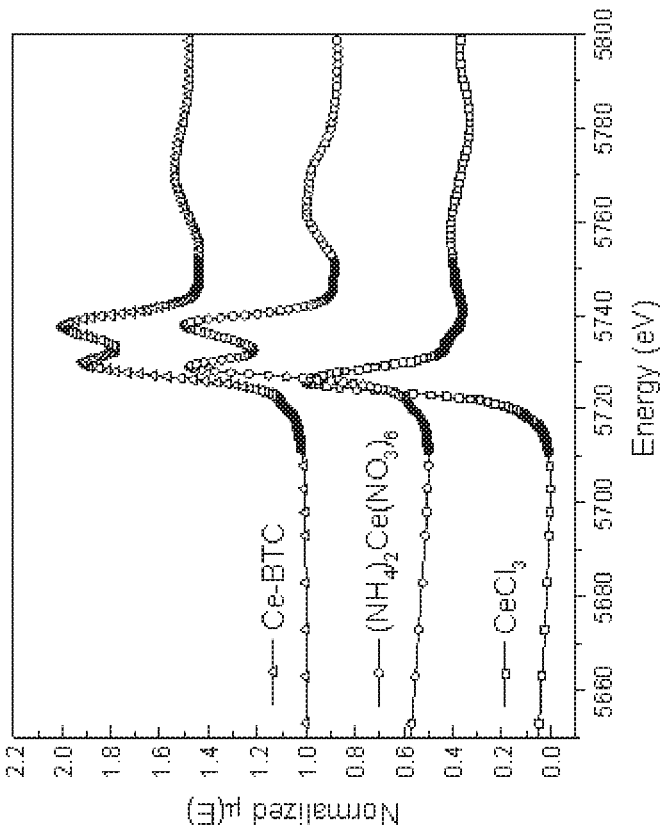
FIG. 26 is a graph of the x-ray absorption near edge structure (XANES) spectra of a metal organic framework (Ce-BTC) comprising cerium oxo clusters and trimesic acid as the organic bridging ligand, cerium trichloride ($CrCl_3$) and ammonium cerium(IV) nitrate (($NH_4)_2Ce(NO_3)_6$). The spectra of Ce-BTC and $(NH_4)_2Ce(NO_3)_6$ are similar, indicating a +4 oxidation state for the cerium centers in the Ce-BTC.

XANES Analysis of Ce Oxidation States:

The Ce oxidation states of in Ce-BTC was determined by comparing the edge feature with those of $Ce^{(III)}Cl_3$ and $(NH_4)_2Ce^{(IV)}(NO_3)_6$. See FIG. 26. Similar to the $Ce^{(IV)}$ reference, Ce-BTC shows two adsorption peaks at 5730 eV and 5738 eV. This indicates the $Ce^{(IV)}$ precursor was not reduced by DMF or water during MOF growth. The $Ce^{(III)}$ reference compound, in comparison, only shows one distinct peak at 5726 eV.

Figure 27:
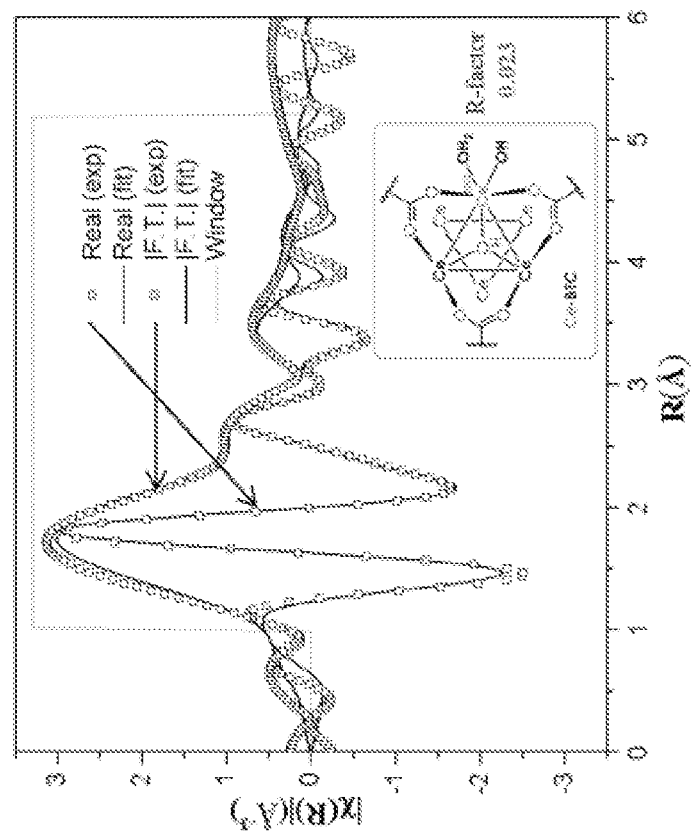
FIG. 27 is a graph of extended x-ray absorption fine structure (EXAFS) spectra fitting on the metal organic framework (Ce-BTC) described in FIG. 26 with the $[(\mu_3\text{-}O)_2(\mu_3\text{-}OH)_2(\mu_2\text{-}CO_2^-)_2]Ce(OH)(OH_2)$ coordination environment, giving an R-ractor of 0.023.

XAFS Fitting Using the Simulated Ce-BTC Structure:

EXFAS fitting on Ce-BTC with the $[(\mu_3\text{-}O)_2(\mu_3\text{-}OH)_2(\mu_2\text{-}CO_2^-)_2]Ce(OH)(OH_2)$ coordination environment gives an R-factor of 0.023. See FIG. 27. Table 22 provides a summary of the EXAFS fitting parameters for Ce-BTC.

TABLE 22

Summary of EXAFS fitting parameters for Ce-BTC

| Sample | Ce-BTC | |
|---|---|---|
| Fitting range | k 2.4-7.2 Å$^{-1}$ R 1.0-5.2 Å | |
| Independent points | 13 | |
| Variables | 8 | |
| Reduced chi-square | 95 | |
| R-factor | 0.02 | |
| $S_0^2$ | 1.000 | |
| $\Delta E_0$(eV) | 5.91 ± 1.59 | |
| R (Ce-$\mu_3$-O) (Å) | 2.18 ± 0.02 | N = 4 |
| R (Ce—O$^{CO2-}$) (Å) | 2.39 ± 0.02 | N = 2 |
| R (Ce-$\mu_1$-O) (Å) | 2.43 ± 0.02 | N = 2 |
| R (Ce—Ce) (Å) | 3.82 ± 0.07 | N = 4 |
| R (Ce—C$^{CO2-}$) (Å) | 3.73 ± 0.30 | N = 2 |
| R(Ce—O$^{CO2\text{-}distal}$) (Å) | 3.84 ± 0.02 | N = 2 |

Adsorption Isotherm of Ce-BTC:

The nitrogen sorption isotherms of Ce-BTC (77K) gave a calculated BET surface area of 1008 m$^2$/g. DFT simulated cylinder-shape pore size distribution shows that Ce-BTC has the largest pore size of about 22 Å, which is consistent with the simulated Ce-BTC structure.

Figure 28:
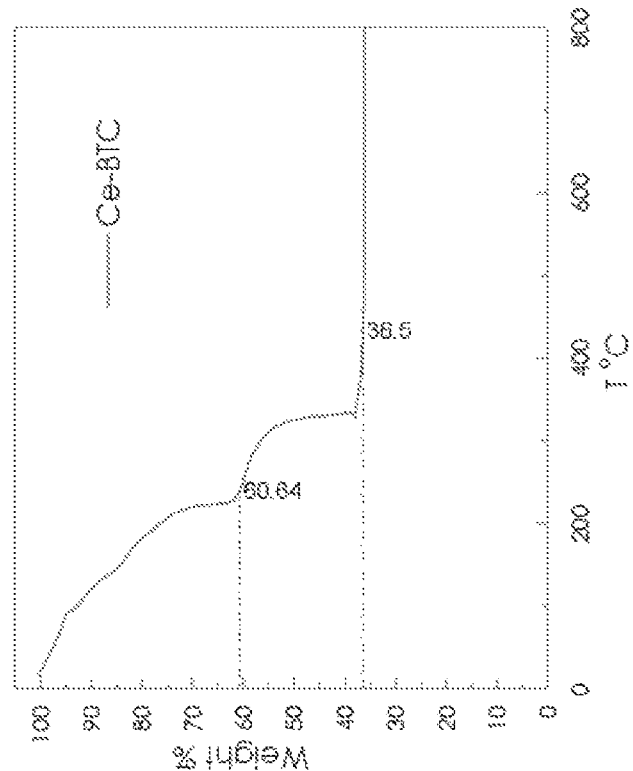
FIG. 28 is graph showing the thermogravimetric analysis (TGA) curves of the freshly prepared metal organic framework (Ce-BTC) described in FIG. 26 in the 25-800 degrees Celsius (° C.).

Thermogravimetric Analysis of Ce-BTC:

FIG. 28 shows the TGA curves of freshly prepared Ce-BTC in the 25-800° C. range. The first weight loss (39.4%) corresponds to the removal of coordinated water molecules on Ce centers and adsorbed solvents (e.g., benzene) in the pores. The second weight loss (39.8%) in the 240-800° C. temperature range corresponds to the decomposition of $Ce_6O_4(OH)_{10}(OH_2)_6(BTC)$.

Figure 29:
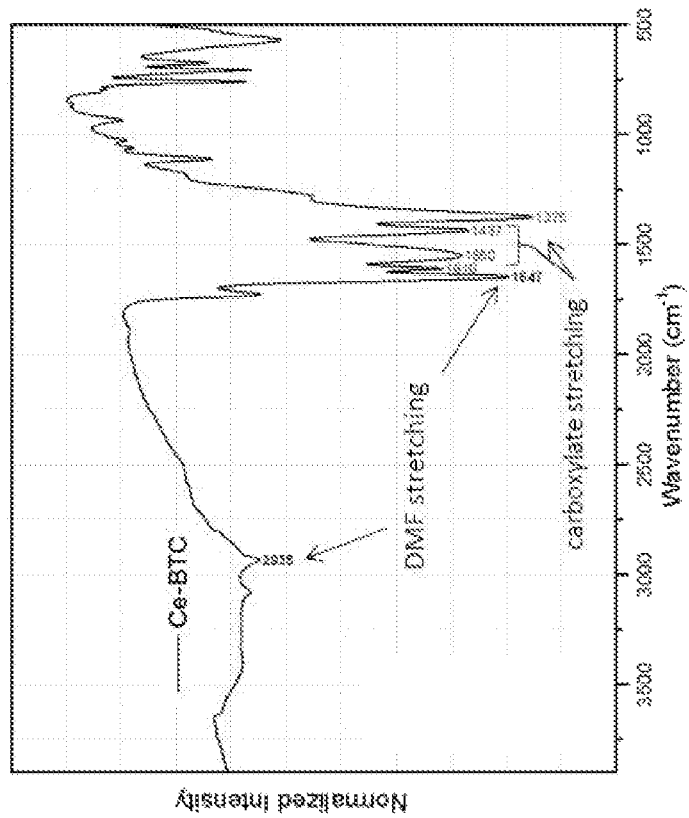
FIG. 29 is a graph of the infrared (IR) spectrum of the freshly prepared metal organic framework (Ce-BTC) described in FIG. 26. The carboxylate coordination peaks are observed in the 1375-1437 wavenumber ($cm^{-1}$) and 1550-1610 $cm^{-1}$ ranges. Peaks of adsorbed dimethylformamide (DMF) were also observed, including (=O)C—H stretching at 2935 $cm^{-1}$ and C=O stretching at 1647 $cm^{-1}$.

Infrared Spectra of Ce-BTC:

FIG. 29 shows the IR spectrum of freshly prepared Ce-BTC. The carboxylate coordination peaks were observed in 1375~1437 cm$^{-1}$ and 1550-1610 cm$^{-1}$. Peaks of adsorbed DMF molecules were also observed, including (O=)C—H stretching frequency at 2935 cm$^{-1}$ and C=O stretching frequency at 1647 cm$^{-1}$.

$^1$H NMR of Digested Ce-BTC: $^1$H NMR of digested Ce-BTC (500 MHz, DMSO-d) indicates that DMF and $C_6H_6$ are trapped solvents within the MOF pore. Approximately 8 mol % of formic acid (relative to Ce) is seen in the spectrum, which is likely generated from hydrolysis of DMF.

Example 22

Synthesis and Characterization of CeH-BTC

Procedure for Ce-BTC Lithiation and Reduction:

In a glovebox, Ce-BTC (20.0 µmol of Ce) was weighed out in a 1.5 mL centrifuge tube, and washed with THF three times through centrifugation, and then dispersed in 1.0 mL of benzene. LiCH$_2$SiMe$_3$ (0.2 mL, 0.2 mmol, 1.0 M solution in pentane) was added dropwise to the suspension. The color of the MOF immediately changed from yellow to orange. The resultant mixture was kept at room temperature overnight to ensure complete lithiation. The orange solid of CeOH-BTC was then centrifuged out of suspension and washed with benzene 3 times to remove excess LiCH$_2$SiMe$_3$. ICP-MS of the digested CeOH-BTC sample shows a Li/Ce ration of 1.69±0.05, consistent with the deprotonation of the Ce$_6$($\mu_3$-O)$_4$($\mu_3$-OH)$_4$(OH)(OH$_2$) SBU to form the [Ce($\mu_3$—O)$_4$($\mu_3$-OLi)$_4$(OH)$_2$]Li$_6$ SBU.

The obtained CeOH-BTC suspension in benzene was transferred into a J-Young tube and treated with HBpin (0.2 µmol, 29 µL), then heated at 80° C. for 2 h. Head-space gas was analyzed by GC, and the CeH-BTC was analyzed by XAS.

Figure 30:
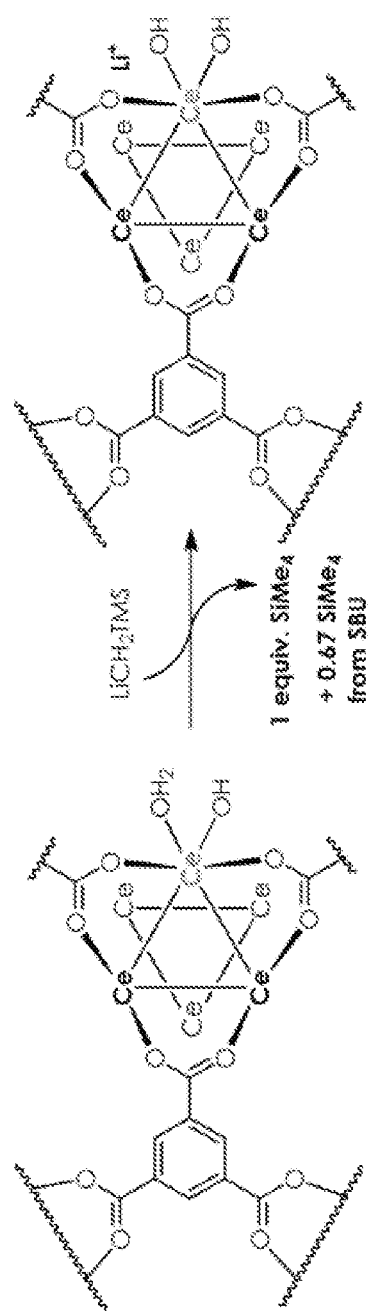
FIG. 30 is a schematic drawing of a proposed deprotonation mechanism of the metal organic framework (Ce-BTC) described in FIG. 26 with trimethylsilylmethyllithium (LiCH$_2$SiMe$_3$). The proposed mechanism is supported by tetramethylsilane (SiMe$_4$) quantification by proton nuclear magnetic resonance spectroscopy studies and lithium/cerium quantification by inductively-coupled plasma mass spectroscopy.

SiMe$_4$ Quantification Study:

After activation with LiCH$_2$SiMe$_3$ overnight using the aforementioned procedure, 5 equivalent of cyclohexane (100 µmol) was added to the suspension as internal standard for $^1$H NMR. The MOF was removed by centrifugation, and one drop of supernatant was diluted with C$_6$D$_6$ and used for $^1$H NMR. 1.74±0.15 equivalent of SiMe$_4$ per Ce was detected after repeating the same experiment for three runs, very close to calculated 1.67 equiv. from the proposed reaction. Based on experimental results and literature precedents, a possible activation pathway is presented in FIG. 30.

Figure 31:
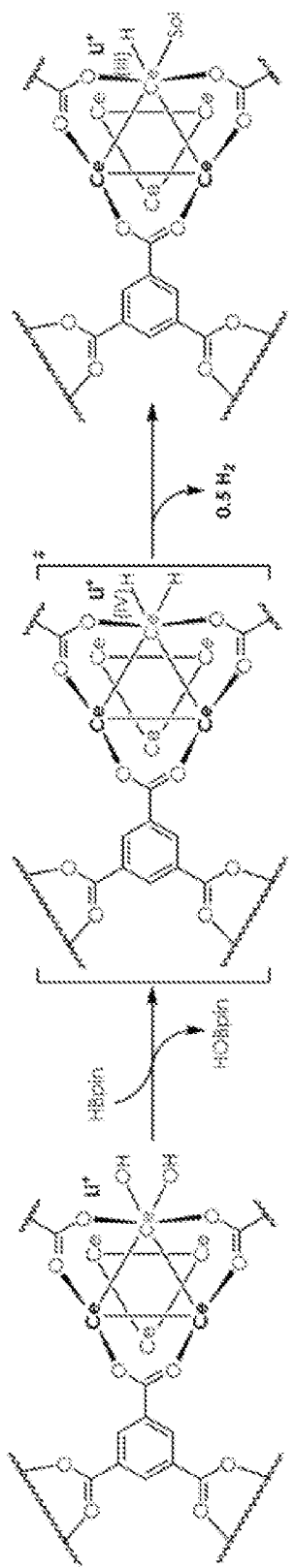
FIG. 31 is a schematic drawing of a proposed mechanism for cerium (IV) (Ce$^{IV}$) reduction.

HOBpin Quantification:

Without being bound to any one theory, a mechanism of the Ce$^{IV}$ reduction is proposed as follows: Pinacolborane undergoes anion exchange with [Ce$^{IV}$(OH)$_2$]Li to generate unstable [Ce(H)$_2$]Li, which quickly goes through bimetallic reductive elimination to form Ce$^{III}$—H, with the concomitant formation of 0.5 equiv. of H$_2$ w.r.t. Ce. See FIG. 31.

As support of this mechanism, a GC trace of head-space gases in J. Young tubes during the reduction of CeOH-BTC by HBpin shows consistent results across three different runs. The amount of H$_2$, after subtraction of background, was calculated to be 10.2 µmol, which corresponds to 0.51±0.013 equiv. of H$_2$ w.r.t. Ce.

The identity of HOBpin was confirmed by $^{11}$B NMR (CDCl$_3$, 128 MHz). Peak position of detected boron species at δ 21.7 ppm matched well with the HO-Bpin standard at δ 22.7 ppm. No peak matching HBpin at δ 28.4 was observed. $^1$H NMR Quantification of HOBpin was performed in three runs using MeNO$_2$ (2 equiv. to Ce) as internal standard. 1.01±0.07 equiv. of HOBpin was detected w.r.t. Ce.

BET Analysis of CeH-BTC:

Nitrogen sorption isotherms of CeH-BTC (77K) indicated that CeH-BTC has a BET surface area of 721 m$^2$/g. The pore size distributions of CeH-BTC suggested pores of 15 Å and 19 Å.

Figure 32:
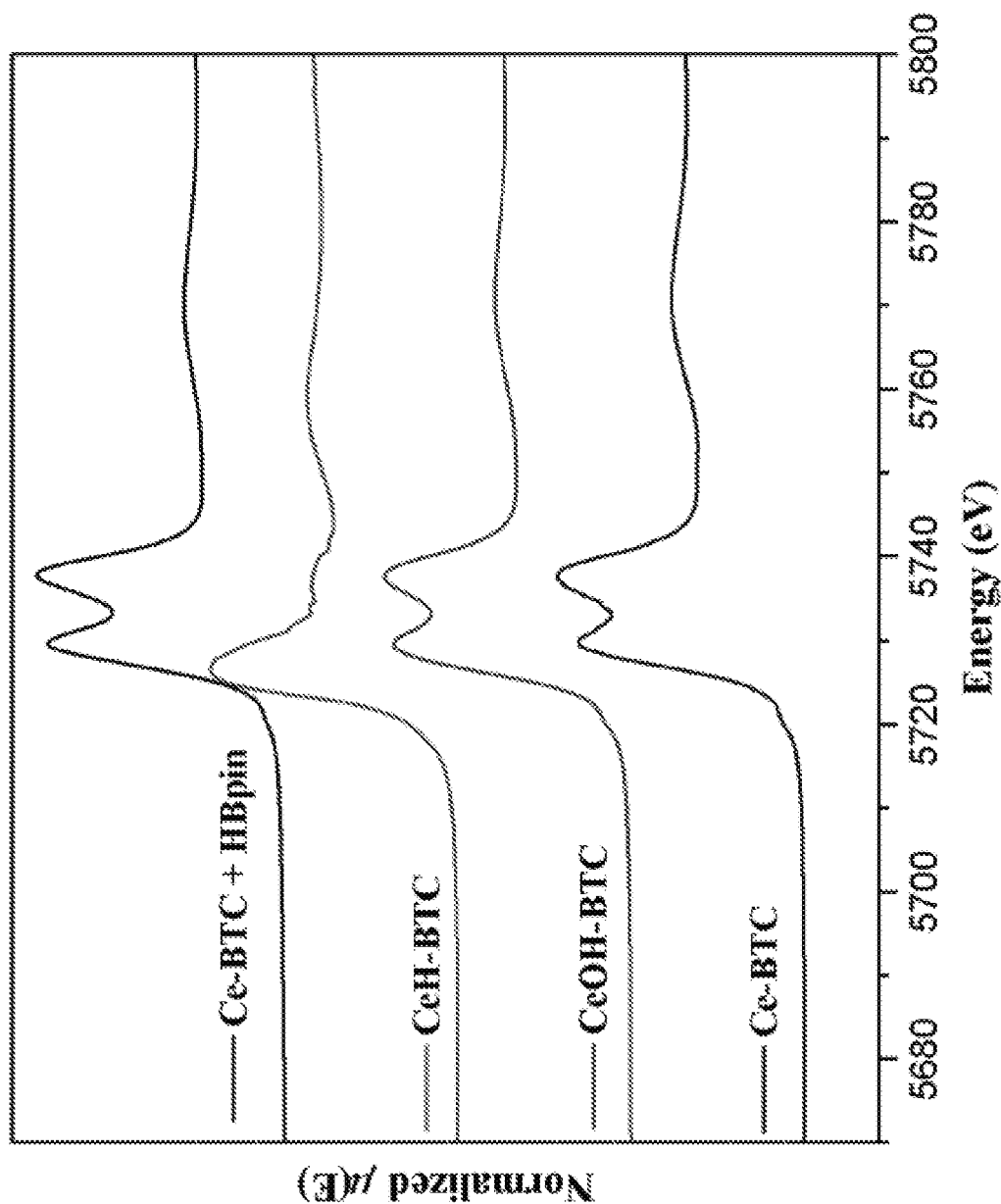
FIG. 32 is a graph of the x-ray absorption near edge structure (XANES) spectra of a metal organic framework (Ce-BTC) comprising cerium oxo clusters and trimesic acid as the organic bridging ligand; the metal organic framework after treatment with trimethylsilylmethyllithium (CeOH-BTC), the metal organic framework after reduction (CeH-BTC), and the non-lithiated Ce-BTC treated with a reducing agent (Cr-BTC+HBpin). The spectra indicate that lithiation does not change the cerium oxidation state, but that it does change from +4 to +3 after post-lithiation reduction.

XANES Analysis:

XANES analyses (see FIG. 32) show that CeOH-BTC (FIG. 32, line second from bottom) remains at +4 oxidation state, identical to Ce-BTC (FIG. 32, bottom line), indicating LiCH$_2$SiMe$_3$ did not reduce the Ce from +4 to +3. Oxidation state of Ce in CeH-BTC (FIG. 32, line second from top) was identified as +3, indicating successful Ce reduction by HBpin. Non-lithiated Ce-BTC cannot be reduced with HBpin under identical reaction condition, as suggested by the XANES spectrum of Ce-BTC+HBpin (FIG. 32, top line). This study suggests that lithiation is important for Ce$_6$ SBU reduction.

Figure 33:
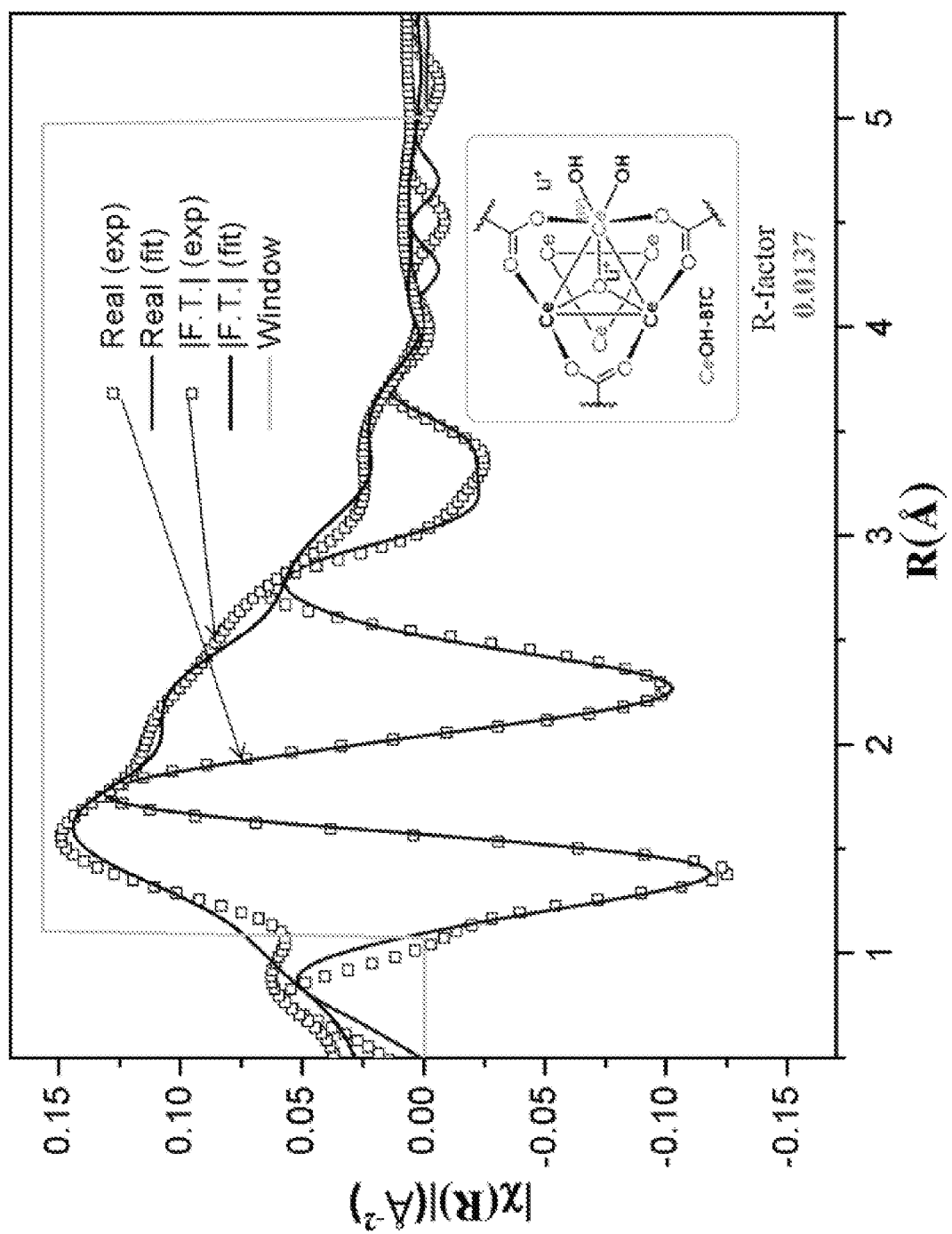
FIG. 33 is a graph of extended x-ray absorption fine structure (EXAFS) spectra fitting on the lithiated metal organic framework (CeOH-BTC) described in FIG. 32 with the [[($\mu_3$-O)$_2$($\mu_3$-OLi)$_2$($\mu_2$-CO$_2^-$)$_2$]Ce(OH)$_2$]Li coordination environment, giving an R-factor of 0.0137.
Figure 34:
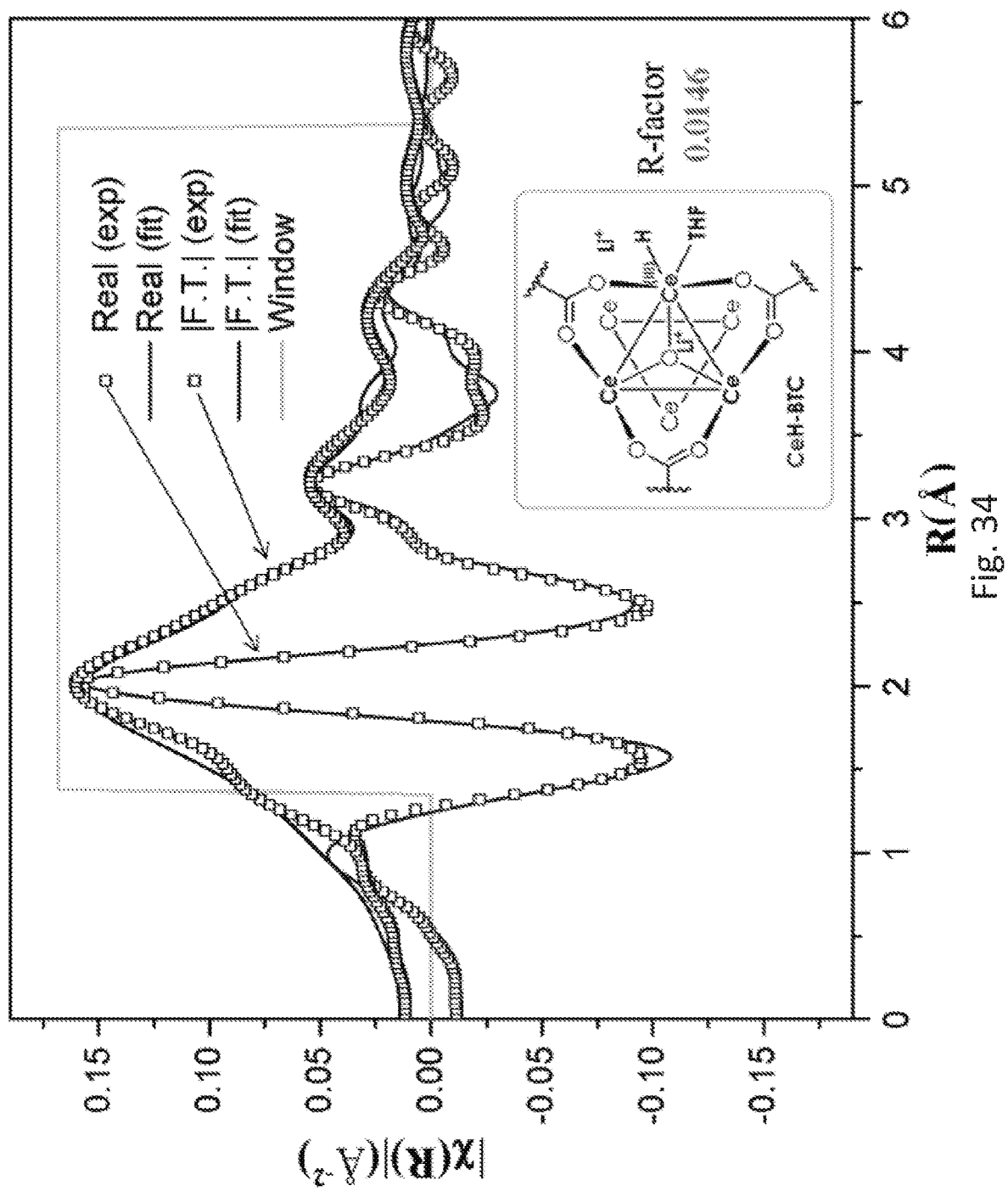
FIG. 34 is a graph of extended x-ray absorption fine structure (EXAFS) spectra fitting on the reduced metal organic framework (CeH-BTC) described in FIG. 32 with the [[($\mu_3$-O)$_2$($\mu_3$-OLi)$_2$($\mu_2$-CO$_2^-$)$_2$]Ce(H)(THF)]Li coordination environment, giving an R-factor of 0.0146.

XAFS Fitting for CeOH-BTC and CeH-BTC:

Tables 23 and 24, below, summarize the EXAFS fitting parameters for CeOH-BTC and CeH-BTC. FIG. 33 is a graph showing the fitting on EXAFS data of CeOH-BTC with the [[($\mu_3$-O)$_2$($\mu_3$-OLi)$_2$($\mu_2$-CO$_2^-$)$_2$]Ce(OH)$_2$]Li coordination environment gives an R-factor of 0.0137. FIG. 34 is a graph showing the fitting on EXAFS data of CeH-BTC with the [[($\mu_3$-O)$_2$($\mu_3$-OLi)$_2$($\mu_2$-CO$_2^-$)$_2$]Ce(H)(THF)]Li coordination environment gives an R-factor of 0.0146.

TABLE 23

Summary of EXAFS fitting parameters for CeOH-BTC

| Sample | CeOH-BTC | |
|---|---|---|
| Fitting range | k 2.5-8.9 Å$^{-1}$ R 1.1-5.0 Å | |
| Independent points | 15.6 | |
| Variables | 10 | |
| Reduced chi-square | 109 | |
| R-factor | 0.014 | |
| S$_0^2$ | 1.000 | |
| ΔE$_0$(eV) | 7.86 ± 2.22 | |
| R (Ce-$\mu_3$-O) (Å) | 2.24 ± 0.01 | N = 4 |
| R (Ce—O$^{CO2-}$) (Å) | 2.50 ± 0.01 | N = 2 |
| R(Ce-$\mu_1$-O) (Å) | 2.43 ± 0.03 | N = 2 |
| R (Ce—Ce) (Å) | 3.90 ± 0.15 | N = 4 |
| R (Ce—C$^{CO2-}$) (Å) | 3.37 ± 0.07 | N = 2 |
| R (Ce—O$^{CO2\text{-}distal}$) (Å) | 3.89 ± 0.07 | N = 2 |

TABLE 24

Summary of EXAFS fitting parameters for CeH-BTC

| Sample | CeH-BTC | |
|---|---|---|
| Fitting range | k 2.4-7.2 Å$^{-1}$ R 1.0-5.2 Å | |
| Independent points | 16.5 | |
| Variables | 11 | |
| Reduced chi-square | 480 | |
| R-factor | 0.015 | |
| S$_0^2$ | 1.000 | |
| ΔE$_0$(eV) | 9.40 ± 0.00 | |
| R (Ce-$\mu_3$-O) (Å) | 2.44 ± 0.25 | N = 4 |
| R (Ce—O$^{CO2-}$) (Å) | 2.65 ± 0.28 | N = 2 |
| R (Ce—H) (Å) | 2.46 ± 0.05 | N = 1 |
| R (Ce—O$^{THF}$) (Å) | 2.60 ± 0.20 | N = 1 |
| R (Ce—Ce) (Å) | 3.95 ± 0.20 | N = 4 |
| R (Ce—C$^{CO2-}$) (Å) | 3.63 ± 0.20 | N = 2 |
| R (Ce—O$^{CO2\text{-}distal}$) (Å) | 3.77 ± 0.05 | N = 2 |

Example 23

CeH-BTC-Catalyzed Hydroboration of Pyridines

A Typical Procedure for CeH-BTC Catalyzed Hydroboration of Pyridines:

CeOH-BTC (86.8 µmol Ce) was prepared as described above. Pyridine (175 µL, 2.17 mmol) was added to a solution of CeOH-BTC and pinacolborane (473 µL, 3.26 mmol). The reaction mixture was stirred under nitrogen at 80° C. for 36 h. The MOF was removed from the solution by centrifugation. The supernatant was transferred to a vial, and the MOF was washed with THF. The combined organic extracts were concentrated in vacuo to afford a mixture of 1-(4,4,5,5-tetramethyl-1,3,2-dioxaborolan-2-yl)-1,4-dihydropyridine (1.45 mmol, 67% NMR yield based on mesitylene as an internal standard) and 1-(4,4,5,5-tetramethyl-1,3,2-dioxaborolan-2-yl)-1,2-dihydropyridine (0.092 mmol, 5% NMR yield based on mesitylene as an internal standard). Results from the CeH-BTC-catalyzed hydroboration of various pyridines are summarized in FIG. 35.

Recycling Experiment:

Scheme 24. Recycling of CeH—BTC
for the hydroboration of pyridine with pinacolborane.

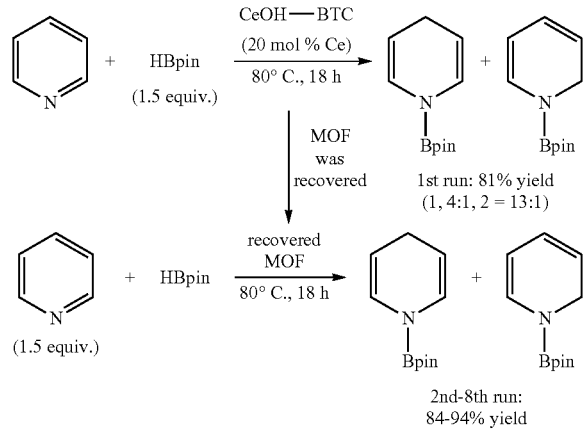

Figure 36:
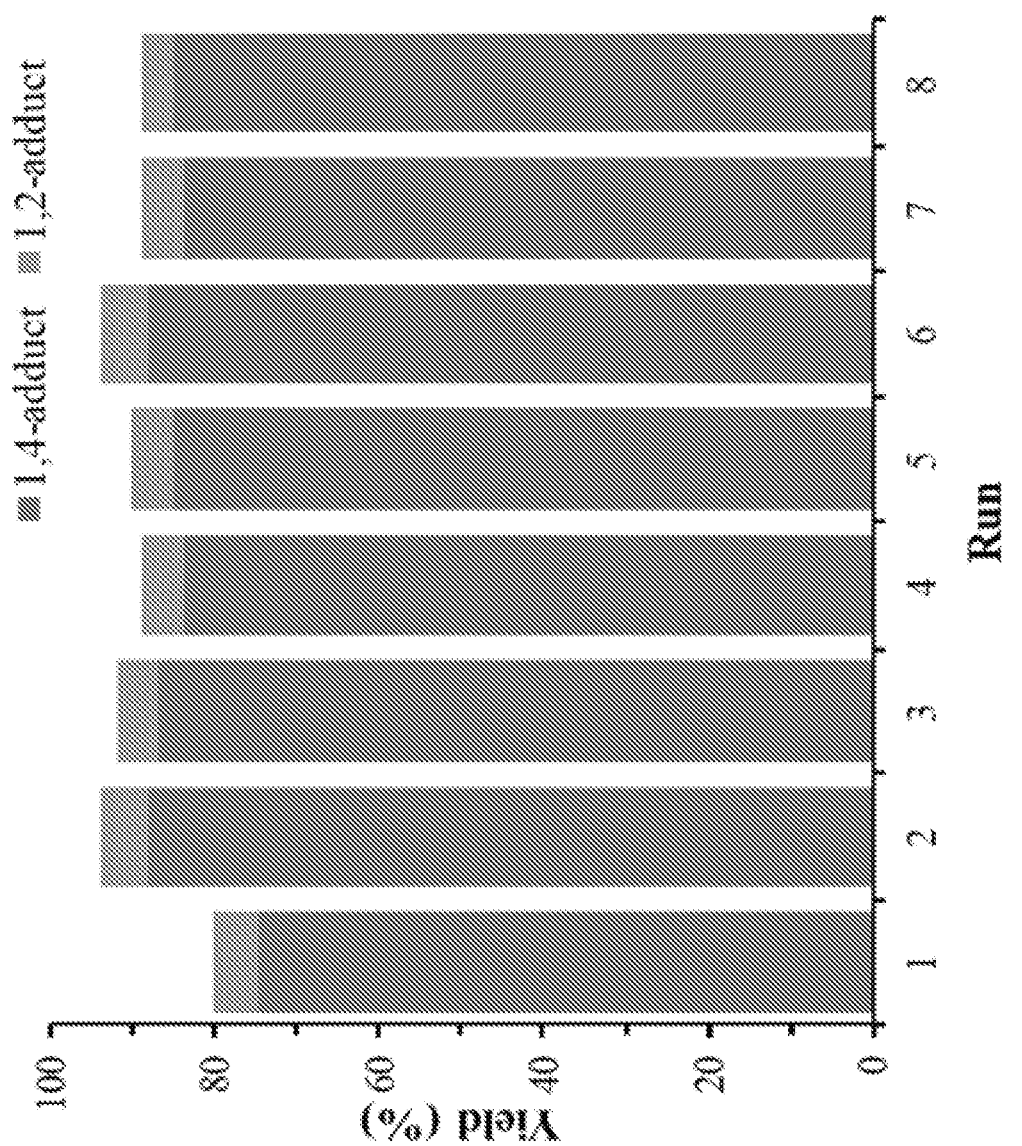
FIG. 36 is a graph plotting the yields (%) of 1-(4,4,5,5-tetramethyl-1,3,2-dioxaborolan-2-yl)-1,4-dihydropyridine and 1-(4,4,5,5-tetramethyl-1,3,2-dioxaborolan-2-yl)-1,2-dihydropyridine at different runs in the recycling experiments of the reduced metal organic framework (CeOH-BTC) for use as a catalyst in the hydroboration of pyridine with pinacolborane. The Ce-loadings were 20 mol %. The yield of 1,4-adduct is indicated by the dark grey portion of each bar, while the yield of 1,2-adduct is indicated by the light grey portion of each bar.

As shown in Scheme 24, above, CeOH-BTC (347.2 μmol Ce) was prepared as described above. A mixture of pyridine (140 μL, 1.74 mmol), pinacolborane (379 μL, 2.61 mmol), and CeOH-BTC was stirred at 80° C. for 18 h. The MOF was removed from the solution by centrifugation. The supernatant was transferred to a vial, and the MOF was washed with THF. The combined organic extracts were concentrated in vacuo to give a mixture of 1-(4,4,5,5-tetramethyl-1,3,2-dioxaborolan-2-yl)-1,4-dihydropyridine (1.31 mmol, 75% yield NMR yield based on mesitylene as an internal standard) and 1-(4,4,5,5-tetramethyl-1,3,2-dioxaborolan-2-yl)-1,2-dihydropyridine (0.087 mmol, 5% NMR yield based on mesitylene as an internal standard). The recovered solid catalyst was used for subsequent reactions. The reaction mixture of pyridine (210 μL, 2.61 mmol), pinacolborane (252 μL, 1.74 mmol), and the recovered MOF was stirred for 18 h in each run. FIG. 36 is a graph showing the yields (%) of 1-(4,4,5,5-tetramethyl-1,3,2-dioxaborolan-2-yl)-1,4-dihydropyridine and 1-(4,4,5,5-tetramethyl-1,3,2-dioxaborolan-2-yl)-1,2-dihydropyridine at different runs in the recycling experiments of CeOH-BTC for hydroboration of pyridine with pinacolborane. The Ce-loadings were 20 mol %.

Example 24

CeH-BTC-Catalyzed Hydroboration of Alkenes

Scheme 25. CeH—BTC-Catalyzed Hydroboration of Alkenes.

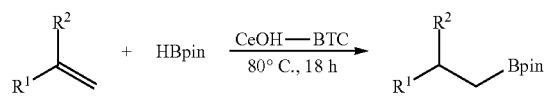

CeH-BTC was used to catalyze the hydroboration of alkenes as shown in Scheme 25, above.

A Typical Procedure for CeH-BTC Catalyzed Hydroboation of Alkenes:

CeOH-BTC (10 mg, 21.7 μmol Ce) was prepared as described above. Styrene, as an exemplary alkene (499 μL, 4.34 mmol), was added to a solution of CeOH-BTC and pinacolborane (945 μL, 6.51 mmol). The reaction mixture was stirred under nitrogen at 80° C. for 18 h. The MOF was removed from the solution by centrifugation. The supernatant was transferred to a clean round bottom flask, and the MOF was washed with THF. The combined organic extracts were concentrated in vacuo to afford 4,4,5,5-tetramethyl-2-(2-phenylethyl)-1,3,2-dioxaborolane (3.43 mmol, 79% NMR yield based on $CH_3NO_2$ as an internal standard). Table 25 shows the results of CeH-BTC catalyzed hydroboration of various alkenes.

TABLE 25

CeH-BTC-Catalyzed Hydroboration of Alkenes.

| Entry | Substrate | Catalyst Loading (mol % Ce) | Yield (%)[a] |
|---|---|---|---|
| 1 | styrene | 0.1 | 40 |
| 2 | styrene | 0.5 | 79 |
| 3 | 4-F-styrene | 1 | 99 |
| 4[b] | allylbenzene | 1 | 90 |
| 5[b] | 1-heptene | 1 | 97 |
| 6[b,c] | α-methylstyrene | 1 | 56 |

[a]NMR yield using $CH_3NO_2$ as an internal standard.
[b]36 h.
[c]100° C.

Recycling Experiment:

Scheme 26. Recycling of CeH—BTC
for the hydroforation of styrene with pinacolborane.

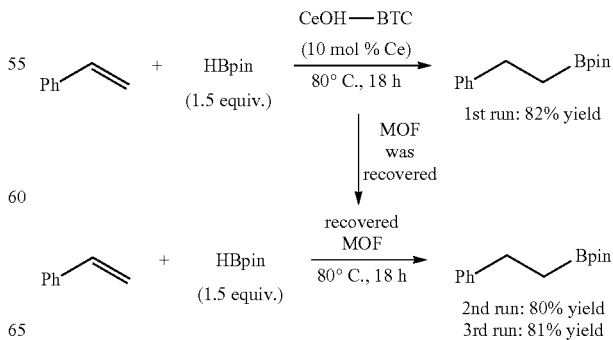

CeOH-BTC (173.6 μmol Ce) was prepared as described above. A mixture of styrene (200 μL, 1.74 mmol), pinacolborane (379 μL, 2.61 mmol), and CeOH-BTC was stirred at 80° C. for 18 h. The MOF was removed from the solution by centrifugation. The supernatant was transferred to a clean round-bottom flask, and the MOF was washed with THF. The combined organic extracts were concentrated on a rotary evaporator to give 4,4,5,5-tetramethyl-2-(2-phenylethyl)-1,3,2-dioxaborolane (1.43 mmol, 82% NMR yield based on CH$_3$NO$_2$ as an internal standard). The recovered solid catalyst was used for a subsequent reaction, and the reaction mixture was stirred for 18 h in each run.

Example 25

CeH-BTC-Catalyzed Hydrophosphination of Alkenes

Scheme 27. CeH—BTC-Catalyzed Hydrophosphination of Alkenes.

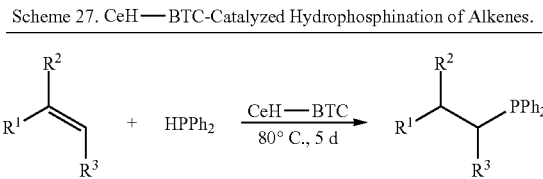

CeH-BTC was used to catalyze the hydrophosphination of alkenes as shown in Scheme 27, above.

A Typical Procedure for CeH-BTC Catalyzed Hydrophosphination of Alkenes:

CeH-BTC (43.4 μmol Ce) was prepared as described above. 1-Octene (171 μL, 1.09 mmol) was added to a solution of CeH-BTC and diphenylphosphine (285 mL, 1.64 mmol). The reaction mixture was stirred under nitrogen at 80° C. for 5 d. The MOF was removed from the solution by centrifugation. The supernatant was transferred to a clean vial, and the MOF was washed with THF. The combined organic extracts were concentrated in vacuo. The yield of n-octyldiphenylphosphine was determined by $^1$H NMR with CH$_3$NO$_2$ as an internal standard (1.08 mmol, 99% yield). Table 26 shows the results of CeH-BTC catalyzed hydrophosphination of various alkenes.

TABLE 26

CeH-BTC-Catalyzed Hydrophosphination of Alkenes.

| Entry | Substrate | Product | Cat. Loading (mol% Ce) | Yield (%)[a] |
|---|---|---|---|---|
| 1[b] | ~~~~/5 | ~~~~/5 PPh$_2$ | 4 | 74 |
| 2 | | | 4 | 99 |
| 3 | ~~~~/7 | ~~~~/7 PPh$_2$ | 4 | 75 |
| 4 | Cl~~~~/4 | Cl~~~~/4 PPh$_2$ | 4 | 80 |
| 5 | Me~~~~/3 (Me) | Me~~~~/3 PPh$_2$ (Me) | 12 | 50 |
| 6[c] | Ph~~/Me | Ph~~(Me)PPh$_2$ | 12 | 41 |

[a] $^1$H NMR yield was determined by CH$_3$NO$_2$ as an internal standard.
[b] 18 h.
[c] 100° C.

Recycling Experiment:

Scheme 28. Recycling of CeH—BTC for the hydrophosphination of 1-octene with diphenylphosphine.

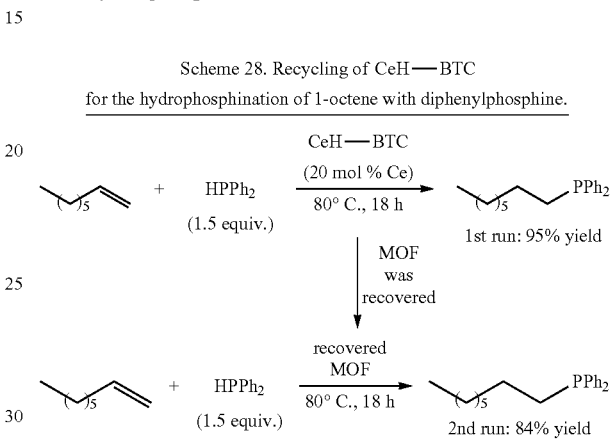

A mixture of 1-octene (170 μL, 1.09 mmol), diphenylphosphine (285 μL, 1.64 mmol), and CeH-BTC (217 μmol) was stirred at 80° C. for 18 h. CeH-BTC was removed from the solution by centrifugation. The supernatant was transferred to a vial, and the MOF was washed with THF. The combined organic extracts were concentrated in vacuo to give n-octyldiphenylphosphine (1.08 μmol, 99% yield). The recovered solid catalyst was used for subsequent reactions, and the reaction mixture was stirred for 36 h in each run.

Example 26

Summary of Examples 21-25

Ce$^{IV}_6$(μ$_3$-O)$_4$(μ$_3$-OH)$_4$(OH)$_6$(OH$_2$)$_6$ nodes in a Ce-BTC (BTC=trimesic acid) MOF can be directly transformed into previously unknown organometallic Ce$^{III}_6$ (μ$_3$-O)$_4$(μ$_3$-OLi)$_4$(H)$_6$(THF)$_5$ nodes. The resulting CeH-BTC catatyst can be used in the catalytic hydroboration of pyridines and alkenes, as well as the hydrophosphination of alkenes. The CeH-BTC catalyst can exhibit high activity and unique regioselectivity, likely a result of its low steric hindrance and electron density compared to existing homogeneous lanthanide catalysts.

Figure 37A:
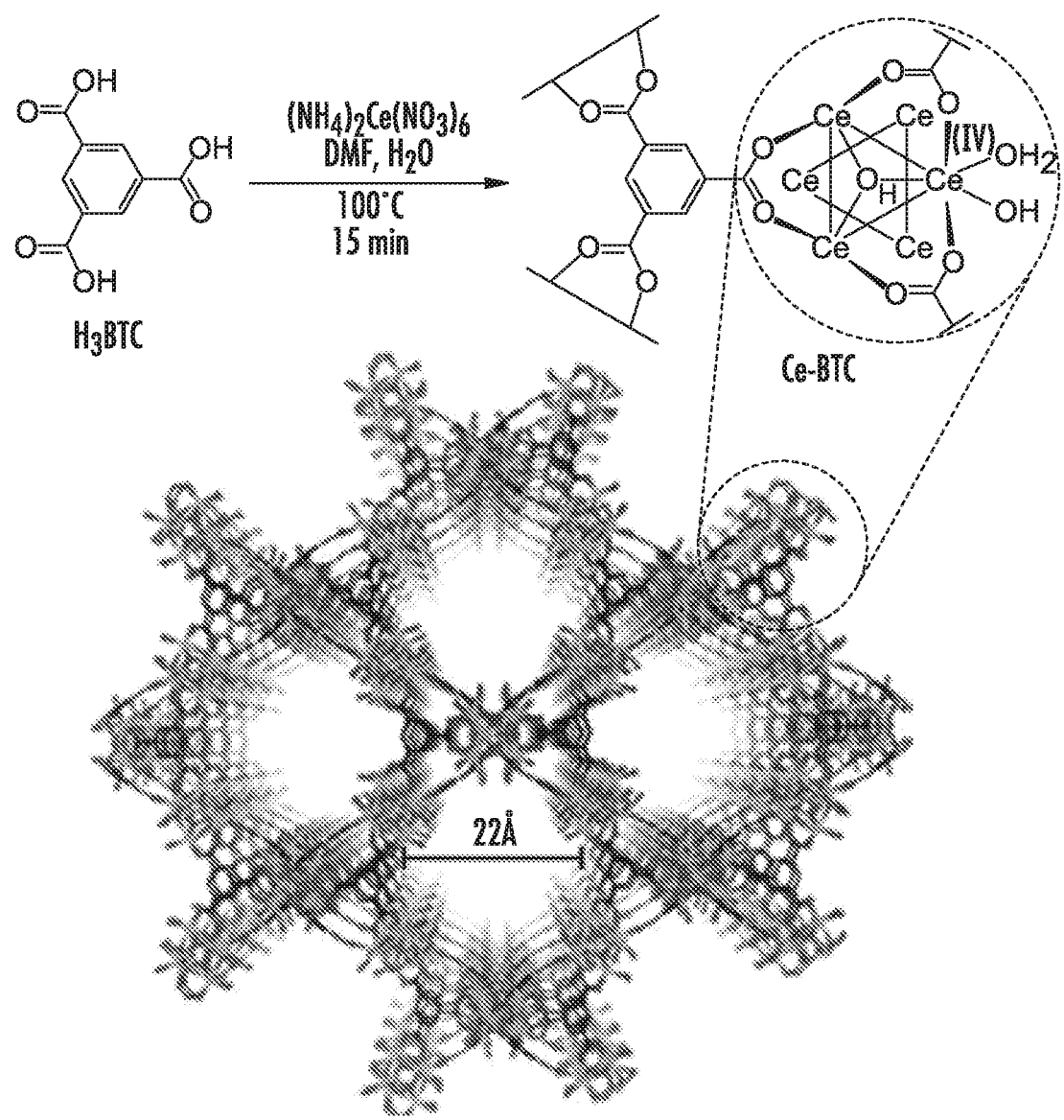
FIG. 37A is schematic drawing showing the synthesis and a structural model of the metal organic framework (Ce-BTC) described in FIG. 26.
Figure 37B:
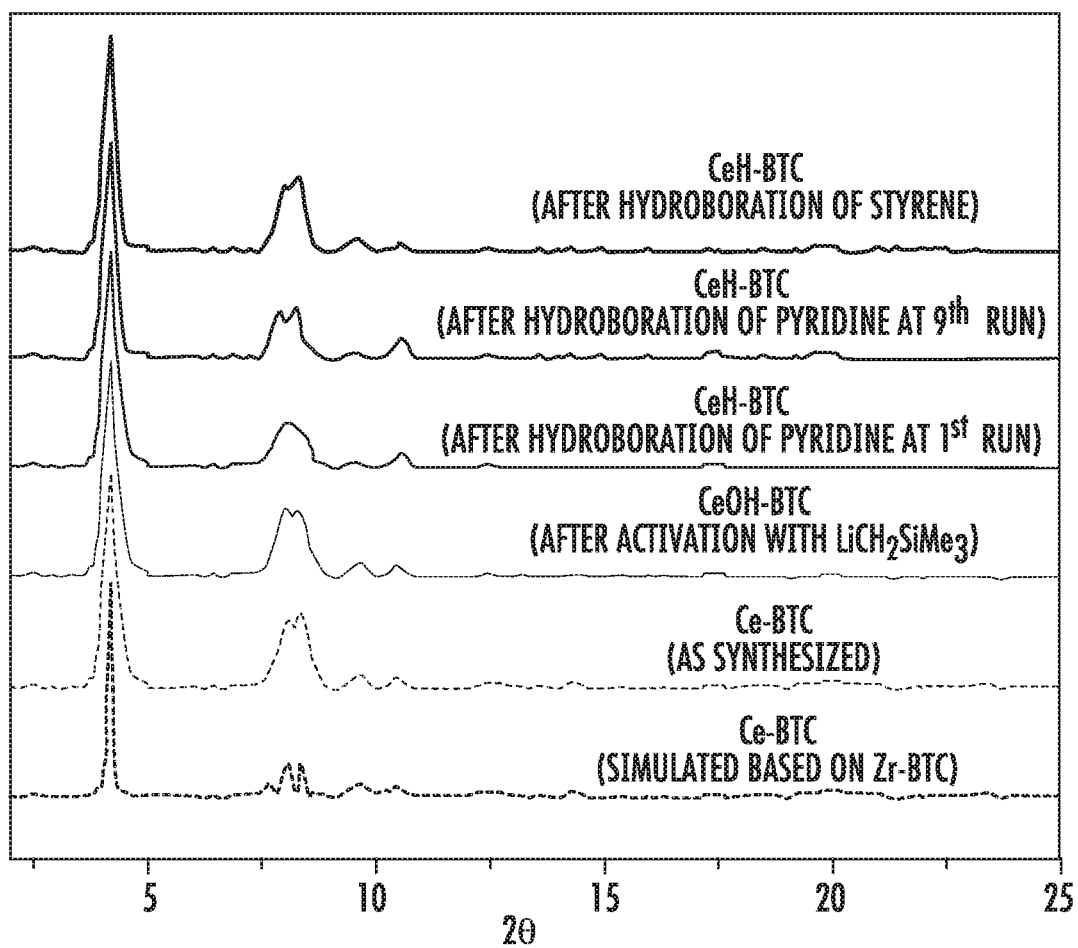
FIG. 37B is a graph of powder x-ray diffraction (PXRD) patterns: a simulated PXRD pattern of the metal organic framework (Ce-BTC) described in FIG. 26 based on the corresponding zirconium (Zr) form (Zr-BTC), the experimental PXRD pattern of the as-synthesized Ce-BTC, the experimental PXRD pattern of the activated form (CeOH-BTC), the experimental PXRD pattern of the corresponding catalyst after use one time in the hydroboration of pyridine; the experimental PXRD pattern of the corresponding catalyst after use nine times in the hydroboration of pyridine; and the experimental PXRD patter of the corresponding catalyst after use in the hydroboration of styrene.

Ce-BTC was synthesized in 54% yield by treating (NH$_4$)$_2$Ce(NO$_3$)$_6$ with H$_3$BTC in a mixture of DMF and H$_2$O at 100° C. See FIG. 37A. The structure of Ce-BTC was modeled using the crystal structure of Zr-BTC (MOF-808) by elongating the Ce-μ$_3$-O distance to 2.25 Å (from a Zr-μ$_3$-O distance of 2.16 Å). See Furukawa et al., J. Am. Chem. Soc., 2014, 136, 4369. Similarities between powder X-ray diffraction (PXRD) patterns of as-synthesized Ce-BTC and the simulated pattern confirmed the spn topology. See FIG. 37B. It is believed that the Ce centers possess square antiprismatic geometry, with a composition of [($\mu_3$-O)$_2$($\mu_3$-OH)$_2$($\mu_2$-CO$_2^-$)$_2$]Ce(OH)(OH$_2$), similar to the Zr coordination in MOF-808. As Ce$^{4+}$ has a larger ionic radius than Zr$^{4+}$[r(Ce$^{4+}$)=0.97 Å and r(Zr$^{4+}$)=0.84 Å], the Ce$_6$ node in Ce-BTC is larger than the Zr$_6$ node in MOF-808, with a Ce—Ce distance of 3.74 Å vs the Zr—Zr distance of 3.57 Å.

N$_2$ sorption isotherms of Ce-BTC at 77 K gave a Brunauer-Emmett-Teller (BET) surface area of 1008 m$^2$/g and a largest pore size of 22 Å, which corresponds well to the size of the hexagonal pore in the simulated structure of Ce-BTC. See FIG. 37A. The Ce oxidation state of Ce-BTC was studied by X-ray adsorption near-edge spectroscopy (XANES) and compared to (NH$_4$)$_2$Ce$^{IV}$(NO$_3$)$_6$ and Ce$^{III}$Cl$_3$ standards. Ce-BTC shows two XANES peaks at 5730 and 5738 eV (See FIG. 26), which are identical to the Ce$^{IV}$ standard, indicating the +4 oxidation state in Ce-BTC. Without being bound to any one theory, the stability of Ce$^{IV}$ toward potential reductants, including DMF and water, was attributed to carboxylate coordination. See Piro et al., Coord. Chem. Rev., 2014, 260, 21. $^1$H NMR of digested Ce-BTC in D$_3$PO$_4$/DMSO-d$_6$ showed only the peaks of H$_3$BTC and adsorbed solvents, consistent with the coordination of H$_2$O and OH— to Ce$^{IV}$. Extended X-ray adsorption fine-structure (EXAFS) fitting of the Ce region (see FIG. 27) supported the proposed structural model, with a Ce—OH/Ce—OH$_2$ average distance of 2.43 Å, close to typical Ce$^{(IV)}$—O distances. See Behrsinq et al., Inorg. Chem. Acta, 2003, 352, 229.

The Ce coordination environment of [($\mu_3$-O)$_2$($\mu_3$-OH)$_2$($\mu_2$-CO$_2^-$)$_2$]Ce(OH)(OH$_2$) in Ce-BTC is analogous to those of Cp$_2$Ln(X)(L) (X=anionic ligand and L=neutral ligand) which have been used in many catalytic reactions. A structural model of Ce-BTC indicates that Ce—OH and Ce—OH$_2$ moieties point toward the large channel, affording low steric hindrance around the Ce centers. Thus, activating the Ce(OH)(OH$_2$) sites can prepare active Ce catalysts that are readily accessible to organic substrates via the large open channels of Ce-BTC.

Ce-BTC was activated by sequential deprotonation with LiCH$_2$SiMe$_3$ and reduction with pinacolborane (HBpin) to generate the first MOF-supported Ce-hydride catalyst for several important organic transformations. The lithiated MOF, denoted CeOH-BTC, was obtained by treating Ce-BTC with 10 equiv. of LiCH$_2$SiMe$_3$ (w.r.t. Ce), which deprotonated ($\mu_3$—OH)Ce(OH)(OH$_2$) to form [($\mu_3$-OLi)Ce(OH)$_2$]Li and SiMe$_4$. See FIG. 30. After removing CeOH-BTC, 1.74±0.15 equiv. of SiMe$_4$ (w.r.t. Ce) was detected in the supernatant by $^1$H NMR, which corresponded well to the calculated result of 1.67. Inductively coupled plasma-mass spectrometry (ICP-MS) analysis of CeOH-BTC gave a Li-to-Ce ratio of 1.69±0.05, also matching our calculated result of 1.67.

CeOH-BTC was reduced to form CeH-BTC by treatment with HBpin at 60° C. in THF for 6 h. See FIG. 31. GC analysis of the head space gas indicated the production of 0.5 equiv. of H$_2$ (w.r.t. Ce). After removal of CeH-BTC, 2.02±0.14 equiv. of HOBpin (w.r.t. Ce) was detected in the supernatant by $^1$H NMR, which corresponded to the calculated result (i.e., 2 equiv.). The identity of HOBpin was confirmed using $^{11}$B NMR ($\delta$=22.7 ppm, 128 MHz). Based on the formation of 0.5 equiv. of H$_2$ and 2 equiv. of HOBpin, and without being bound to any one theory, it is proposed that the reduction occurred via an H/OH exchange between HBpin and Ce(OH)$_2$ to form Ce$^{IV}$(H)$_2$ and HOBpin, followed by bimetallic reductive elimination of H$_2$ from neighboring Ce$^{IV}$(H)$_2$ species to form Ce$^{III}$H(THF). XANES of CeH-BTC showed a single Ce peak at 5726 eV, identical to the absorption feature of CeCl$_3$. See FIGS. 26 and 32.

Treatment of CeH-BTC with hydrochloric acid generated nearly one equiv. of H$_2$, while no H$_2$ was observed when Ce-BTC or CeOH-BTC was treated with hydrochloric acid. This experiment provides additional support for the formation of the CeH-BTC upon lithiation and reduction of Ce-BTC. The PXRD pattern of CeH-BTC is identical to that of Ce-BTC, indicating that the MOF framework remains intact after lithiation and reduction. See FIG. 37B. EXAFS fitting at the Ce edge corresponded to the proposed CeH (THF) coordination model, with an R-factor of about 0.015. See FIG. 34. EXAFS fitting afforded a Ce$^{III}$-($\mu_3$-O) distance of 2.44 Å in CeH-BTC, slightly longer than the Ce$^{IV}$-($\mu_3$-O) distance of 2.25 Å in CeOH-BTC, which is consistent with the increase of Ce ionic radius upon reduction. See Piro et al., Coord. Chem. Rev., 2014, 260, 21. It is expected that the [($\mu_3$-O)$_2$($\mu_3$-OH)$_2$(2-CO$_2^-$)$_2$]Ce moiety is less electron-rich than other organolanthanide fragments, such as Cp*$_2$Ln, potentially endowing the CeH-BTC catalyst with unique activity and selectivity.

CeH-BTC demonstrates high activity for several catalytic reactions and distinct selectivities from other lanthanide catalysts. Because 1,4-dihydropyridine is an important building block of natural products (see Bull et al., Chem. Rev., 2012, 112, 2642; and Lavilla, J. Chem. Soc., Perkin Trans. I, 2002, 1141), biologically active intermediates (see Edraki et al., Drug Discov. Today, 2009, 14, 1058), and reducing reagents (see ZhenQ et al., Chem. Soc. Rev., 2012, 41, 2498; Rueping et al., Green Chem., 2011, 13, 1084; and Ouellet et al., Acc. Chem. Res., 2007, 40, 1327), the activity of CeH-BTC was tested for the hydroboration of pyridines with HBpin. See FIG. 35. Although hydroboration of pyridines provides a convenient synthetic route to 1,4-dihydropyridines (see Fan et al., J. Am. Chem. Soc., 2015, 137, 4916), only one organoborane catalyst has been reported to effect 1,4-selective hydroboration reactions. See Intemann et al., Organometallics, 2014, 33, 5722; Dudnik et al., Nat. Chem., 2014, 6, 1100; Oshima et al., J. Am. Chem. Soc., 2012, 134, 3699; and Arrowsmith et al., Organometallics, 2011, 30, 5556. Reaction of pyridine with HBpin in the presence of 4 mol % CeOH-BTC at 80° C. for 36 h selectively gave the 1,4-addition product in 71% yield. The reaction did not proceed with Ce-BTC or without catalyst. The hydroboration of pyridines by CeH-BTC has a broad substrate scope. With 2 or 4 mol % catalyst loading, CeOH-BTC was able to convert 3-bromopyridine and 3-methylpyridine to their corresponding 1,4-addition products along with small amounts of 1,2-addition products. 3,5-Disubstututed pyridines, such as 3,5-dimethylpyridine, could also be hydroborated with 10 mol % CeH-BTC. CeH-BTC also exhibited good hydroboration activity for quinoline.

CeH-BTC is also active in the hydroboration of alkenes, a useful catalytic reaction in organic synthesis. See Beletskaya et al., Tetrahedron, 1997, 53, 4957; and Burcess, et al., Chem. Rev., 1991, 91, 1179. Reacting 1-octene and 1.5 eq. of HBpin in the presence of 0.1 mol % CeH-BTC at 80° C. for 18 h selectively gave the anti-Markovnikov-type addition product in 40% yield. See entry 1, Table 25. Increasing catalyst loading to 0.5 mol % afforded the addition product in 79% yield. See entry 2, Table 25. Hydroboration also proceeded for several other alkenes. For example, hydroboration of 4-fluorostyrene gave the corresponding addition product in high yield. See entry 3, Table 25. Aliphatic alkenes, such as allylbenzene and 1-octene, were also used in hydroboration. See entries 4 and 5, Table 25. Additionally, $\alpha$-methyl styrene, a disubstituted alkene, was a good substrate. See entry 6, Table 25.

Hydrophosphination of alkenes is a powerful, direct, and atom-economical method for obtaining organophosphines (see Koshti et al., Coord. Chem. Rev., 2014, 265, 52; and Delacroix et al., Current Organic Chemistry, 2005, 9, 1851), an important class of compounds for chemical, agrochemical, pharmaceutical industries. See Quin, "A Guide to Organophosphorous Chemistry," John Wiley & Sons, New York, 2000. Moreover, organophosphines are among the most important ligands in homogeneous catalysis. While several examples of hydrophosphination of alkenes have been reported, the scope of substrates is limited, and examples of hydrophosphination of unactivated aliphatic olefins are rare. See Ghebreab et al., J. Am. Chem. Soc., 2014, 136, 9240; and Leyva-Pérez et al., J. Organomet. Chem., 2011, 696, 362. CeH-BTC catalyzed hydrophosphination of various unactivated alkenes. At 4 mol % Ce-loading, hydrophosphination of 1-octene for 18 h selectively yielded 74% of n-octyldiphenylphosphine. See entry 1, Table 26. Prolonging the reaction to 5 d afforded the addition product in 99% yield. See entry 2, Table 26. Hydrophosphination also proceeded for 1-decene and 6-chlorohexene. See entries 3 and 4, Table 26. CeH-BTC displayed good activity for 2-methyl-1-pentene, an α-substituted alkene. See entry 5, Table 26. The hydrophosphination of cis-3-methylstyrene with diphenylphosphine gave 41% of the addition product. See entry 6, Table 26.

Several studies were conducted to demonstrate the heterogeneity of CeH-BTC. First, it was shown that the PXRD of CeH-BTC recovered from hydroboration of pyridines and alkenes remained the same as that of freshly prepared CeH-BTC. Second, ICP-MS was used to show that the amounts of Ce leaching into the supernatant during the hydroboration of pyridine and styrene and the hydrophosphination of 1-octene were less than 0.6%, 0.75%, and 0.03%, respectively. Finally, CeH-BTC could be recovered and reused 1 to 7 times without any loss of activity in each of the above reactions.

Accordingly, a new Ce-BTC MOF with a $Ce^{IV}_6(\mu_3\text{-O})_4(\mu_3\text{—OH})_4(OH)_6(OH_2)_6$ SBU was synthesized and the SBU of the MOF was transformed into a $[Ce^{III}_6(\mu_3\text{-O})_4(\mu_3\text{-OLi})_4(H)_6(THF)_6]^{6+}$ node, which can be used as an active catalyst for the selective hydroboration of pyridine and alkenes and hydrophosphination of alkenes. The CeH-BTC catalyst displayed lower steric hindrance and electron density than other lanthanide catalysts, which led to a unique 1,4-regio-selectivity for the hydroboration of pyridine. MOF nodes thus are believed to have potential for transformation into single-site solid catalysts without homogeneous counterparts for sustainable chemical synthesis.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for preparing a catalyst, said method comprising:
providing a parent metal-organic framework (MOF), wherein the parent MOF comprises (i) a secondary building unit (SBU) comprising a metal oxo cluster comprising a terminal or bridging OH or $OH_2$ group and (ii) an organic bridging ligand; and
reacting the parent MOF with a catalyst precursor, wherein the catalyst precursor is a compound of the formula $ML_nX$, wherein X is a halide, H, alkyl or aryl group, M is a catalytically active metal, n is an integer from 0 to 5, and each L is independently selected from the group consisting of H, a halide, an alkyl group, an aralkyl group, an aryl group, a heteroaryl group, an alkoxy group, and an amine, thereby forming a MOF catalyst comprising a SBU comprising a metal oxo cluster further comprising a —$OML_n$ group or a —$(OH)ML_n$ group.

2. The method of claim 1, wherein the SBU of the parent MOF is selected from the group consisting of Zr-oxo clusters, Hf-oxo clusters, Zn-oxo clusters, Ti-oxo clusters, Al-oxo clusters, Cu-carboxylate paddlewheels, and Ce-oxo clusters.

3. The method of claim 1, wherein the organic bridging ligand is substituted with one or more carboxylate, pyridine, and/or phosphonate moieties, optionally wherein the organic bridging ligand is a dicarboxylate, a tricarboxylate, or a tetracarboxylate.

4. The method of claim 3, wherein the organic bridging ligand comprises one or more aryl or arylene groups, optionally wherein the organic bridging ligand is selected from the group consisting of 1,4-bis(4-carboxyphenyl)benzene, p,p'-terphenyldicarboxylic acid (TPDC), methane tetrakis(p-biphenylcarboxylate) (MTBC), trimesic acid (BTC), 4,4'-bis(carboxyphenyl)-2-nitro-1,1'-biphenyl (TPHN), and 1,1'-biphenyl-4,4'-dicarboxylate.

5. The method of claim 1, wherein M is selected from the group consisting of Mg, Zr, Hf, V, Fe, Co, Cr, Mn, Ni, and Cu.

6. The method of claim 5, wherein the catalyst precursor is selected from $CoCl_2$, $Me_2Mg$, $Zr(CH_2Ph)_4$, and $FeBr_2$.

7. A method for preparing a catalyst, said method comprising:
providing a parent metal-organic framework (MOF), wherein the parent MOF comprises (i) a secondary building unit (SBU) comprising a metal oxo cluster comprising a terminal or bridging OH or $OH_2$ group and (ii) an organic bridging ligand; and
reacting the parent MOF with a catalyst precursor, wherein the catalyst precursor is a compound of the formula $ML_nX$, wherein X is a halide, H, alkyl or aryl group, M is a catalytically active metal, n is an integer from 0 to 5, and each L is independently selected from the group consisting of H, a halide, an alkyl group, an aralkyl group, an aryl group, a heteroaryl group, an alkoxy group, and an amine, thereby forming a MOF catalyst comprising a SBU comprising a —$OML_n$ group or a —$(OH)ML_n$ group,
wherein the parent MOF is reacted with a base prior to reaction with the catalyst precursor to form a deprotonated SBU, optionally wherein the base is a salt of a Group 1 element and a carbanion, amide or hydride, further optionally wherein the base is n-butyl lithium (n-BuLi) or trimethylsilylmethyllithium ($LiCH_2SiMe_3$).

8. A catalyst prepared according to the method of claim 1.

9. The method of claim 7, wherein the deprotonated SBU is reacted with a reducing agent, optionally wherein the reducing agent is a borane, further optionally wherein the reducing agent is pinacolborane.

10. The method of claim 9, wherein the SBU of the parent MOF comprises a Ce-oxo cluster, optionally wherein the parent MOF further comprises a trimesic acid organic bridging ligand.

11. A metal-organic framework (MOF) comprising (i) a secondary building unit (SBU), wherein the SBU comprises a metal oxo cluster comprising a first metal and further comprising one or more —$OM'L_x$ and/or —$(OH)M'L_x$ groups, wherein M' is a second metal, wherein said second metal is different than the first metal, x is an integer between 0 and 5, and each L is independently selected from the group consisting of H, a halide, an alkyl group, an aralkyl group, an aryl group, a heteroaryl group, an alkoxy group, and an amine, optionally wherein the 0 or OH of the —OM'L$_x$ or —(OH)M'L$_x$ group is a metalated terminal oxo group, a metalated oxygen from a deprotonated μ-OH group, a metalated terminal OH group, or a metalated bound water group; and (ii) an organic bridging ligand.

12. The MOF of claim 11, wherein the second metal is free of decomposition due to disproportionation.

13. The MOF of claim 11, wherein M' is selected from Li, Mg, Fe, Co, Cr, Mn, Ni, and Cu, optionally wherein M' is a catalytically active metal selected from Co, Fe, Cu and Mg.

14. The MOF of claim 11, wherein the SBU is derived from a Zr-oxo cluster, a Hf-oxo cluster, a Zn-oxo cluster, a Ti-oxo cluster, an Al-oxo cluster, a Cu-carboxylate paddlewheel, or a Ce-oxo cluster, optionally wherein the SBU is derived from a cubic or octahedral metal oxo cluster, further optionally wherein the cubic or octahedral metal oxo cluster is of the formula $Zr_8(\mu_2-O)_8(\mu_2-OH)_4$ or $Zr_6(\mu_3-O)_4(\mu_3-OH)_4$.

15. The MOF of claim 11, wherein the MOF comprises a plurality of SBUs comprising one or more —OM'L$_x$ and/or —(OH)M'L$_x$ groups, optionally wherein each SBU comprises between 1 and 4 —OM'L$_x$ and/or —(OH)M'L$_x$ groups.

16. The MOF of claim 11, wherein the MOF has the formula $Zr_6O_4(OH_{4-n})(OM'L)_n(O_2CR)_{12}$, wherein n is an integer between 1 and 4, M' is Co, Fe, Cu or Mg, L is H or a halide, and R is an arylene group.

17. The MOF of claim 11, wherein the SBU has the formula $Ce^{III}_6(\mu_3-O)_4(\mu_3-OLi)_4(H)_6(THF)_6$.

18. A method for preparing a compound comprising contacting a substrate capable of forming a product by catalytic transformation with a heterogeneous catalyst of claim 8, wherein the catalytic transformation is selected from the group consisting of ethylene oligomerization, alkyne coupling, hydromethylation, alkane dehydrosilation, alkane metathesis, dehydrogenative alkyl C—H phosphination, pyridine functionalization, dehydrocoupling, hydrosilation of olefins, ketones and aldehydes, oxidation of primary alcohols, hydroamination, hydroformylation, C—H borylation, hydrogenation of alkenes, imines, carbonyls, nitroarenes, and heterocycles, hydroboration, hydrophosphination, and C—H amination.

19. The method of claim 18, wherein the catalytic transformation is conducted in a batch reactor, a flow reactor, or in a supercritical fluid reactor.

20. A catalyst prepared according to the method of claim 7.

* * * * *